(12) United States Patent
Wang

(10) Patent No.: US 9,402,376 B2
(45) Date of Patent: Aug. 2, 2016

(54) TRANSGENIC MICE EXPRESSING MICRORNA34 THAT HAVE CELLS DISPLAYING INCREASED SENESCENCE AND APOPTOSIS

(71) Applicant: Advanced Genomic Technology, LLC, Louisville, KY (US)

(72) Inventor: Eugenia Wang, Louisville, KY (US)

(73) Assignee: ADVANCED GENOMIC TECHNOLOGY, LLC, Louisville, KY (US)

( * ) Notice: Subject to any disclaimer, the term of this patent is extended or adjusted under 35 U.S.C. 154(b) by 0 days.

(21) Appl. No.: 14/371,628

(22) PCT Filed: Jan. 11, 2013

(86) PCT No.: PCT/US2013/021165
§ 371 (c)(1),
(2) Date: Jul. 10, 2014

(87) PCT Pub. No.: WO2013/106662
PCT Pub. Date: Jul. 18, 2013

(65) Prior Publication Data
US 2014/0342370 A1 Nov. 20, 2014

Related U.S. Application Data

(60) Provisional application No. 61/586,291, filed on Jan. 13, 2012, provisional application No. 61/586,361, filed on Jan. 13, 2012, provisional application No. 61/636,477, filed on Apr. 20, 2012.

(51) Int. Cl.
*A01K 67/027* (2006.01)
*C12Q 1/68* (2006.01)

(52) U.S. Cl.
CPC .......... *A01K 67/0275* (2013.01); *C12Q 1/6883* (2013.01); *A01K 2217/052* (2013.01); *A01K 2217/20* (2013.01); *A01K 2227/105* (2013.01); *A01K 2267/03* (2013.01); *C12Q 2600/136* (2013.01)

(58) Field of Classification Search
USPC .................................... 800/3, 8, 18; 435/325
See application file for complete search history.

(56) References Cited

U.S. PATENT DOCUMENTS

| 7,667,090 B2 * | 2/2010 | Croce ................. A01K 67/0275 800/18 |
| 2006/0179501 A1 * | 8/2006 | Chan .................. A01K 67/0275 800/18 |
| 2010/0291673 A1 | 11/2010 | Harper et al. |

FOREIGN PATENT DOCUMENTS

| WO | WO 2009/009457 A1 | 1/2009 |
| WO | WO 2009/062169 | * 5/2009 |
| WO | WO 2011/163116 A2 | 12/2011 |

OTHER PUBLICATIONS

Hansen (PLoSOne, Nov. 29, 2010, vol. 5, No. 11, e15497, p. 1-7).*
Zovoilis (EMBO, 2011, vol. 30, No. 20, p. 4299-4308, and Supplemental Materials).*
Xiao (Nature Immunol., Apr. 2008, vol. 9, No. 4, p. 405-414).*
Cowan (Xenotransplantation, 2003, vol. 10, p. 223-231).*
Ageta-Ishahara (Molecular Brain, 2013, 6:35, p. 1-14).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
Kelder (Advances in Exp. Med. and Biol. 2001, vol. 501, p. 269-278).*
Wang et al.; "miR-34a, a microRNA up-regulated in a double transgenic mouse model of Alzheimer's disease, inhibits bc12 translation"; Brain Research Bulletin; vol. 80 No. 4-5; Oct. 2009; p. 268-273.
Zovoilis et al.; microRNA-34c is a novel target to treat dementias; The EMBO Journal; vol. 30 No. 20; Sep. 2011; p. 4299-4308.
Zovoilis; Supplementary Material; Online Material; www.nature.com/emboj/journal/v30/n20/extref/emboj2011327; accessed Feb. 21, 2013; 19 pages.
International Patent Application No. PCT/US2013/21165; International Search Report and the Written Opinion; dated Mar. 26, 2013; 13 pages.
Wang et al.; "Senescent Human Fibroblasts Resist Programmed Cell Death, and Failure to Suppress bcl2 Is Involved"; Cancer Research; vol. 55; Jun. 1995; p. 2284-2292.
Hao et al.; "Intensive Inhibition of hTERT Expression by a Ribozyme Induces Rapid Apoptosis of Cancer Cells through a Telomere Length-Independent Pathway"; Cancer Biology & Therapy; vol. 4 Issue 10; Oct. 2005; p. 1098-1103.
Liu et al.; "Transcriptional Analysis of Normal Human Fibroblast Responses to Microgravity Stress"; Geno. Prot. Bioinfo.; vol. 6 No. 1; 2008; p. 29-41.
Ito et al.; "MicroRNA-34a regulation of endothelial senescence"; Biochemical and Biophysical Research Communications; vol. 398; 2010; p. 735-740.
Christoffersen et al.; "p53-independent upregulation of miR-34a during oncogene-induced senescence repress MYC"; Cell Death and Differentiation; vol. 17, 2010; p. 236-245.
Li et al.; "Circulatory miR-34a as an RNA-based, noninvasive biomarker for brain aging"; Aging; vol. 3 No. 10; Oct. 2011; p. 985-1002.
European Patent Application No. 13735972.5; Extended Search Report; dated Oct. 26, 2015; 10 pages.

* cited by examiner

*Primary Examiner* — Michael Wilson
(74) *Attorney, Agent, or Firm* — Baker & Hostetler LLP

(57) ABSTRACT

A transgenic, non-human animal model for accelerated aging and/or age-related symptom, recombinant nucleic acid molecules, cells and methods that can be used to make such animal model and cells, methods of using the animal model and cells, to descendants of the transgenic non-human animal, obtained by breeding with the same or with another phenotype, and to a cell line or primary cell culture or to an organotypic brain slice culture, derived from the transgenic non-human animal or its descendants are disclosed.

9 Claims, 56 Drawing Sheets hUbi Primers and GenBank Reference Number

Mfel hUbi Forward Primer: CAATTGAGTGGCTGGGAAATTGAGG

BglII hUbi Reverse Primer: AGATCTGCATTGTCTAACAAAAAGCCAAA hUbi GenBank Reference Number: NT_009755

FIG. 7A mSyn1 Primers and GenBank Reference

Mfel mSyn Forward Primer: CAATTG CGGCCACTGTGTGAAGCGT mSyn Reverse Primer BamHI: GGTGGCGGCGGTGGGGCAGG GGATCC mSyn GenBank Reference Number: NT_039700.8

FIG. 7B

LacZ Primers and GenBank Reference Number

NheI LacZ Forward Primer: GCTAGC TCGTTTACTTTGACCAACAAG

LacZ Reverse Primer: TTATTTTTGACCACCAGACCAA

LacZ-GT-F Overlap Extension Primer: GTTGCAGTGCACGGCAGATACACTTGCTGA

LacZ-GT-R Overlap Extension Primer: GCCACTGGTGTGGGCCATAATTCAATTCGC

LacZ GenBank Reference Number: NC_077779.1

FIG. 8A hmiR33b Scaffold Primers and GenBank Reference Number hmiR33a Scaffold Forward Primer: CAGCCTGACCATCTGTGAGA hmiR33a Scaffold Reverse Primer: AAGCAGTCACACAGGAACA hmiR33a GenBank Reference Number: NT_010718.16

FIG. 8B

Human Growth Hormone Poly A Primers and GenBank Number hGH Poly A Signal Forward Primer: TGCATCCCTGTGACCCCTCCC

NotI hGH Poly A Signal Reverse Primer: GCGGCCGCCATGAGAGGACAGTGCCAAGCA hGH Poly A Signal GenBank Reference Number: NT_010783.15

FIG. 8C

Sequence of hsa-34a Precursor:
5'
GGCCAGCTGTGAGTGTTTCTTTGGCAGTGTCTTAGCTGGTTGTTGTGAGCAATAGTAAGGAAGCAATCAGCAAGT
ATACTGCCCTAGAAGTGCTGCACGTTGTGGGCCC 3'

110 bp precursor; 122 bp PCR product with added restriction sites hsa34aSyn Forward Primer:
5' CTCGAGGGCCAGCTGTGAGTGTTTCT 3'
    XhoI hsa34aSyn and 34aUbi Reverse Primer:
5' GAATTCGGGCCCCACAACGTGCAGCAC 3'
    EcoRI hsa34aUbi Forward Primer:
5' AAGCTTGGCCAGCTGTGAGTGTTTCT 3'
    HindIII

FIG. 11 hsa-miR34c Precursor Sequence:
5' AGTCTAGTTACTAGGCAGTGTAGTTAGCTGATTGCTAATAGTACCAATCACTAACCACACGGCCAGGTAAAAA GATT 3'

(77 bp for precursor with restriction site of 12 bp added to it to make 89 bp)

Hsa-mir 34c Syn Forward primer: CTCGAGAGTCTAGTTACTAGGC
Hsa-mir 34c Syn/Ubi Reverse primer: GAATTCAATCTTTTTACCTGGC
Hsa-miR 34c Ubi Forward primer: AAGCTTAGTCTAGTTACTAGGC

FIG. 12

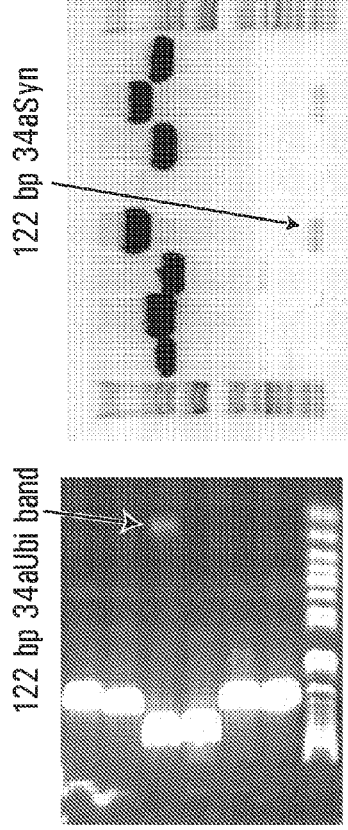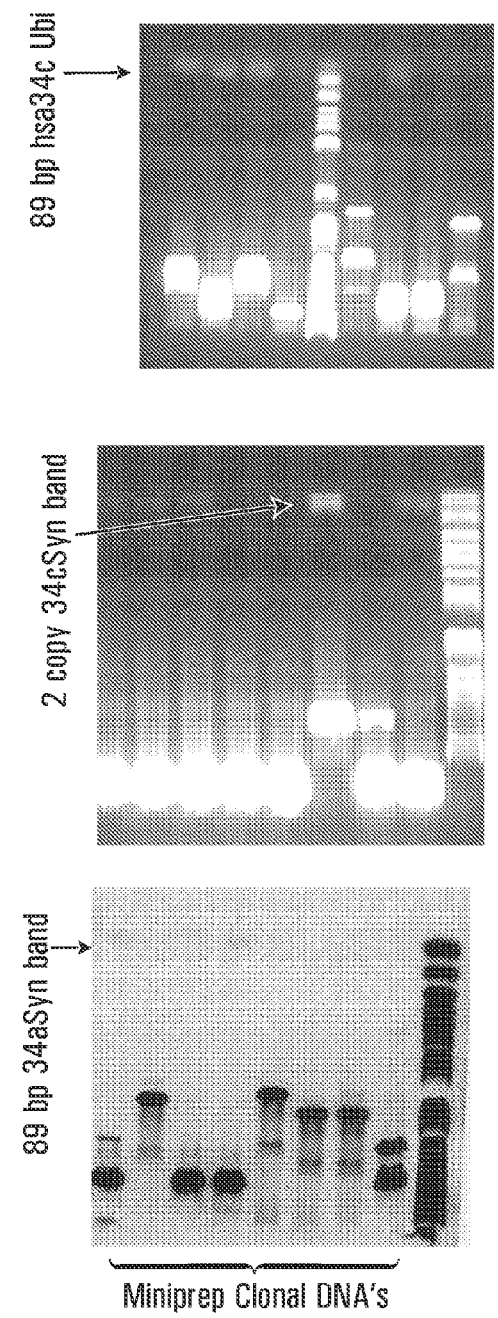

hsa-miR-34c

GTGAGGGGTGGGGTCAGGGTGGCCTGGCAGGGTGGGATTCAGCTTTCCATTCCCTGGTT
CCTCTCCCAGCCCCAGGGGCTGCAGAAGACCATGGGTTAGCCCAAGCAGCACAGGATA
GGGGTCCAGCAGACCCTGCTTTTGGCTAAGGCTTCTGTCCAGAGGAGAGGGGTTGCCC
CTATCTGGCCTCAGTTCCCCATCCTGGGAGGAGGGGTGGATGGTGTGGTAGGATCCC
TTTGGAGCCCTGCATCAGGAGGGCTGGACAGCTGCTCCGGGCGGGTGGCGGGTGTGG
GGGCCGAGAGAGATCTCGAGTCAAGCTTGGCCAGCTGTGAGTGTTTCTTTGGCAGTG
TCTTAGCTGGTTGTTGTGAGCAATAGTAAGGAAGCAATCAGCAAGTATACTGCCCTAGAAG
TGCTGCACGTTGTGGGGCCCGAATTCTGCAGTCGACGGCCCCATCCTGCCCCTCCAGA
GCTGGAGCCCTGGTGACCCTGCCACCCCCAGGCCGTGCAGTGTTCCTGTG
TGACCTGCTTGCATCCCTGTGACCCTGCCCTCTCCTGGCCCTGGAAGTGCCACTC
CAGTGCCCACCAGCCTTG

Forward Genotyping Primer=GGATTCAGCTTTCCATTCCCT
Reverse Genotyping Primer=CTGTTCCTGTGTGACCTGCTT (complementary to actual reverse primer)

hsamiR34a=AAGCTTGGCCAGCTGTGAGTGTTTCTTTGGCAGTGTCTTAGCTGGTTGTTGT
GAGCAATAGTAAGGAAGCAATCAGCAAGTATACTGCCCTAGAAGTGCTGCACGTTGTGGG
GCCCGAATTC

FIG. 21

GTGAGGGGTGGGGTCAGGGGTCTGGCAGGGCTGGGGATTCAGCTTTCCATTCCCTGGTTCCTCTCCC
CAGCCCCCAGGGCTGCAGAAGACCATGGGGTTAGCCAAGCAGCAGGATAGGGGTCCAGCAGA
CCCTGCTTTTGGCTAAGGCTTCTGTCCAGAGGAGAGGGGTTGCCCCTATCTGGCCTCAGTTTCCCATC
CCTGGGAGGGGGGGGGTGATGGTGTGGTAGGATCCCTTTGGAGGCTGCATCAGGAGGGGTGGAC
AGCTGCTCCCGGGCCGGGTGTGGGGGTGTGGGGCCGAGAGAGAGATCTCGAGAGTCTAGTTACTAGGC
AGTGTAGTTAGCTGATTGCTAAATAGTACCAATCACTAACCACACGGCCAGGTAAAAAGATTGAATTCTGC
AGTCGACGGGCCCCATCCTGCCCCTCCCAGAGCCCTGGTGACCCTGCCTGCCACC
CCAGGCCGTGCAGTCGTGTTCCTGTGTGACCTGCTTGCATCCCGTGACCCCTGTGCCTCTCCTGGCC
CTGGAAGTTGCCACTCCAGTGCCCACCAGCCTTG

Forward Genotyping Primer=GGATTCAGCTTTCCATTCCCT
Reverse Genotyping Primer=CTGTTCCTGTGTGACCTGCTT (complementary to actual reverse primer)

hsamiR34c=CTCGAGAGTCTAGTTACTAGGCAGTGTAGTTAGCTGATTGCTAAATAGTACCAATCACTAAC
CACACGGCCAGGTAAAAAGATTGAATTC

FIG. 22

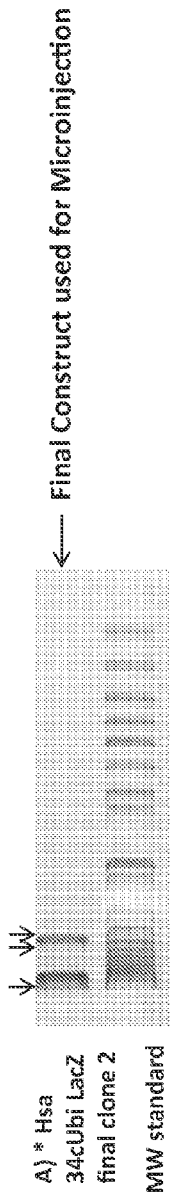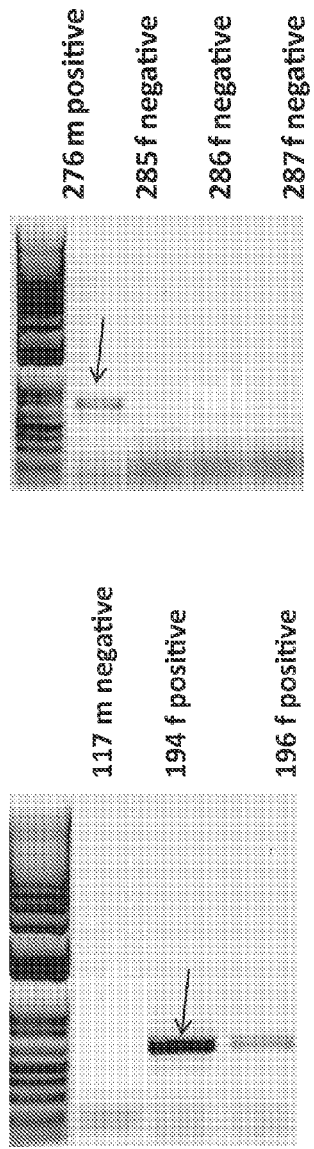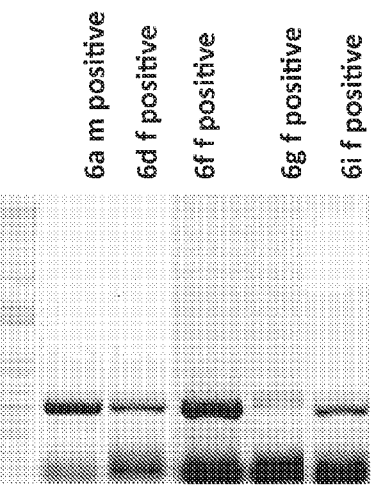
FIG. 24

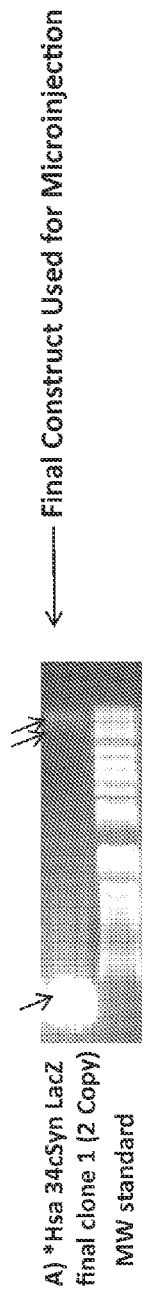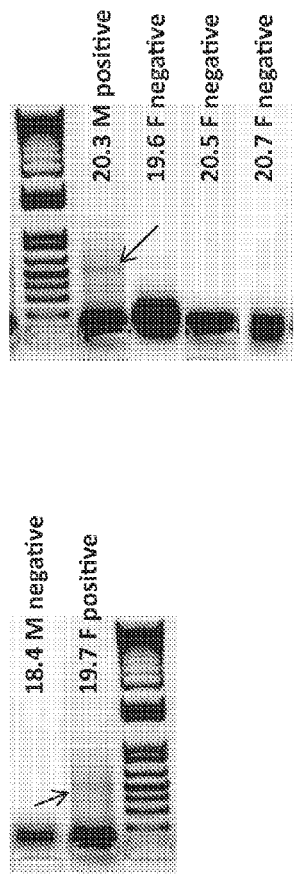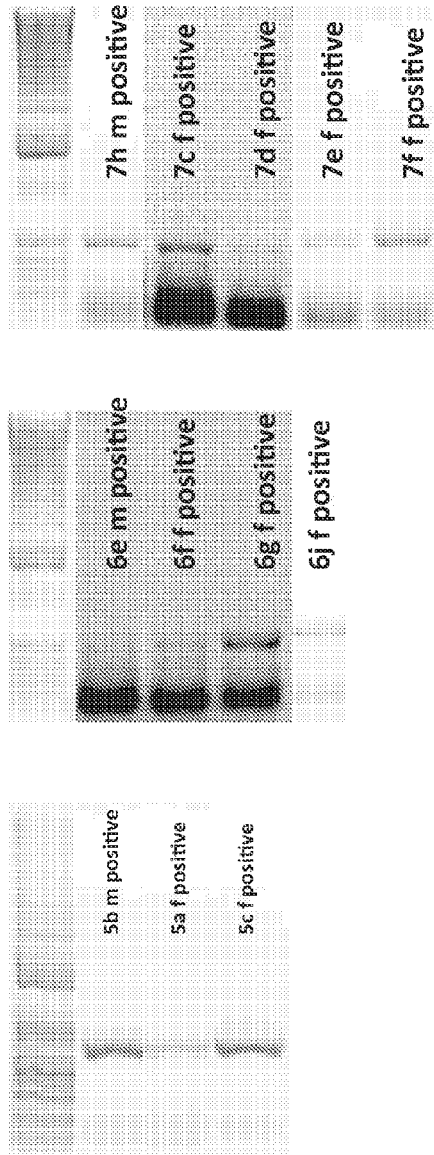
FIG. 27

AGTaU2 (MicroRNA hsa 34a Ubi Precursor and Mature Sequences)

Hsa miR34a Precursor Sequence
GGCCAGCUGUGAGUGUUUCUUUGGCAGUGUCUUAGCUGGUUGUGUGAGCAAUA
GUAAGGAAGCAAUCAGCAAGUAUACUGCCCUAGAAGUGCUGCACGUUGUGGGCCC Hsa miR34a Mature Sequence
UGGCAGUGUCUUAGCUGGUUGU

FIG. 30A

AGTcU2 (MicroRNA hsa 34c Ubi Precursor and Mature Sequences)

Hsa miR34c Precursor Sequence
AGUCUAGUUACUAGGCAGUGUAGUUAGCUGAUUGCUAAUAGUACCAAUCACUA
ACCACACGGCCAGGUAAAAAGAUU Hsa miR34c Mature Sequence
AAUCACUAACCACACGGCCAGG

FIG. 30B

AGTaS1 (MicroRNA hsa 34a mSyn Precursor and Mature Sequences)

Hsa miR34a Precursor Sequence
GGCCAGCUGUGAGUGUUUCUUUGGCAGUGUCUUAGCUGGUUGUGUGAGCAAUAG
UAAGGAAGCAAUCAGCAAGUAUACUGCCCUAGAAGUGCUGCACGUUGUGGGGCCC Hsa miR34a Mature Sequence
UGGCAGUGUCUUAGCUGGUUGU

FIG. 30C

AGTcS2 (MicroRNA hsa 34c mSyn Single Copy Precursor and Mature Sequences)

FIG. 30D

Hsa miR34c Single Copy Precursor Sequence

AGUCUAGUUACUAGGCAGUGUAGUUAGCUGAUUGCUAAUAGUACCAA
UCACUAACCACACGGGCCAGGUAAAAAGAUU

Hsa miR34c Single Copy Mature Sequence

AAUCACUAACCACACGGGCCAGG

AGTcS1 (MicroRNA hsa 34c mSyn two copy Precursor and Mature Sequences

FIG. 30E

Hsa miR34c 2 Copy Precursor Sequence

AGUCUAGUUACUAGGCAGUGUAGUUAGCUGAUUGCUAAUAGUACCAAUCACUAACCA
CACGGGCCAGGUAAAAAGAUU
AGUCUAGUUACUAGGCAGUGUAGUUAGCUGAUUGCUAAUAGUACCAAUCACUAACCA
CACGGGCCAGGUAAAAAGAUU

Hsa miR34c 2 Copy Mature Sequence

AAUCACUAACCACACGGGCCAGGAAUCACUAACCACACGGGCCAGG

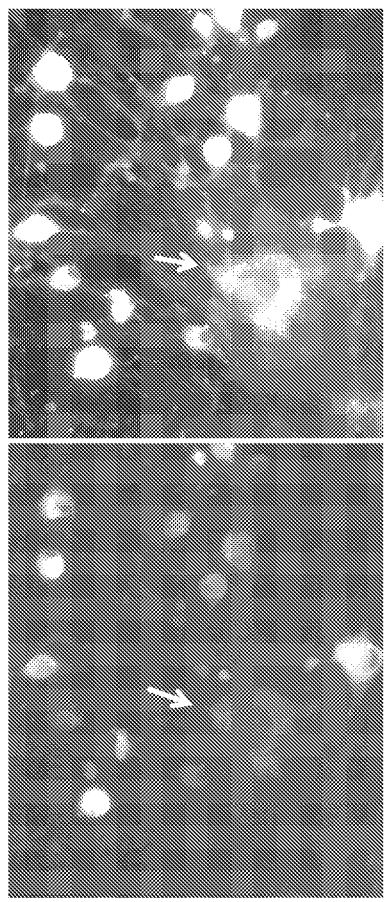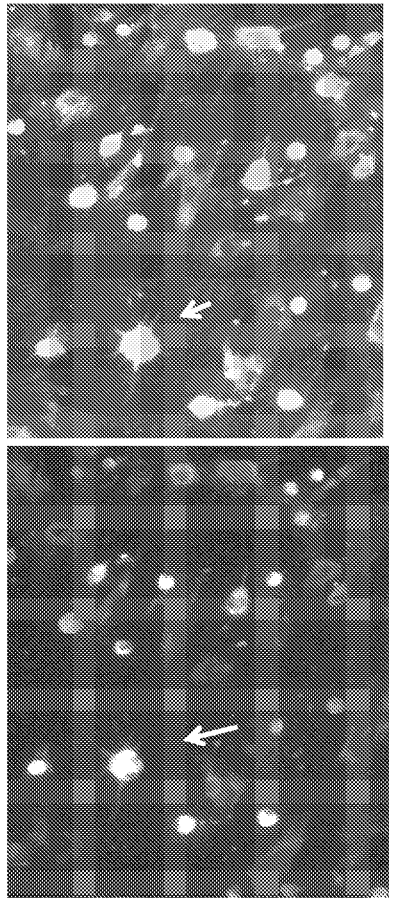
FIG. 34A FIG. 34B FIG. 34C FIG. 34D FIG. 34E FIG. 34F

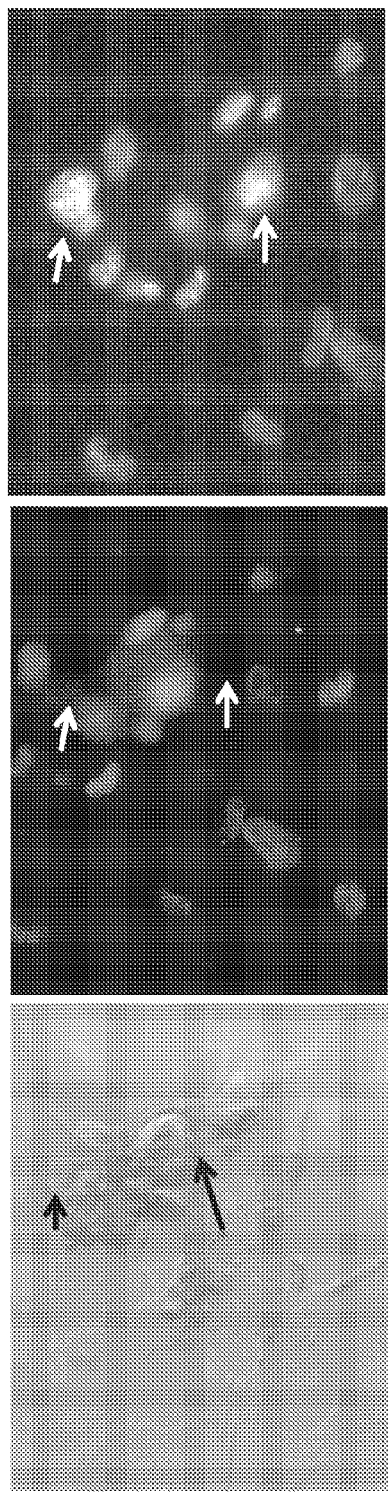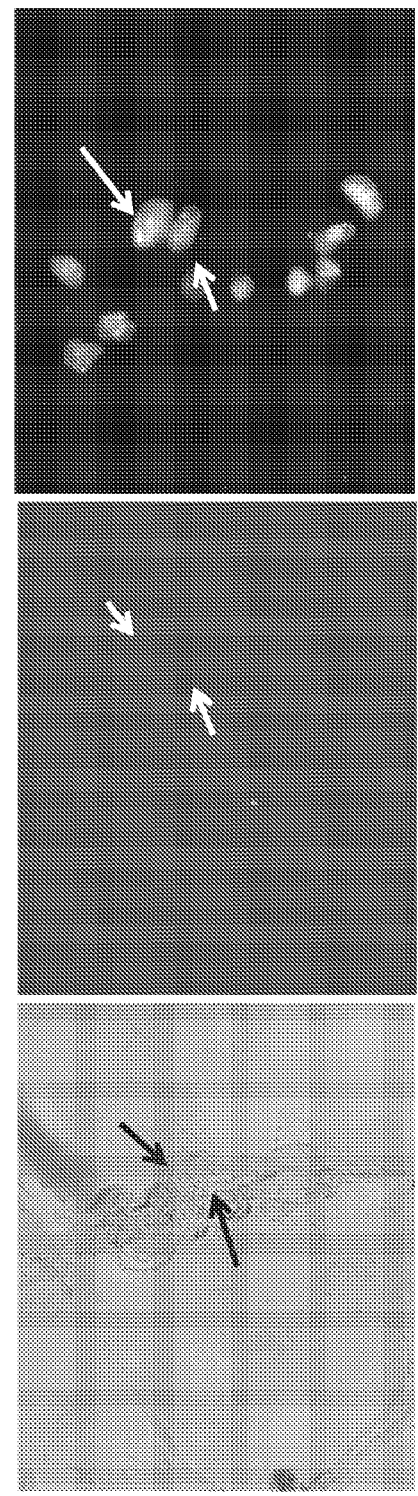

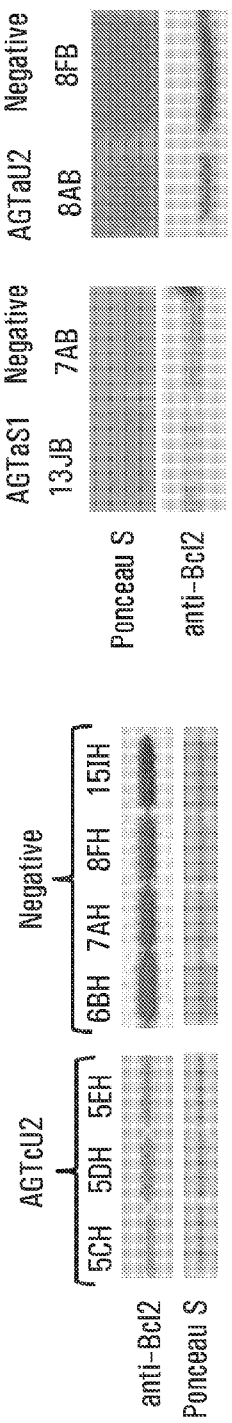
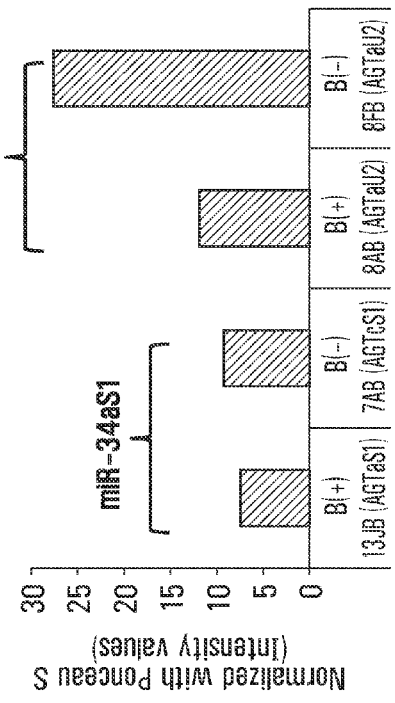
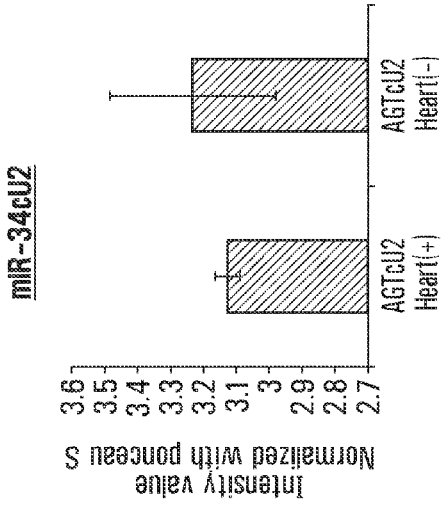
FIG. 39A
FIG. 39B
FIG. 39C
FIG. 39D

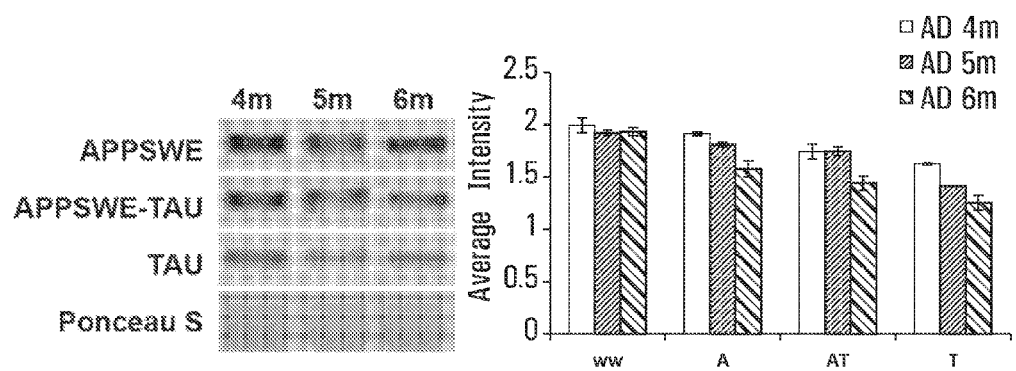
FIG. 44A
FIG. 44B
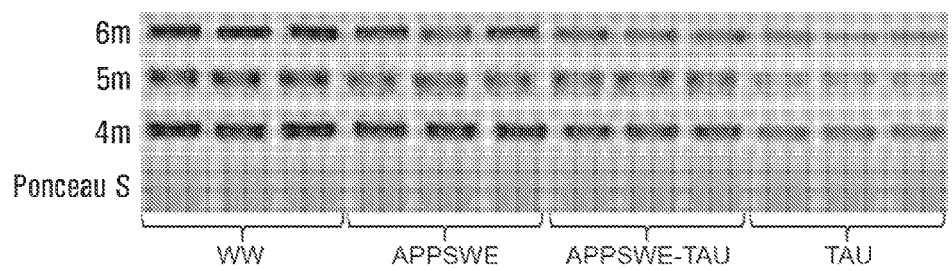
FIG. 44C
| Groups | AD-4m* | AD-5m* | AD-6m* |
|---|---|---|---|
| ww Vs. A | 0.0829 | 0.0014 | 0.0989 |
| ww Vs. AT | 0.0003 | 0.0008 | 0.0019 |
| ww Vs. T | 0.0002 | 0.0002 | 0.0003 |
| A Vs. AT | 0.0037 | 0.0336 | 0.0282 |
| A Vs.T | 0.0001 | 0.0001 | 0.0002 |
| AT Vs. T | 0.0263 | 0.0005 | 0.0066 |
AT=Amyloid tau ($APP^{SWE}$-Tau)
T=Tau
WW=Wild.wild
A=Amyloid ($APP^{SWE}$)
FIG. 44D

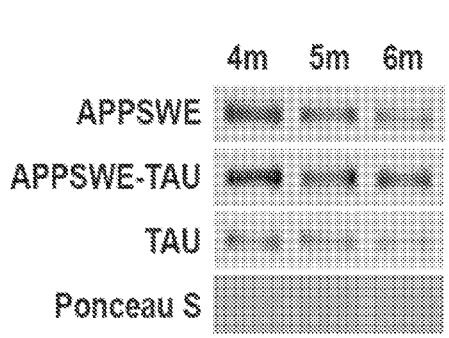
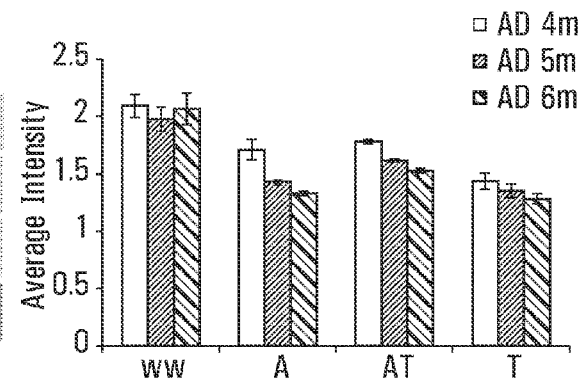
FIG. 45A
FIG. 45B
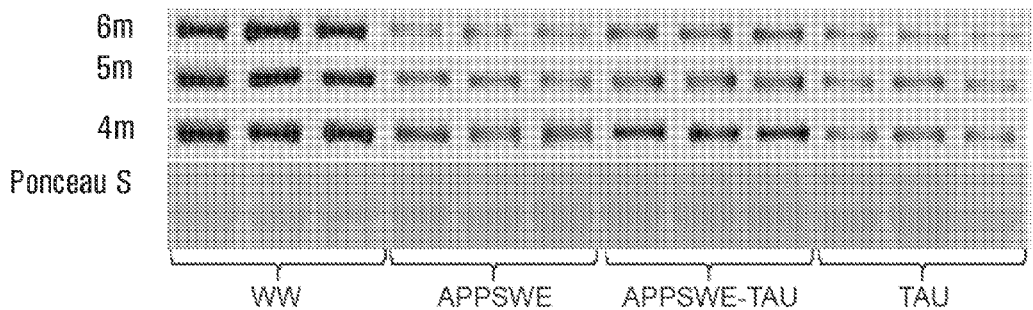
FIG. 45C
| Groups | AD-4m | AD-5m | AD-6m |
|---|---|---|---|
| ww Vs. A | 0.0002 | 0.00003 | 0.00001 |
| ww Vs. AT | 0.001 | 0.00008 | 0.00001 |
| ww Vs. T | 0.00005 | 0.00001 | 0.00001 |
| A Vs. AT | 0.3034 | 0.0049 | 0.011 |
| A Vs. T | 0.0022 | 0.1664 | 0.4473 |
| AT Vs. T | 0.0005 | 0.0006 | 0.0035 |
AT=Amyloid tau (APP$^{SWE}$-Tau)
T=Tau
WW=Wild.wild
A=Amyloid (APP$^{SWE}$)
FIG. 45D

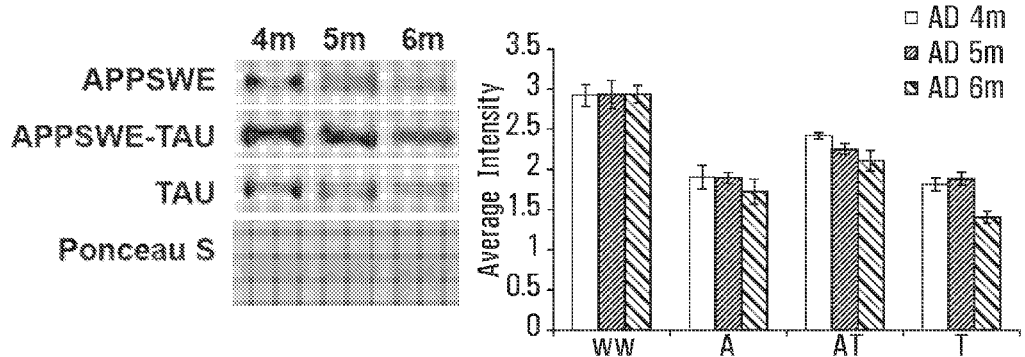
FIG. 46A
FIG. 46B
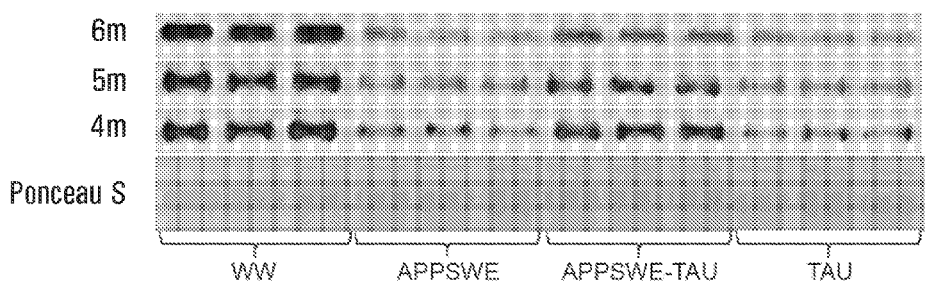
FIG. 46C
| Groups | AD-4m | AD-5m | AD-6m |
|---|---|---|---|
| ww Vs. A | 0.00003 | 0.00002 | 0.00001 |
| ww Vs. AT | 0.0005 | 0.00005 | 0.00003 |
| ww Vs. T | 0.00001 | 0.00002 | 0.00003 |
| A Vs. AT | 0.0004 | 0.0036 | 0.0046 |
| A Vs.T | 0.3454 | 0.896 | 0.0116 |
| AT Vs. T | 0.0001 | 0.0029 | 0.00009 |
AT=Amyloid tau ($APP^{SWE}$-Tau)
T=Tau
WW=Wild.wild
A=Amyloid ($APP^{SWE}$)
FIG. 46D

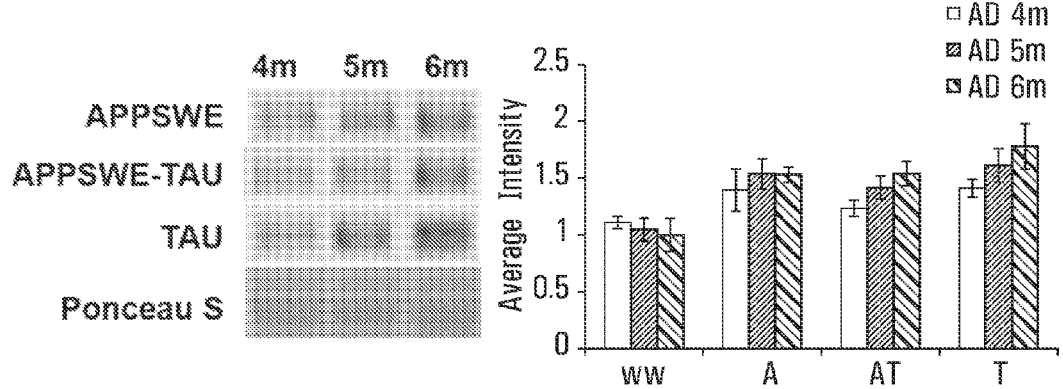
FIG. 47A    FIG. 47B
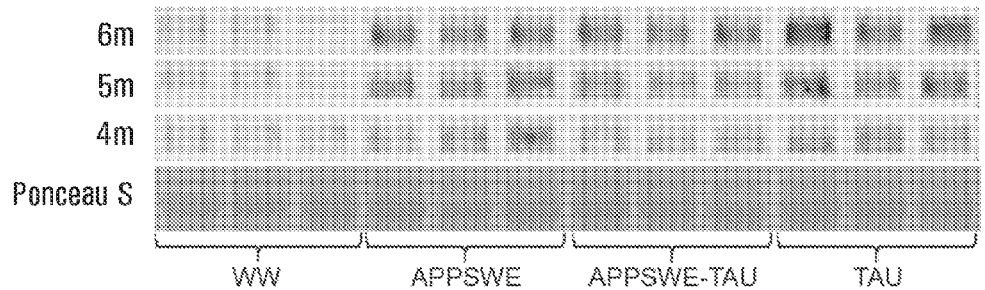
FIG. 47C
| Groups | AD-4m | AD-5m | AD-6m |
|---|---|---|---|
| ww Vs. A | 0.0139 | 0.0011 | 0.0015 |
| ww Vs. AT | 0.2112 | 0.006 | 0.0014 |
| ww Vs. T | 0.0102 | 0.0004 | 0.0001 |
| A Vs. AT | 0.1136 | 0.2587 | 0.9477 |
| A Vs. T | 0.8432 | 0.4785 | 0.0624 |
| AT Vs. T | 0.083 | 0.0857 | 0.0693 |
FIG. 47D
| Fold Change | | | |
|---|---|---|---|
| Cdk4 | AD-4m | AD-5m | AD-6m |
| ww Vs. A | 1.263321 | 1.488313 | 1.559802 |
| ww Vs. AT | 1.114015 | 1.360299 | 1.570612 |
| ww Vs. T | 1.274809 | 1.547362 | 1.803879 |
FIG. 47E

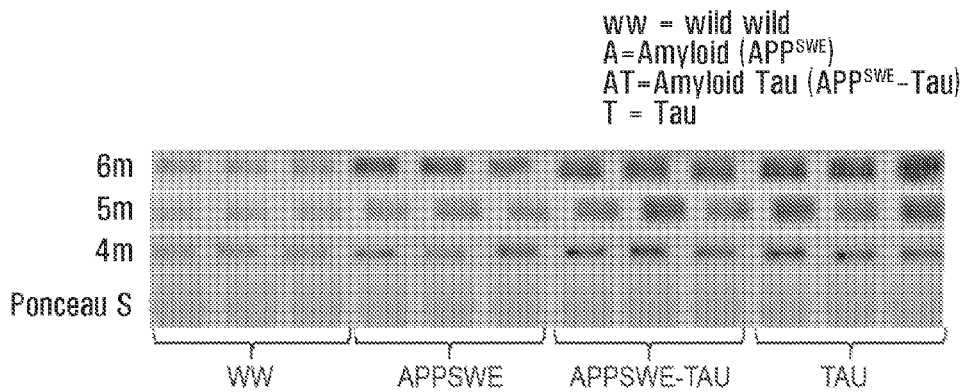
FIG. 48A
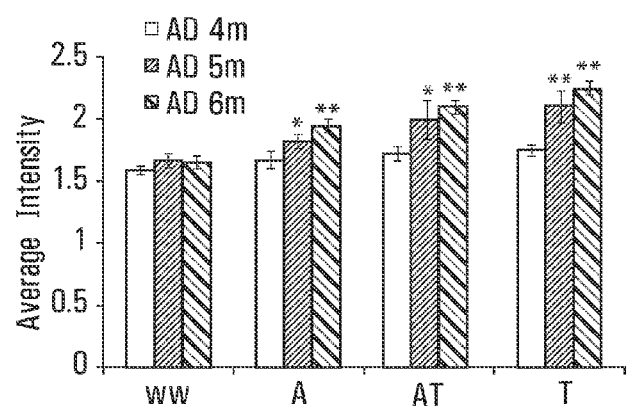
FIG. 48B
| Groups | AD-4m | AD-5m | AD-6m |
|---|---|---|---|
| ww Vs. A | 0.0975 | 0.1138 | 0.0003 |
| ww Vs. AT | 0.0137 | 0.0059 | 0.0001 |
| ww Vs. T | 0.005 | 0.0011 | 0.0001 |
| A Vs. AT | 0.2405 | 0.0888 | 0.0098 |
| A Vs. T | 0.086 | 0.0139 | 0.0002 |
| AT Vs. T | 0.5103 | 0.2661 | 0.0179 |
FIG. 48C

TRANSGENIC MICE EXPRESSING MICRORNA34 THAT HAVE CELLS DISPLAYING INCREASED SENESCENCE AND APOPTOSIS

CROSS-REFERENCE TO RELATED APPLICATIONS

This application is the National Stage of International Application No. PCT/US2013/021165, filed Jan. 11, 2013, which claims the benefit of and priority to U.S. Provisional Application No. 61/586,291, filed Jan. 13, 2012; U.S. Provisional Application No. 61/586,361, filed Jan. 13, 2012; and U.S. Provisional Application No. 61/636,477, filed Apr. 20, 2012, the entireties of which applications are incorporated herein by reference for any and all purposes.

STATEMENT OF FUNDED RESEARCH

This invention was made with an award from the Kentucky Cabinet for Economic Development, Department of Commercialization and Innovation, under Grant Agreement KSTC-184-512-11-110 with the Kentucky Science and Technology Corporation.

FIELD OF THE INVENTION

This application relates to non-human animal model for accelerating aging and/or age-related symptom, and to the use thereof.

BACKGROUND

Animal models have been used to study accelerated aging, accelerated senescence, premature aging, premature senescence, and progeria-like syndromes. These models may be grouped into four general classes: (1) experimentally induced models, (2) gene-modified models, (3) selection models, and (4) spontaneous models. There has been much debate over the connection between accelerated aging and disease status in animal models. Investigators interested in the basic mechanisms of normal aging have had to be prudent in their choice of animal models because early diseases leading to reduced life spans usually result from certain defects unrelated to mechanisms associated with normal aging.

Age-related diseases (or symptoms) are complications that generally arise from senescence. Non-limiting examples of age-related diseases (or symptoms) are, for example, cardiovascular disease, heart dysfunction, auditory function loss, anemia, cancer, arthritis, cataracts, osteoporosis, type 2 diabetes, hypertension, neurodegeneration (e.g., Alzheimer's disease (AD), and the like), increased presence of apoptotic markers, loss of bone mass, etc. Generally, the incidence of these age-related diseases (or symptoms) increases rapidly with aging (e.g., increases exponentially with age, in the case of cancer).

An animal model for accelerated aging has been described in the art. The senescence-accelerated-prone mouse strain 8 (SAMP8) [55, 176-180] have shorter median life spans of 10-12 months, approximate 40 to 50% of that of other laboratory mouse strains, such as C57/B6. This animal model for accelerated aging also exhibits age-related symptoms, such as accelerated deterioration of learning and memory, with immunoreactive AB-containing granules, Tau hyperphosphorylation, and other features such as neuronal cell loss, which are characteristic of Alzheimer's disease pathogenesis. SAMP8 may also show premature old age condition, i.e., loss of hair, hair coat not smooth with yellowish tint, and significant decrease of mobility and food intake. However, the molecular basis for the SAMP8 age-related symptoms remains unclear. The use of these animal models for selecting candidate compounds for treating, delaying or preventing accelerated aging and/or an age-associated symptom, such as AD, remains unsatisfactory.

Animal models for age-related diseases (or symptoms) have also been described in the art. The transgenic APP$^{swe}$ mouse [172], an animal model for AD, carries a transgene capable of expressing the human β-amyloid (Aβ) precursor polypeptide swe mutant and produces amyloid plaques in the animal brain. The transgenic Tau-mutant mouse [173], an animal model for AD, carries a transgene capable of expressing the Tau P301 mutant and produces neurofibrillary tangles. The double transgenic APP$^{swe}$+Tau mouse [174], an animal model for AD, carries a transgene capable of expressing both mutants. AD patients are generally classified in two broad categories: "sporadic" AD cases and "early-onset" AD cases. Victims that manifest AD symptoms at ages above 65, with increasing risk through the 70's and 80's, are classified as sporadic AD cases. Sporadic AD cases represent about 95% of total AD victim population, and are believed to not be genetically inherited, although some genes may act as risk factors. Victims that manifest AD symptoms at ages younger than 65 are classified as early-onset AD cases. Early-onset AD cases represent about 5% of total AD victim population, and may have a familial history of this disease. The AD familial cases, some 1% of the total AD victim population, exhibit genetic mutations for amyloid precursor polypeptide on chromosome 21, for Presenilin 1 polypeptide on chromosome 14, and/or for Presenilin 2 polypeptide on chromosome 1. Most of the transgenic animal strains developed as animal models for AD are thus based on gene mutations discovered in early-onset familial AD. Early-onset familial AD models are currently used in drug efficacy tests and vaccine development [Cruts M, Van Broeckhoven C. (1998) Ann Med 30: 560-565; Ruis J. (2008) Rev. Infirm. 143: 14-15; Hsiao K, et al. (1996) Science 274:99-102]. However, the use of these animal models for selecting candidate compounds for treating, delaying or preventing accelerated aging and/or an age-associated symptom, such as sporadic AD, remains unsatisfactory.

SUMMARY OF THE INVENTION

In one broad non-limiting aspect, the invention relates to a transgenic, non-human animal model for accelerated aging and/or age-related symptom, recombinant nucleic acid molecules, cells and methods that can be used to make such animal model and cells, methods of using the animal model and cells, to descendants of the transgenic non-human animal, obtained by breeding with the same or with another phenotype, and to a cell line or primary cell culture or to an organotypic brain slice culture, derived from the transgenic non-human animal or its descendants.

In another broad non-limiting aspect, the present invention relates to a recombinant nucleic acid molecule comprising a promoter operably linked to a heterologous nucleic acid molecule comprising the microRNA sequence selected from miR-34a, miR-34c, or a combination thereof.

In another broad non-limiting aspect, the present invention relates to a host cell comprising the recombinant nucleic acid molecule described herein.

In another broad non-limiting aspect, the present invention relates to a method of making a non-human transgenic animal model for accelerated aging and/or age-related symptom. The method comprises introducing a recombinant nucleic acid as described herein into an egg cell or embryonic cell of a non-human embryo, implanting the egg or embryonic cell into a compatible female host, and raising the egg or embryonic cell to viability in the female host.

In another broad non-limiting aspect, the present invention relates to a non-human transgenic animal or progeny thereof, whose genome comprises a promoter construct operably linked to a heterologous nucleic acid molecule comprising the microRNA sequence selected from miR-34a, miR-34c, or a combination thereof. The non-human transgenic animal or progeny thereof exhibits accelerated aging and/or an age-related symptom.

In another broad non-limiting aspect, the present invention relates to a method for selecting a candidate therapeutic compound for treating, delaying or preventing accelerated aging and/or an age-related symptom. The method comprises causing the herein described non-human transgenic animal model for accelerated aging and/or age-related symptom, or progeny thereof to contact with a compound; causing a determination of a level of a circulating microRNA selected from miR-34a and miR-34c, and/or a circulating level of a target polypeptide thereof; obtaining information that is indicative of whether the compound is a candidate therapeutic compound for treating, delaying or preventing accelerated aging and/or an age-associated symptom, the information being obtained from a comparison of the level of the respective circulating microRNA and/or polypeptide target thereof in presence of the compound to a reference level, and selecting the candidate therapeutic compound at least partly based on the information.

In another broad non-limiting aspect, the present invention relates to a method for use in connection with a process for selecting a candidate therapeutic compound for treating, delaying or preventing accelerated aging and/or an age-related symptom. The method comprises processing a sample from the herein described non-human transgenic animal model for accelerated aging and/or age-related symptom, or progeny thereof, for determining a level of a circulating microRNA selected from miR-34a and miR-34c, and/or a circulating level of a target polypeptide thereof, where the non-human transgenic animal or progeny thereof has been contacted with a compound. Processing the level of the respective circulating microRNA and/or polypeptide target thereof at least in part based on a reference level to derive information conveying whether the compound has therapeutic activity for treating, delaying or preventing accelerated aging and/or an age-associated symptom; and causing conveyance of the information to a recipient for selecting the candidate therapeutic compound at least partly based on the information.

In another broad non-limiting aspect, the present invention relates to a method for selecting a candidate therapeutic compound for treating, delaying or preventing accelerated aging and/or an age-associated symptom, the method comprising providing a host cell comprising the recombinant nucleic acid molecule described herein; determining the intracellular level of the microRNA and/or of a target polypeptide thereof after contacting the cell with a compound; processing the intracellular level at least in part based on a reference level to derive information conveying whether the compound has therapeutic activity for treating, delaying or preventing accelerated aging and/or an age-associated symptom; and selecting the candidate therapeutic compound at least partly based on this information.

In another broad non-limiting aspect, the present invention relates to a method for selecting a candidate therapeutic compound for treating, delaying or preventing accelerated aging and/or an age-associated symptom, comprising measuring an intracellular level of a microRNA selected from miR-34a and miR-34c or target polypeptide thereof in a host cell comprising the recombinant nucleic acid molecule described herein, said level being a first level; contacting the cell with a compound; measuring the intracellular level of said microRNA or target polypeptide thereof after the contacting step, said level being a second level; processing the second level at least in part based on the first level to derive information conveying whether the compound has therapeutic activity for treating, delaying or preventing accelerated aging and/or an age-associated symptom; and selecting the candidate therapeutic compound at least partly based on this information.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

FIG. 7: GeneBank numbers for specific sequence information, and primers used for plasmid generation of the human ubiquitin (hUbi) promoter plasmid (A), and the mouse synapsin (mSyn1) promoter plasmid (B).

FIG. 8: GeneBank numbers for specific sequence information, and primers used for generation of the LacZ plasmid (A), human microRNA-33 scaffold plasmid (B), and human growth hormone poly-A plasmid (C).

FIG. 11: Schematic showing a non-limiting illustration of primer design for hsa-miR-34a Syn and miR-34a Ubi constructs.

FIG. 12: Schematic showing a non-limiting illustration of primer design for human miR-34c (hsa-miR34c) Syn and has-miR-34c Ubi constructs.

FIG. 13: Panel A-E show five different clones for the transgenic construct, and arrows point to the selected clone of each of the five constructs with the added restriction site sequences and sent for sequencing. The 122 bp are for the miR-34a band with added restriction sites and the 89 bp are for miR-34c, except for the 2-copy 34c construct. Bands were excised from the gel and ligated into either the Ubi plasmid or the mSyn plasmid.

FIG. 21: Genotyping primers for transgenic mice bracketing hsa-miR-34a. The hsa-miR-34a sequence is shown in bold.

FIG. 22: Genotyping primers for transgenic mice bracketing hsa-miR-34c. The hsa-miR-34c sequence is shown in bold.

FIG. 24: hUbi-LacZ-hsa-miR34c (AGTcU2). Panel A: Final clone (single arrow) used for pronuclear injection; backbone is shown by the double arrow; Panel B: Founder mice with positive genotyped band (arrow) positive mice mated with negative mice; Panel C: F1 mating of positive siblings all show positive bands.

FIG. 27: mSyn1-LacZ-hsa-miR34c/miR-34c (AGTcS1) Panel A: Final clone (single arrow) used for pronuclear injection; backbone is shown by the double arrow; Panel B: Founder mice with positive genotyped band (arrow) positive mice mated with negative mice; Panel C: F1 mating of positive siblings all show positive bands.

FIG. 30: Sequence information of transgene of 34a and 34c with either Ubi- or Syn-promoter driven vector in precursor and mature form for the five transgenic lines shown in Table 1: (A) AGTaU2, (B) AGTcU2, (C) AGTaS1, (D) AGTcS2, and (E) AGTcS1.

FIG. 34: Apoptotic fibroblasts in 0.05% serum-containing medium for 24 hours are positive for LacZ trangene expression and beta-galactosidase. (Arrows point to apoptotic senescent fibroblasts; Panels A & D, phase contrast; Panels B & E, LacZ Staining, and Panels C & F, beta-galactosidase staining).

FIG. 35: Panels A and D show phase contrast images of apoptotic fibroblasts in 0.05% serum-containing medium for 24 hours, with weak or no Bcl2 staining (Panels B & E) and condensed nuclei by DAPI staining (Panels C & F). (Arrows point to nuclei with either weak or no Bcl2 staining and apoptotic condensed nuclear morphology.)

FIG. 36: Western blotting of SIRT1 abundance in two strains of transgenic mouse mutants: Panel A. AGTcU2 with Ubiquitin (U) promoter, for global expression of miR-34c; and Panel B, AGTcS1 with mSyn promoter and two copies of miR-34c for brain-specific expression. Numbers denote individual transgenic mice, either positive for the specific mutant transgene expression, or negative, showing no positive genotype bands. For brain samples, the loading control was actin; for heart specimens, a specific band of the same intensity was used as the loading control.

FIG. 39: Western blotting analysis of Bcl2 levels in three transgenic mouse strains: Panel A (gel images) and Panel B (histographs) show band intensities in heart samples of AGTcU2 mice, with miR-34c expression driven by the Ubiquitin promoter. Panel C and D are gel images (C) and histographs of band intensities (D) for AGTaS1, with mSyn promoter-driven, brain-specific miR-34a expression, and AGTaU2 for Ubiquitin-driven, global miR-34a expression.

FIG. 44: Age-dependent levels of Bcl-2 in plasma samples of AD-transgenic mice assayed by Western blot analysis in age groups from 4 to 6 months (m). (A) Bcl-2 level normalized with selected Ponceau S stained band. (B) Histograms presenting average densitometric values from the western blot in (A), where the histogram represents Mean±SD; and n=3. (C) Bcl-2 level normalized with selected Ponceau S stained band, three different mice used from each selected age group from 4 to 6 months. (D) Statistical analysis of the western blot results. The decrease is significant where p-value<0.05.

FIG. 45: Age-dependent levels of Onecut2 in plasma samples of AD-transgenic mice assayed by Western blot analysis of onecut2 expression in age groups from 4 to 6 months (m). (A) Onecut2 expression normalized with selected Ponceau S stained band, showing one band per group and constant levels for all samples used. (B) Histograms presenting average densitometric values from the western blot in (A), where the histogram represents Mean±SD; and n=3. (C) Onecut2 level normalized with selected Ponceau S stained band, three different mice used from each selected age group from 4 to 6 months. (D) Statistical analysis of the western blot results. The decrease is significant where p-value<0.05.

FIG. 46: Age-dependent levels of Presenilin 1 (PS1) in plasma samples of AD-transgenic mice assayed by Western blot analysis of PS1 expression in age groups from 4 to 6 months (m). (A) PS1 expression normalized with selected Ponceau S stained band, showing one band per group and constant levels for all samples used. (B) Histograms presenting average densitometric values from the western blot in (A), where the histogram represents Mean±SD; and n=3. (C) PS1 level normalized with selected Ponceau S stained band, three different mice used from each selected age group from 4 to 6 months. (D) Statistical analysis of the western blot results. The decrease is significant where p-value<0.05.

FIG. 47: Age-dependent levels of Cdk4 in plasma samples of AD-transgenic mice assayed by Western blot analysis in age groups from 4 to 6 months (m). (A) Cdk4 level normalized with selected Ponceau S stained band. (B) Histograms presenting average densitometric values from the western blot in (A), where the histogram represents Mean±SD; and n=3. (C) Cdk4 level normalized with selected Ponceau S stained band, three different mice used from each selected age group from 4 to 6 months. (D) Statistical analysis of the western blot results. The increase is significant where p-value<0.05. (E) Fold change is shown.

FIG. 48: Age-dependent levels of Aβ-42 in plasma samples of AD-transgenic mice assayed by Western blot analysis in age groups from 4 to 6 months (m). (A) Aβ-42 level normalized with selected Ponceau S stained band. (B) Histograms presenting average densitometric values from the western blot in (A), where the histogram represents Mean±SD; and n=3. (C) Statistical analysis of the western blot results. The increase is significant where p-value<0.05.

DETAILED DESCRIPTION OF EMBODIMENTS

Figure 1:
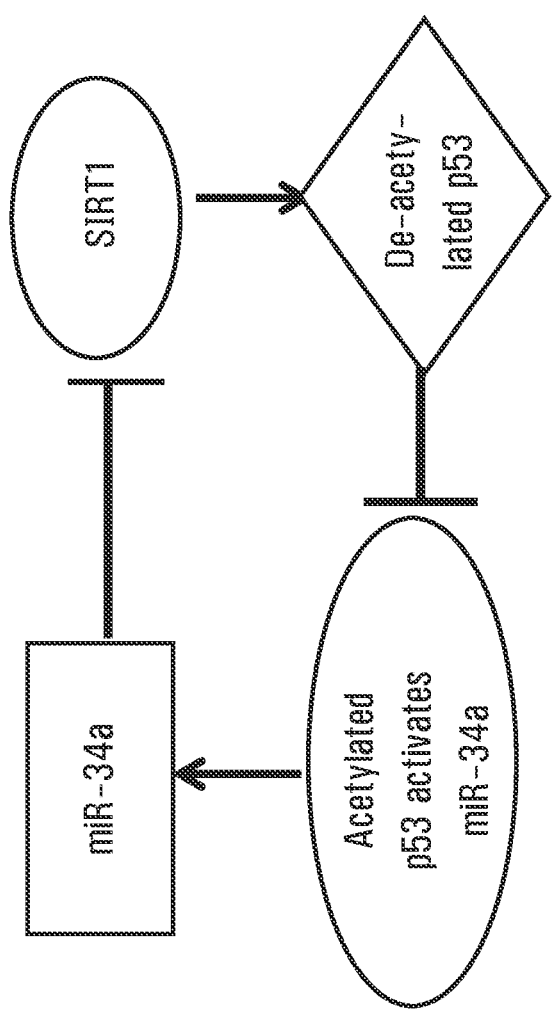
FIG. 1: Schematic showing a non-limiting illustration that proposes a working model for p53, miR-34a, and SIRT1 feedback loop.

The present inventor has discovered that a subject which has accelerated aging and/or an age-associated disease (or symptom) exhibits an increased level of a microRNA (miRNA) selected from miR-34a and miR-34c and a decreased level of a polypeptide encoded by an mRNA which is a target of the microRNA (hereinafter referred as "target polypeptide thereof") relative to the respective levels of microRNA and target polypeptide thereof in a control subject. This different level is detectable either in a cell, a tissue or as a circulating level in a biological sample.

The present inventor therefore prepared transgenic non-human animals which comprise a recombinant nucleic acid molecule (a transgene) capable of expressing such microRNA. These transgenic non-human animals surprisingly and unexpectedly exhibit at a young age increased apoptosis rates, which are generally seen in elderly animals, and cell cultures derived therefrom exhibit accelerated senescence phenotype. The early presentation of senescence phenotype and increased apoptosis rates are demonstrated for example, by accelerated fibroblast cell death. These transgenic non-human animals may thus be useful as models for accelerated aging and/or an age-related disease (or symptom).

In one non-limiting embodiment, these transgenic non-human animals may be useful for selecting a candidate therapeutic compound for treating, delaying or preventing accelerated aging and/or an age-related symptom, for example for a neurodegenerative disease, including strokes and Alzheimer's disease, in spinal cord injury, as well as a cardiovascular disease, in particular myocardial infarction, or for example to deter the loss of neuronal survival in brain specific strains, and the loss of cardiomyocytes in system-wide strains during reperfusion injury damage, and the like.

In one non-limiting embodiment, the herein described recombinant nucleic acid molecule comprises a nucleic acid molecule having a microRNA sequence, where the sequence can independently be one from a microRNA precursor sequence, a pro-microRNA sequence, a mature sequence, or any combinations thereof.

In one non-limiting embodiment, the herein described promoter is a brain specific promoter.

In one non-limiting embodiment, the herein described promoter is a systemic promoter.

In one non-limiting embodiment, the herein described systemic promoter is the ubiquitin promoter. The person skilled in the art will however be able to use an alternative promoter (e.g., the beta-actin promoter) having the same end result without departing from the present invention.

In one non-limiting embodiment, the herein described brain specific promoter is the synapsin promoter. The person skilled in the art will however be able to use an alternative promoter (e.g., the platelet-derived growth factor β-chain (PDGF-β) promoter) having the same end result without departing from the present invention.

In one non-limiting embodiment, the herein described circulating target polypeptide is selected from a polypeptide functionally related to apoptosis (e.g., Bcl2, etc.), to the synaptosis pathway (e.g., PS1, SIRT1, etc.), to the homeo-box pathway (Onecut2, etc.), and any combinations thereof. The person skilled in the art will however be able to select a suitable circulating target polypeptide without departing from the present invention.

In another non-limiting embodiment, the herein described circulating target polypeptide is selected from Onecut2, Prenisilin1 (PS1 or Psen1), SIRT1, Cdk4, Bcl2, and any combinations thereof. The person skilled in the art will however be able to select a suitable circulating target polypeptide without departing from the present invention.

In one non-limiting embodiment, the herein described method can be performed in vivo, ex vivo or in vitro. An in vitro or ex vivo method can be performed using, for example, a biological sample from or a part of the herein described transgenic non-human animal or progeny thereof (e.g. plasma, cell culture, and the like).

In one non-limiting embodiment, the herein described method may employ, for example, a dipstick, a membrane, a chip, a disk, a test strip, a filter, a microsphere, a slide, a multi-well plate, an optical fiber, and the like, or any other variant available to the person skilled in the art without departing from the invention.

In one non-limiting embodiment, cell cultures may be derived from the transgenic non-human animal of the invention. The cell culture may be a primary cell culture, such as neuronal lineage cell culture (e.g., hippocampal cells, cortex cells, etc.), fibroblasts or cardiomyocytes lineage. The cell culture may also be immortalized.

In one non-limiting embodiment, a fibroblast cell culture may also be reprogrammed as induced pluripotent stem cells (iPS). iPS cells are a type of pluripotent stem cell artificially derived from a non-pluripotent cell—typically an adult somatic cell, such as fibroblasts—by inducing a "forced" expression of specific genes. Transfected genes may include Oct-3/4, SOX2, c-Myc, and Klf4. The iPS cells derived from fibroblasts of the transgenic non-human animal of the invention could give rise to functional neuronal stem or cardiomyocyte stem lineage cell types, as well as other related cell types. Methods and materials for reprogramming cells into iPS are known or available to the person skilled in the art.

Animals that would be particularly useful as the herein described transgenic non-human animals are generally those which are easily bred, raised and readily manipulated genetically and biochemically. Such animals include, but without being limited thereto, the mouse, rat, gerbil, rabbit, hamster and guinea pig. In one non-limiting embodiment, the herein described transgenic non-human animal is a rodent. In yet another non-limiting embodiment, the herein described transgenic non-human animal is a mouse.

The transgenic non-human animals of the invention are produced by introducing transgenes into the germline of the non-human animal. Embryonal target cells at various developmental stages can be used to introduce the transgenes of the invention. Different methods are used depending on the stage of development of the embryonal target cell(s). Such methods include, but are not limited to, microinjection of zygotes, viral integration, and transformation of embryonic stem cells as described below.

1. Microinjection of zygotes. A zygote, which is a fertilized ovum that has not undergone pronuclei fusion or subsequent cell division, can be a target cell for microinjection of transgenic DNA sequences. The murine male pronucleus reaches a size of approximately 20 micrometers in diameter, a feature which allows for the reproducible injection of a solution containing transgenic DNA sequences. In most cases, the injected transgenic DNA sequences will be incorporated into the host animal's genome before the first cell division. Brinster et al., Proc. Natl. Acad. Sci. USA 82:4438, 1985. As a consequence, all cells of the resultant transgenic animals (founder animals) stably carry an incorporated transgene at a particular genetic locus, referred to as a transgenic allele. The transgenic allele demonstrates Mendelian inheritance, i.e., half of the offspring resulting from the cross of a transgenic animal with a non-transgenic animal will inherit the transgenic allele, in accordance with Mendel's rules of random assortment.

2. Viral integration. The developing embryos are cultured in vitro to the blastocyte developmental stage. The blastomeres may be infected with appropriate retroviruses. Jaenich, Proc. Natl. Acad. Sci. USA 73:1260. Infection of the blastomeres is enhanced by enzymatic removal of the zona pellucida. Transgenes are introduced via viral vectors which are typically replication-defective but which remain competent for integration of viral-associated DNA sequences, including transgenic DNA sequences linked to such viral sequences, into the host animal's genome. Transfection is easily and efficiently obtained by culture of blastomeres on a monolayer of cells producing the transgene-containing viral vector. Alternatively, infection may be performed using cells at a later developmental stage, such as blastocoeles. In any event, most transgenic founder animals produced by viral integration will be mosaics for the transgenic allele; that is, the transgene is incorporated into only a subset of all the cells that form the transgenic founder animals. Moreover, multiple viral integration events may occur in a single founder animal, generating multiple transgenic alleles which will segregate in future generations of offspring. Introduction of transgenes into germline cells by this method is possible but probably occurs at a low frequency. However, once a transgene has been introduced into germline cells by this method, offspring may be produced in which the transgenic allele is present in all of the animal's cells, i.e., in both somatic and germline cells.

3. Embryonal stem (ES). ES cells can be obtained from pre-implantation embryos that are cultured in vitro. Evans et al., Nature 292:154, 1981. ES cells that have been transformed with a transgene can be combined with an animal blastocyst, after which the ES cells colonize the embryo and contribute to the germline of the resulting animal (which is a chimera, i.e., composed of cells derived from two or more animals). Again, once a transgene has been introduced into germline cells by this method, offspring may be produced in which the transgenic allele is present in all of the animal's cells, i.e., in both somatic and germline cells.

Although the initial introduction of a transgene is a Lamarckian (non-Mendelian) event, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

As used herein, "transgene" generally means a DNA sequence which is partly or entirely heterologous (i.e., not present in nature) to the animal in which it is found, or which is homologous to an endogenous sequence (i.e., a sequence that is found in the animal in nature) and is inserted into the animal's genome at a location which differs from that of the naturally occurring sequence. There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. In vivo gene transfer techniques include transfection with viral (typically retroviral) vectors and viral coat protein-liposome mediated transfection (Dzau et al., Trends in Biotechnology, 11: 205-210 [1993]). The organism may not have had the nucleic acid originally, or may have had a different version of the nucleic acid. Transgenic animals which include one or more transgenes are within the scope of this invention.

As used herein, the term "compound" refers to any chemical entity, pharmaceutical, drug, and the like, that is suspected of having an impact on accelerated aging and/or an age-related disease (or symptom). Compounds comprise both known and potential therapeutic compounds. In one non-limiting embodiment, a compound can be considered to potentially positively affect accelerated aging and/or an age-related disease (or symptom) if it can be shown that it improves (brings closer to normal relatively to a control value) the circulating level of a microRNA. A compound is said to be "in a form suitable for administration", i.e., such that the compound is bio-available in the blood of the animal, when the compound may be administered to an animal by any desired route (e.g., oral, intravenous, subcutaneous, intrathecal, intraperitoneal, intramuscular, etc.) and the compound or its active metabolites appears in the blood of the animal in an active form. Following initial screening, a compound that appears substantially promising can be further evaluated if desired by techniques known in the art, e.g., but without being limited thereto, administering various concentrations of the compound to the transgenic animals described herein in order to determine an approximate therapeutic dosing range. Animal testing may be supplemented and confirmed by testing on human subjects if desired. The animal models described herein may allow the testing of a large number of compounds, by the methods described herein as well as other methods known in the art.

As used herein, "promoter" generally refers to an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor, and the like.

As used herein, "age-related disease (or symptom)" generally means "disease or condition of the elderly". Age-related disease (or symptom) does not refer to age-specific diseases, such as the childhood diseases chicken pox and measles. Nor should age-related disease (or symptom) be confused with premature aging diseases, all of which are genetic disorders. Non-limiting examples of age-related disease (or symptom) are for example, cardiovascular disease, heart dysfunction, auditory function loss, anemia, cancer, arthritis, cataracts, osteoporosis, type 2 diabetes, hypertension, neurodegeneration (e.g., Alzheimer's disease (AD), and the like), increased presence of apoptotic markers, loss of bone mass, etc. The incidence of these age-related diseases (or symptoms) increases rapidly with aging (e.g., increases exponentially with age, in the case of cancer).

As used herein, "recombinant nucleic acid molecule" refers to a molecule that results from the use of laboratory methods (molecular cloning) to bring together genetic material creating sequences that would not otherwise be found in a biological organism.

A first nucleic acid sequence is "operably-linked" with a second nucleic acid sequence when the first nucleic acid sequence is placed in a functional relationship with the second nucleic acid sequence. For instance, a promoter is operably-linked to a given sequence if the promoter affects the transcription or expression of the given sequence. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of a given sequence with which they are operably-linked. The expression of such a reporter gene may be measured on the transcriptional or translational level, e.g. by the amount of RNA or protein produced. RNA may be detected by for example Northern analysis or by the reverse transcriptase-polymerase chain reaction (RT-PCR) method (see for example Sambrook et al (1989) Molecular Cloning: A Laboratory Manual (second edition), Cold Spring Harbor Laboratory Press, Cold Spring Harbor, N.Y., USA). Protein levels may be detected either directly using affinity reagents (e.g. an antibody or fragment thereof [for methods, see for example Harlow, E. and Lane, D (1988) Antibodies: A Laboratory Manual, Cold Spring Harbor Laboratory Press, Cold Spring Harbor, N.Y.]; a ligand which binds the protein) or by other properties (e.g. fluorescence in the case of green fluorescent protein) or by measurement of the protein's activity, which may entail enzymatic activity to produce a detectable product (e.g. with altered spectroscopic properties) or a detectable phenotype (e.g. alterations in cell growth). Suitable reporter genes include but are not limited to chloramphenicol acetyltransferase, beta-D galactosidase, luciferase, or green fluorescent protein.

As used herein, "microRNA" is a small (e.g., 18-25 nucleotides in length), noncoding RNA that influences gene regulatory networks by post-transcriptional regulation of one or more specific messenger RNA (mRNA) target(s) via specific base-pairing interactions. This ability of microRNA to inhibit the production of its target mRNA/polypeptide(s) may result in the regulation of many types of cellular activities, such as but without being limited thereto, cell-fate determination, apoptosis, differentiation, and oncogenesis.

As used herein, "exosomes" are nanosize vesicles that are secreted by a wide range of mammalian cell types. Exosomes contain various molecular constituents of their cell of origin, including proteins and RNA. Although the exosomal protein composition varies with the cell and tissue of origin, most exosomes contain an evolutionary-conserved common set of protein molecules. Exosomes are also referred to in the art as microvesicles, epididimosomes, argosomes, exosome-like vesicles, microparticles, promininosomes, prostasomes, dexosomes, texosomes, dex, tex, archeosomes and oncosomes.

In general, a level which is "different" between two measurements (from different samples, or from the same sample but at different points in time, etc.) is one that is "upregulated" or "downregulated. In some embodiments, the difference in level can be measured qualitatively, such as via the visualization of the presence or absence of a signal. In other embodiments, the level can be determined quantitatively. In one non-limiting embodiment, the level may be compared to a diagnostic cut-off value, beyond which a skilled person is capable of determining the statistical significance of the level. In another non-limiting embodiment, a different level is present between two groups of measurements if, for example, the mean or median level in the respective groups is calculated to have a difference which is statistically significant. Common tests for statistical significance include, but without being limited thereto, t-test, ANOVA, Kruskal-Wallis, Wilcoxon, Mann-Whitney and odds ratio, and the like, which are known to the person skilled in the art.

In another non-limiting embodiment, a level which is "different" between two measurements may represent a different level of, e.g., at least 1.1, 1.2, 1.3, 1.4, 1.5, 1.6, 1.7, 1.8, 1.9, 2.0, 2.3, or more fold.

In another non-limiting embodiment, a level can be "upregulated", or "increased", or "augmented" in response to an administration of a compound or in response to a treatment, where the upregulation, or increase or augmentation is relative to a control level. This upregulation, or increase or augmentation can be, for example, an increase of about 5%, 10%, 20%, 30%, 40%, 50%, 60%, 70%, 90%, 100%, 200%, 300%, 500%, 1,000%, 5,000% or more when compared to the control level.

In another non-limiting embodiment, a level can be "downregulated", or "decreased" or "reduced" in response to an administration of a compound or in response to a treatment, where the downregulation, or decrease or reduction is relative to a control level. The downregulation, or decrease or reduction can be, for example, of about 99%, 95%, 90%, 80%, 70%, 60%, 50%, 40%, 30%, 20%, 10%, 1% or less when compared to the control level.

In another non-limiting embodiment, a "low" level can be a level that is statistically less than the level in a pool of measurements or from a control level. In another non-limiting embodiment, a "high" level can be a level that is statistically more than the level in a pool of measurements or from a control level.

In another non-limiting embodiment, the terms "determining," "measuring," "evaluating," "assessing," and "assaying," as used herein, generally refer to any form of measurement, and may include qualitative and/or quantitative measurements. In another non-limiting embodiment, when one starts from a biological sample, these terms generally include steps such as sample processing and transformation steps of the biological sample. Assessing may be relative or absolute.

In another non-limiting embodiment, the phrase "assessing the presence of" can include determining the amount of something present, as well as determining whether it is present or absent. The terms "determining," "measuring," and "assessing," and "assaying" are used herein interchangeably.

As used herein the term "treating" or "treatment" in reference to a disease or condition means a reduction in severity of one or more symptoms associated with the particular disease or condition. Therefore, "treating" or "treatment" does not necessarily mean a reduction in severity of all symptoms associated with the disease or condition, and does not necessarily mean a complete reduction in the severity of one or more symptoms associated with the disease or condition. "Treatment" or "treating", as used in this context, covers any treatment of a symptomatic condition in a mammal, particularly in a human, and may include: (a) diagnosing and preventing the disease or condition from occurring in a subject who may be predisposed but has not yet been diagnosed; (b) inhibiting the disease or condition, i.e., arresting its development; and (c) relieving the disease or condition, i.e., causing regression of the disease or condition. Similarly, the term "preventing" means prevention of the occurrence or onset of one or more symptoms associated with a particular disease or condition and does not necessarily mean the complete prevention of the condition.

As used herein, "modulation" of a microRNA level relates to a change in the level, such as a decrease or an increasing.

1. Biological Sample

As used herein, the expression "biological sample" generally refers to a sample obtained from a biological subject, including samples of biological tissue or fluid origin, obtained, reached, or collected in vivo or in situ.

As used herein, a "substantially cell free" biological sample is a biological fluid which has been processed, for instance but without being limited thereto, by centrifugation, sedimentation, cell sorting, and the like, in order to substantially remove cells, such that when one aims to detect the level of circulating molecule, this detected level substantially minimizes detection of intracellular molecules and molecules which would be released from cell lysis. In the particular case of fluids such as plasma and serum, these are generally presumed to be cell-free; however in the practical sense, particularly under conditions of routine clinical fractionation, plasma and serum may occasionally be contaminated by cells. Nonetheless, plasma and serum are considered for the purposes of this invention as "substantially cell free" biological samples.

As used herein a "circulating microRNA" and "circulating target polypeptide thereof" is a microRNA and target polypeptide thereof that are found in a substantially cell free biological sample.

In one non-limiting embodiment, the herein described biological sample is selected from, but without being limited thereto, blood and fractions thereof (i.e., blood serum, blood plasma or exosomes isolated therefrom), urine, excreta, semen, seminal fluid, seminal plasma, prostatic fluid, pre-ejaculatory fluid (Cowper's fluid), pleural effusion, tears, saliva, sputum, sweat, biopsy, ascites, amniotic fluid, lymph, vaginal secretions, endometrial secretions, gastrointestinal secretions, bronchial secretions, breast secretions, and the like. In the particular case of plasma, serum or exosomes isolated therefrom, these are generally presumed to be substantially cell free biological samples, however, in the practical sense, particularly under conditions of routine clinical fractionation, plasma, serum or exosomes isolated therefrom may occasionally be contaminated by cells. Nonetheless, plasma, serum or exosomes isolated therefrom are considered for the purposes of this invention as substantially cell free biological samples.

In one non-limiting embodiment, the herein described biological sample is selected from blood serum, blood plasma or exosomes isolated therefrom.

In one non-limiting embodiment, the herein described biological sample can be obtained by any known technique, for example by drawing, by non-invasive techniques, or from sample collections or from banks, etc.

In one non-limiting embodiment, the herein described biological sample can be a "fresh" or a frozen (stored) and subsequently thawed biological sample. For example, a frozen (stored) biological sample may be maintained at storage conditions of −20 to −70 degrees centigrade until thawed and used. For example, a "fresh" biological sample may be maintained at room temperature, refrigerated or maintained on ice until used.

In the specific example of sample for plasma, serum or exosomes isolated therefrom, blood can be drawn by standard methods into a collection recipient, such as a tube. In one non-limiting embodiment, the collection recipient can be made of siliconized glass. In one non-limiting embodiment, the blood can be drawn either without anticoagulant for preparation of serum, or with EDTA, sodium citrate, heparin, or similar anticoagulants for preparation of plasma.

In one non-limiting embodiment, the whole blood may be frozen or the plasma or serum can be fractionated from the whole blood prior to being frozen. In one non-limiting embodiment it may be advantageous to fractionate the plasma or serum or exosomes derived therefrom, from the whole blood prior to freezing because doing so may reduce the presence of cell lysis by-products subsequent to the freeze-thaw cycle, such as extraneous intracellular RNA and/or inhibitors of PCR such as porphyrins and hematin, and the like. The person skilled in the art will be able to select suitable methods and materials for doing such fractionation, for example use the ExoQuick™ or ExoQuick-TC™ kit (SBI—System Biosciences) to isolate exosomes, miRNeasy™ Serum/Plasma kit (QIAGEN) to isolate cell-free total RNA, including miRNA, plasma or serum may be fractionated from whole blood by centrifugation, using for instance centrifugation at about 300-800×g for about five to about ten minutes, or fractionated by other standard methods known in the art.

2. Detection and/or Quantification of microRNA

Generally, microRNA can be detected, and its level can be determined, using any of the techniques available to the person skilled in the art. For example, these techniques include, but are not limited thereto, different variants of the Northern blot methodology (see, e.g., Valoczi et al. 2004, Nucleic Acids Res. 2004 Dec. 14; 32(22):e175; Ramkissoon et al. 2006, Mol Cell Probes. 2006 February; 20(1):1-4), real-time PCR (see, e.g., Schmittgen et al. 2004 Nucleic Acids Res. 2004 Feb. 25; 32(4):e43; Chen et al. Nucleic Acids Res. 2005 Nov. 27; 33(20):e179; Raymond et al. 2005 RNA. November; 11(11):1737-44), confocal laser-induced fluorescence detection (Neely et al. Nat. Methods. 2006 January; 3(1):41-6), oligo-array-based technologies (see, e.g., Babak et al. RNA. 2004 November; 10(11):1813-9; Nelson et al. Nat. Methods. 2004 November; 1(2):155-61; or Thomson et al. Nat. Methods. 2004 October; 1(1):47-53), and the like.

The term "stringent assay conditions" generally refers to conditions that are compatible to produce binding pairs of nucleic acids, e.g., probes and target microRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or a "detectable moiety" in reference to a nucleic acid, generally refers to a composition that, when linked with a nucleic acid, renders the nucleic acid detectable, for example, by spectroscopic, photochemical, biochemical, immunochemical, or chemical means. Exemplary labels include but are not limited to radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

In one non-limiting embodiment, the herein described detection agent comprises a nucleic acid primer (or probe) having a sequence of 6-50, or 10-30, or 15-30, or 20-30 contiguous nucleotides of the microRNA and/or target mRNA thereof, including any length between the stated ranges. Such primer may be present, if desired, on a microarray.

Primers (or probes) are usually single-stranded for maximum efficiency in amplification/hybridization, but may alternatively be double-stranded. If double-stranded, the primers (or probes) are usually first treated to separate the strands before use; this denaturation step is typically done by heat, but may alternatively be carried out using alkali, followed by neutralization.

By way of a non-limiting example, the primers (or probes) for detecting a microRNA may be labeled, using labeling techniques that are known to one skilled in the art, to facilitate detection, including but not limited to radioisotope labels or fluorescent labels. The primers (or probes) can hybridize to nucleic acid molecules that are either or both strands of the double stranded nucleic acid molecule portion of the microRNA.

A "label" or a "detectable moiety" in reference to a detecting agent, in particular in the case of primers (or probes), generally refers to a compound that, when linked with at least one detecting agent, renders it detectable, for example, by spectroscopic, photochemical, biochemical, immunochemical, or chemical means. An example of a "label" or a "detectable moiety" includes but is not limited to radioactive isotopes, magnetic beads, metallic beads, colloidal particles, fluorescent dyes, enzymes, biotin, digoxigenin, haptens, and the like. In this context, "labeled" primers (or probe) includes primers (or probe) that are bound, either covalently, through a linker or a chemical bond, or noncovalently, through ionic bonds, van der Waals forces, electrostatic attractions, hydrophobic interactions, or hydrogen bonds, to a label such that the presence of the primers (or probe) can be detected by detecting the presence of the label bound to the primers (or probe).

A detectable label may be included in an amplification reaction. Suitable labels include fluorochromes, e.g., fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g., avidin, specific antibodies, etc., where the binding partner is conjugated to a detectable label. The label may be conjugated to one or both of the primers. Alternatively, the pool of nucleotides used in the amplification may be labeled, so as to incorporate the label into the amplification product. All of these and other labels are well known in the art and one can select corresponding suitable means for detecting such labels without departing from the present invention.

Hybridization primers (or probes) may be coupled to labels for detection. As with amplification primers, several methods and compositions for derivitizing oligonucleotides with reactive functionalities that permit the addition of a label are known in the art. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141, Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). In one embodiment, fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

Hybridization (e.g., formation of a nucleic acid duplex) refers to the ability of a strand of nucleic acid to join with a complementary strand via base pairing. Hybridization occurs when complementary nucleic acid sequences in the two nucleic acid strands contact one another under appropriate conditions.

Nucleic acid hybridization is affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringency conditions depend on the length and base composition of the nucleic acid, which can be determined by techniques well known in the art. Generally, stringency can be altered or controlled by, for example, manipulating temperature and salt concentration during hybridization and washing. For example, a combination of high temperature and low salt concentration increases stringency. Such conditions are known to those skilled in the art and can be found in, for example, Strauss, W. M. "Hybridization With Radioactive Probes," in Current Protocols in Molecular Biology 6.3.1-6.3.6, (John Wiley & Sons, N.Y. 2000). Both aqueous and nonaqueous conditions as described in the art can be used.

An example of stringent hybridization conditions is hybridization in 0.1×SSC (15 mM sodium chloride/1.5 mM sodium citrate) at 50° C. or higher. Another example of stringent hybridization conditions is hybridization overnight at 42° C. in 50% formamide, 1×SSC (150 mM NaCl, 15 mM sodium citrate), 50 mM sodium phosphate (pH 7.6), 5×Denhardt's solution, 10% (w/v) dextran sulfate, and 20 µg/ml denatured, sheared salmon sperm DNA, followed by washing in 0.1×SSC at about 65° C. Highly stringent conditions can include, for example, aqueous hybridization (e.g., free of formamide) in 6×SSC (where 20×SSC contains 3.0 M NaCl and 0.3 M sodium citrate), 1% (w/v) sodium dodecyl sulfate (SDS) at 65° C. for about 8 hours (or more), followed by one or more washes in 0.2×SSC, 0.1% SDS at 65° C.

Moderately stringent hybridization conditions permit a nucleic acid to bind a complementary nucleic acid that has at least about 60%, at least about 75%, at least about 85%, or greater than about 90% identity to the complementary nucleic acid. Stringency of hybridization is generally reduced by decreasing hybridization and washing temperatures, adding formamide to the hybridization buffer, or increasing salt concentration of the washing buffer, either individually or in combination. Moderately stringent conditions can include, for example, aqueous hybridization (e.g., free of formamide)

in 6×SSC, 1% (w/v) SDS at 65° C. for about 8 hours (or more), followed by one or more washes in 2×SSC, 0.1% SDS at room temperature. Another exemplary hybridization under moderate stringency comprises hybridization in 6×SSC, 5×Denhardt's reagent, 0.5% (w/v) SDS, and optionally 100 µg/ml sonicated salmon or herring sperm DNA, at about 42° C., followed by washing in 2×SSC, 0.1% (w/v) SDS at 65° C. Other permutations and possibilities will be readily apparent to those of ordinary skill in the art, and are considered as equivalents within the scope of the instant invention.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases are not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

In one non-limiting embodiment, substantially complementary nucleic acids have at least 50%, at least 60%, at least 70%, at least 80%, at least 90%, at least 95%, at least 98%, or at least 99% identical nucleotides.

The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

As used herein, a nucleic acid sequence "substantially identical" to a target sequence, e.g., a target sequence contained within the target microRNA, is a nucleic acid sequence which is identical to the target sequence, or which differs from the target sequence by one or more nucleotides.

Generally, real-time PCR can be done according to published protocols and variants thereof, which can be designed by the person skilled in the art without departing from the present invention. For one or more specific microRNA sequences in a sample, real time-PCR enables both detection and quantification. The quantity can be either an absolute number of copies or a relative amount, for example, relative amount can be when the resulting amount is normalized to a control RNA or added normalizing RNAs.

The real-time PCR procedure usually follows the following general principles.

In the illustrative example where one starts from a biological sample, one can proceed with total RNA extraction from the biological sample using, e.g., TRI Reagent™ (Molecular Research Centre, Inc.) or TRIzol™ reagent (Invitrogen) following the manufacturer's recommendations. RNA quality may be examined for instance on an Agilent 2100 Bioanalyzer with the RNA 6000 Nano Kits (Agilent, Germany) or by visual inspection of the 28S/18S ribosomal bands in an agarose gel. RNA quantity can be measured, for example, on a Nanodrop 1000 Spectrophotometer (Thermo Scientific, USA). Total RNA or a fraction thereof is then used for cDNA synthesis using reverse transcriptase enzyme and suitable reagents, e.g. buffers, dNTP, primers, etc., as described in several publications known to the person skilled in the art (see, e.g., Schmittgen et al. 2004 Nucleic Acids Res. 2004 Feb. 25; 32(4):e43; Chen et al. Nucleic Acids Res. 2005 Nov. 27; 33(20):e179; Raymond et al. 2005 RNA. November; 11(11):1737-44).

One can then proceed with the real-time PCR procedure following the general principles of polymerase chain reaction. Two common methods for detection of products in real-time PCR are: (1) non-specific fluorescent dyes that intercalate with any double-stranded DNA, and (2) sequence-specific DNA probes labelled with a fluorescent reporter which permits detection only after hybridization of the probe with its complementary DNA target.

To quantify the amount of target microRNA one can proceed with absolute or relative quantification. In one non-limiting embodiment, relative quantification gives the amount of the target microRNA relative to the amount of an RNA measured in the same sample or to a spiked-in control RNA. In another non-limiting embodiment, absolute quantification gives the exact number of target miRNA molecules by comparison with standards [see, e.g., Dhanasekaran et al. (2010 March). Immunol Methods. 354 (1-2): 34-9].

One can proceed along the following illustrative, but non-limiting lines:

Relative concentrations of DNA produced by the PCR reaction present during the exponential phase of the reaction can be determined by plotting fluorescence against cycle number on a logarithmic scale (so that an exponentially-increasing quantity will show as a straight line). A threshold for detection of fluorescence above background is determined. The cycle at which the fluorescence from a sample crosses the threshold is called the cycle threshold, $C_T$. The quantity of DNA theoretically doubles every cycle, during the exponential phase, and relative amounts of DNA can be calculated, e.g. a sample whose $C_T$ is 3 cycles earlier than another's has $2^3=8$ times more template. Since all sets of primers don't work equally well, one has to calculate the reaction efficiency first. Thus, by using this as the numeric base and the cycle difference $C_T$ as the exponent, the precise difference in starting template can be calculated (in previous example, if efficiency was 98%, then the sample would have $2(^{3*98\%})=(2^{98\%})^3=7.67$ times more template).

One can then obtain the $\Delta C_T = C_T$ target $- C_T$ reference, where the target is the miRNA of interest and the reference is the gene or miRNA used to normalize the experimental results. The $\Delta\Delta C_T$ values can also be calculated as follows.

Normalize each $\Delta C_T$ value to a particular $\Delta C_T$ value of an assay calibrator. $\Delta\Delta C_T=\Delta C_T$ test sample–$\Delta C_T$ calibrator sample. Calibrator samples are samples used as a basis for comparative expression results. The standard deviation of $\Delta\Delta C_T$ is the same as the standard deviation of $\Delta C_T$. Note: For samples with significant biological variability, one can calculate $1/\Delta C_T$ for both the test samples and the calibrator samples. In order to calculate the fold change assuming the efficiency of target and reference is close to 100%, one can proceed as follows. The fold difference in expression of test samples relative to the calibrator samples is expressed as: $2^{-\Delta\Delta C_T}$ with $\Delta\Delta C_T$–SD and $\Delta\Delta C_T$+SD. For the $\Delta\Delta C_T$ calculation to be valid, the amplification efficiencies of the target and the reference must be approximately equal. To determine if the two amplification reactions have the same PCR efficiency, one must look at how the $\Delta C_T$ varies with template dilutions. For example, one can proceed as follows: 1) Prepare at least 6-log dilutions range of the sample. The sample must express both the target and the reference. 2) Plot the log input amount of RNA vs. $\Delta C_T$ values to create a semi-log regression line. 3) If the absolute value of the slope is <0.1, the efficiencies of the target and reference are similar, and the $\Delta\Delta C_T$ calculation can be used for relative quantization of the target.

3. Detection and/or Quantification of Circulating Target Polypeptide

In one non-limiting aspect, the herein described method additionally or alternatively includes determining the level of a circulating target polypeptide and/or target polypeptide. This level can, if desired, then be used to establish a Target Polypeptide repression (TPR) index as described in U.S. provisional application 61/521,241 filed Aug. 8, 2011 in the name of Eugenia Wang, the entire contents of which are hereby incorporated by reference in their entirety.

Generally polypeptides can be detected and their level may be assayed using antibodies with commonly used methods known in the art such as, but without being limited thereto, Western blotting or enzyme-linked immunosorbent assay (ELISA). Western blotting typically begins with an electrophoresis step, where polypeptides from a biological sample of interest are separated on the basis of size and electromagnetic charge by sodium dodecyl sulfate-polyacrylamide gel electrophoresis (SDS-PAGE), according to standard methods known in the art. See, e.g., Sambrook et al., 3 Molecular cloning: a laboratory manual A8.40-A8.45 (2001) (describing various reagents and methods for electrophoresis of polypeptides by SDS-PAGE). The contents of the gel are then transferred to nitrocellulose, nylon, PVDF, or other membrane or filter suitable for fixation and Western blotting by standard methods also known in the art. The transfer may be by immersion, semi-dry blotting, or by other comparable methods known in the art. Next, the filters or membranes are fixed to prevent loss of the target polypeptides during the several steps of hybridization, washing, and staining typically included in Western blotting. Fixation may be accomplished by heat, cross-linking with ultraviolet light, or by other comparable methods known in the art. See, e.g., Sambrook et al., A8.52-A8.55 (describing various reagents and methods for immunoblotting and detection of antigen/antibody complexes).

Non-specific antibody binding sites on the fixed filter or membrane are generally blocked with buffered solutions (e.g., phosphate-buffered saline ("PBS") or the like) containing a blocking agent such as, for example, 0.5% (w/v) low-fat dry milk or 5% (w/v) bovine serum albumin (BSA). After blocking, the filter or membrane then undergoes primary antibody incubation. After primary antibody incubation, the filter or membrane is washed, and the presence of antibody-antigen complexes detected using a secondary antibody labeled with chromogenic, fluorogenic, or chemiluminescent means. Antibody-antigen complexes are then detected colorimetrically (e.g., with horseradish peroxidase and TMB), or by autoradiography (e.g., alkaline phosphatase). If detected colorimetrically, or by chemiluminescence, the amount of color of fluorescence may be measured using a luminometer, a spectrophotometer, or other similar instruments. If detected autoradiographically, the amount of bound antibody may be measured from the exposed x-ray film using a densitometer, or similar instrument. See, e.g., Sambrook et al., A8.52-A8.55.

Secondary antibodies used in Western blotting, whether polyclonal or monoclonal, may be labeled with a ligand (such as biotin) or a detectable marker (such as a fluorescent group or an enzyme) using conventional techniques. Suitable labels include fluorophores, chromophores, electron-dense reagents (e.g., silver or gold), enzymes, and ligands having specific binding partners. Enzymes such as horseradish peroxidase or alkaline phosphatase are typically detected by their activity. For example, horseradish peroxidase can be detected by its ability to convert tetramethylbenzidine (TMB) to a blue pigment, quantifiable with a spectrophotometer. Other suitable ligands and/or detectable markers include biotin and avidin or streptavidin, IgG and polypeptide A, and the numerous additional receptor-ligand couples known in the art. Other permutations and possibilities will be readily apparent to those of ordinary skill in the art, and are considered as equivalents within the scope of the instant invention.

Since serum/plasma contains 57-71% of serum albumin and 8-26% of gamma immunoglobulin (IgG), before polypeptide extraction, plasma samples may also be processed by standard commercially available kit to remove both of these polypeptide species. For example, combining an anti-human serum albumin cartridge and a polypeptide G cartridge, both albumin and IgG can be removed. This generally allows close to up to 90% efficiency. Kit containing both anti-HSA antibody and Polypeptide G affinity chromatography cartridges are available from QIAGEN. The plasma polypeptide specimens after processing this fashion can be processed for polypeptide concentration measurements by standard Bradford assays.

An ELISA typically begins with an antigen adsorption step, where the target antigen or antigens are adsorbed to the wells of a microtiter plate. See, e.g., Kierkegaard & Perry Laboratories, INC., Technical guide for ELISA 9-13 (2003). The most commonly used adsorption buffers for antibodies are 50 mM Carbonate, pH=9.6; 10 mM Tris-HCl, pH=8.5; and 10 mM PBS, pH=7.2. These buffers work well for many polypeptides. If the target antigens are not readily adsorbed to the surface of the microtiter plate, plates with surfaces modified or derivatized to permit covalent linkage of polypeptides to their surface by a variety of chemical means are widely available from commercial suppliers. Time and temperature are factors affecting the amount of polypeptide adsorbed.

Once the wells of a microtiter plate are coated with the desired antigen or antigens, they are typically washed with a blocking buffer to block non-specific antibody binding and to minimize false positive results. See, e.g., idem at 13-14 (discussing methods and reagents for blocking microtiter plates). Commonly used blocking agents are either polypeptide solutions, such as BSA (typically used at concentrations between 1% and 5% (w/v) in PBS, pH=7.0), non-fat dry milk, casein (the main polypeptide component of non-fat dry milk), or caseinate (a more soluble version of casein, produced by partial digestion with sodium hydroxide), normal serum (typically used at concentrations between 1% and 5% (v/v)), and gelatin (normally used at concentrations between 1% and 5% (w/v)), or non-ionic detergents, such as Tween-20™ and Triton X-100™.

Washing reagents are selected for their ability to disrupt low-affinity interactions between various reaction components that can affect the ability to detect specific antigen-antibody interactions. See, e.g., idem at 14-15 (discussing methods and reagents for washing microtiter plates). Wash solutions commonly contain a physiological buffer to prevent denaturation of antigens and their cognate antibodies, and to preserve enzyme activity. Buffers such as PBS, Tris-saline, or imidizole-buffered saline at neutral pH are widely used. Specific buffers are typically selected based on the method of detection to be employed in a particular assay. Wash buffers should also include non-ionic detergents such as Tween-20, Triton X-100, or the like, at concentrations of between 0.01% to 0.05% (v/v), in order to disrupt low-affinity, non-specific interactions between reaction components.

After the blocking step, the wells of the microtiter plate are typically washed. The adsorbed antigen then undergoes the primary antibody incubation, after which it is typically washed again. Antibody/antigen complexes are then detected using a secondary antibody labeled with chromogenic (e.g., horseradish peroxidase and TMB), fluorescent or chemiluminescent (e.g., alkaline phosphatase) means. See, e.g., idem at 15-21 (discussing antibody preparation and use, as well as commonly used detection molecules). The amount of color or fluorescence may be measured using a luminometer, a spectrophotometer, or other similar instruments. There are many common variations on the standard ELISA protocol, including competitive ELISA, sandwich ELISA, and numerous others. One of ordinary skill in the art will select the appropriate protocol to use, depending on the antigen to be detected, the source of antigen and/or primary antibody used in the assay, and any other relevant experimental parameters.

4. Methods for Screening Compounds

Through use of the herein described transgenic non-human animals, or progeny thereof, or cells derived therefrom, one can identify ligands or substrates that are capable of modulating phenomena associated with accelerated aging and/or age-related disease (or symptom). A wide variety of assays may be used for this purpose, including behavioural studies, determination of the localization of compounds after administration, immunoassays to detect disease markers, decrease in apoptosis of fibroblast cells following use of the compound, decrease in level of microRNA 34a and/or 34c following use of the compound, increase in level of target polypeptide following use of the compound, delay in senescence phenotype following use of the compound, reduction in apoptosis rates following use of the compound, and the like. Depending on the particular assay, whole animals may be used, or cells derived therefrom. Cells may be freshly isolated from an animal, or may be immortalized in culture.

Generally a plurality of assay mixtures may be performed in parallel with different compound concentrations to obtain a differential response to the various concentrations. Typically, one of these concentrations may serve as a negative control, i.e. at zero concentration or below the level of detection.

Candidate compounds encompass numerous chemical classes, though typically they are organic molecules, preferably small organic compounds having a molecular weight of more than 50 and less than about 2,500 daltons. Candidate compounds may comprise functional groups necessary for structural interaction with proteins, particularly hydrogen bonding, and may typically include at least an amine, carbonyl, hydroxyl or carboxyl group, preferably at least two of the functional chemical groups. The candidate compounds may comprise cyclical carbon or heterocyclic structures and/or aromatic or polyaromatic structures substituted with one or more of the above functional groups. Candidate compounds are also found among biomolecules including, but not limited to: peptides, saccharides, fatty acids, steroids, purines, pyrimidines, derivatives, structural analogs or combinations thereof.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

The cells may be dissociated, in the case of solid tissues, or tissue sections may be analyzed. Alternatively a lysate of the cells may be prepared.

For example, detection may utilize staining of cells or histological sections, performed in accordance with conventional methods. Antibodies of interest are added to the cell sample, and incubated for a period of time sufficient to allow binding to the epitope, usually at least about 10 minutes. The antibody may be labelled with radioisotopes, enzymes, fluorescers, chemiluminescers, or other labels for direct detection. Alternatively, a second stage antibody or reagent is used to amplify the signal. Such compounds are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

A number of assays are known in the art for determining the effect of a compound on animal behaviour and other phenomena associated with accelerated aging and/or age-related disease (or symptom). The subject animals may be used by themselves, or in combination with control animals. In the case of an assay for selecting a compound for treating, delaying or preventing AD, control animals may have, for example, a wild-type APP transgene that is not associated with AD.

The screen using the transgenic animals of the invention can employ any phenomena associated with accelerated aging and/or age-related disease (or symptom) that can be readily assessed in an animal model. The screening for accelerated aging and/or age-related disease (or symptom) can include assessment of phenomena including, but not limited to: 1) analysis of molecular markers, such as for example cardiac markers in myocardial infarction with or without reperfusion; 2) assessment behavioural symptoms associated with memory and learning; 3) detection of neurodegeneration characterized by progressive and irreversible differentiation of the limbic system, association neocortex, and basal forebrain (neurodegeneration can be measured by, for example, detection of synaptophysin expression in brain tissue) (see, e.g., Games et al. (1995) Nature 373:523-7), and the like. These phenomena may be assessed in the screening assays either singly or in any combination.

Methods for using transgenic animals in various screening assays, for example, for testing compounds for an effect on AD, are found in WO 12/004,322, WO 96/40896, WO 96/40895, and WO 95/11994.

5. Results

The following examples are intended to illustrate the present invention without limitation.

Plasmid Construction for Knock-in Overexpression of microRNA-34a (Tg-34a) or microRNA-34c (Tg-34c):

We used the precursor form for the mature miR-34a and miR-34c as transgenes to generate constructs for the transgenic mutants listed in Table 1.

| Construct name | Mouse strain name | Promoter | LacZ | miRNA | PolyA | Scaffolding |
| --- | --- | --- | --- | --- | --- | --- |
| AGT-Tg.001 | AGTaS1 | Mouse Syn | E. Coli K-12 strain | Hsa-34a | Human Growth Hormone | Human miR33 |
| AGT-Tg.002 | AGTaU2 | Human Ubiquitin C | | Hsa-34a | | |
| AGT-Tg.003 | AGTcS1 | Mouse Syn | | 2 copies of hsa-34c | | |
| AGT-Tg.004 | AGTcS2 | Mouse Syn | | Hsa-34c | | |
| AGT-Tg.005 | AGTcU2 | Human Ubiquitin C | | Hsa-34c | | |

Figure 6:
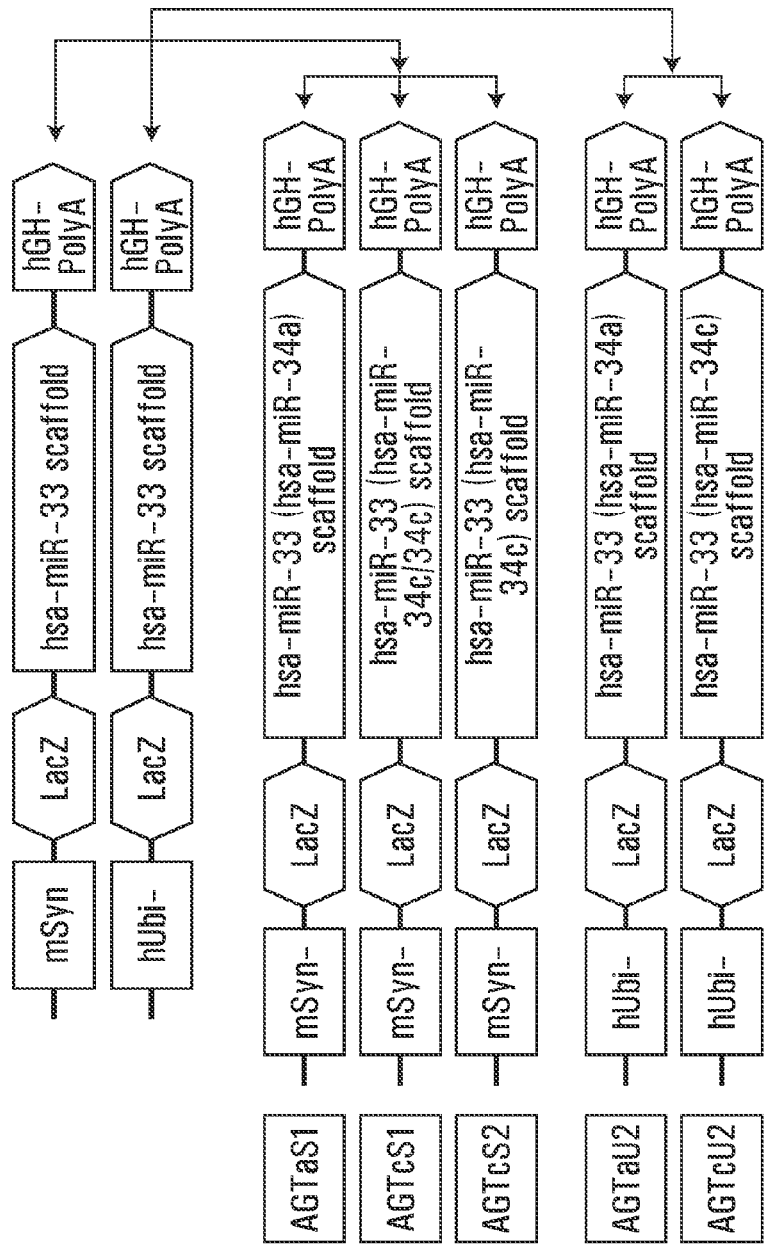
FIG. 6: Cloning strategy to generate two universal constructs: (Panel A), brain-specific expression mouse synapsin promoter (mSyn), and global expression by human ubiquitin-promoter (hUbi), with E. coli LacZ for transgene detection, followed by human microRNA-33 (hmiR-33) as the scaffold and human growth hormone poly A (hGH-PolyA). Specific transgenes, either miR-34a or miR-34c, were then Incorporated into the miR-33 backbone (Panel B) to generate the five mutant strains.
Figure 9:
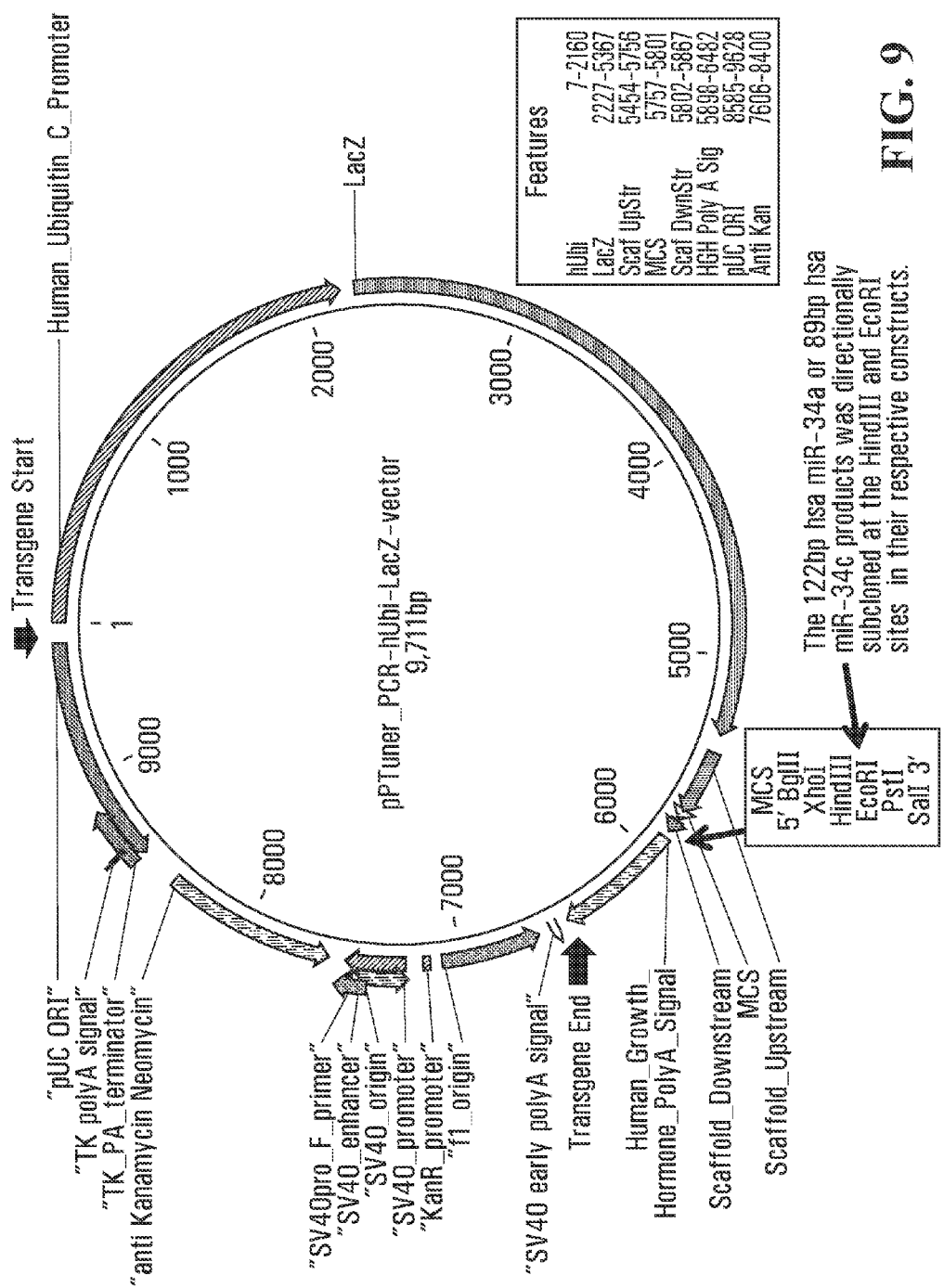
FIG. 9: Schematic showing a non-limiting illustration of the pPTuner-PCR-hUbi-LacZ-Vector used for cloning the 122 bp human microRNA 34a (hsa-miR-34a) or 89 bp human microRNA 34c (hsa-miR-34c) product that was directionally subcloned at the HindIII and EcoRI sites in their respective constructs.
Figure 10:
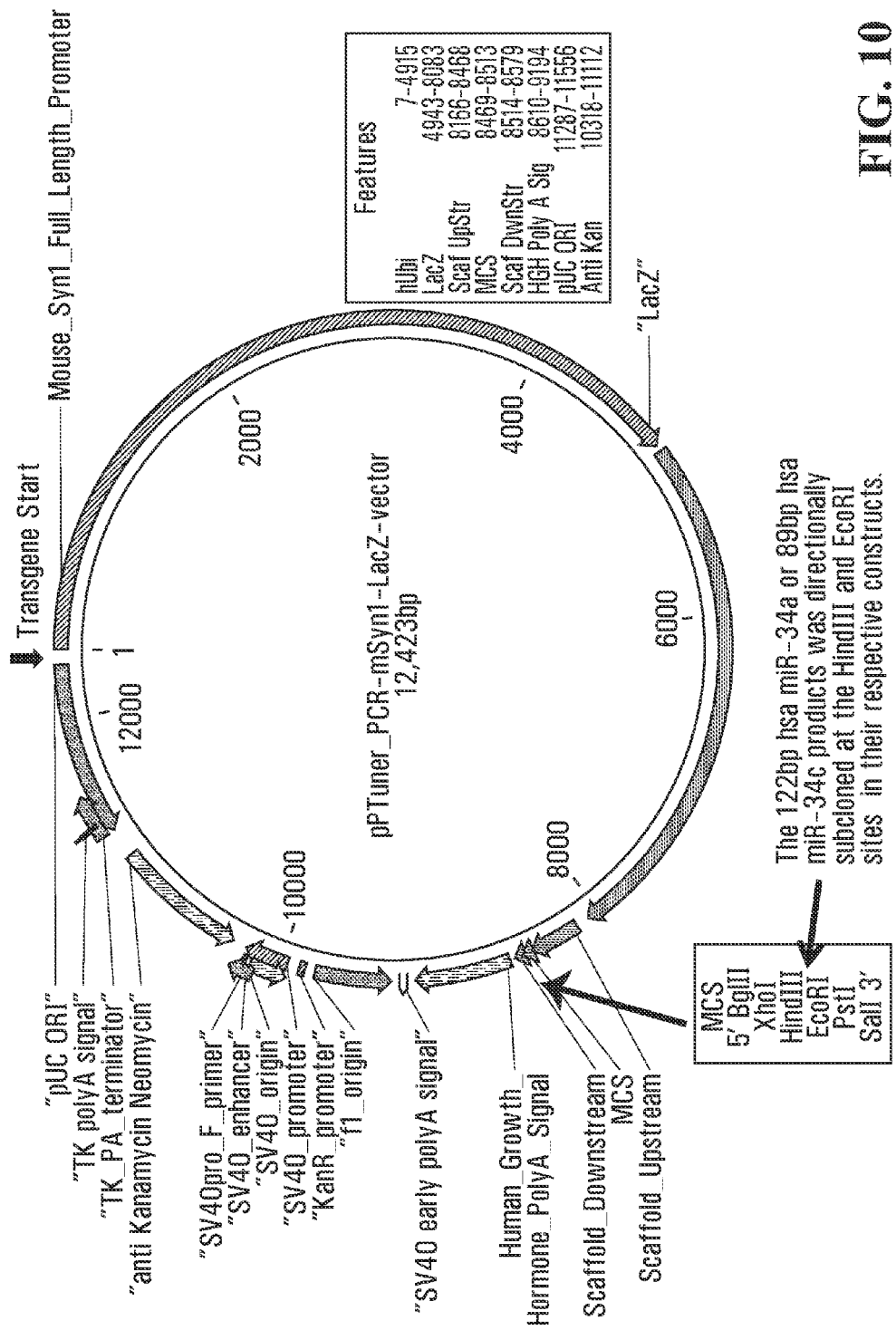
FIG. 10: Schematic showing a non-limiting illustration of the pPTuner-PCR-mSyn1-LacZ-Vector used for cloning the 122 bp hsa-miR-34a or 89 bp hsa-miR-34c product that was directionally subcloned at the HindIII and EcoRI sites in their respective constructs.

Precursor microRNA sequences of miR-34a or miR-34c were generated from PCR reaction from human genomic DNA; the amplified fragments were cloned to the miR-33 scaffolding linked with E. Coli LacZ for transgene detection in mutant mice. The human growth hormone poly-A was used as the stop codon. Mutants include the human ubiquitin promoter, for global expression of knock-in transgenic miR-34a (Tg-34a) or miR-34c (Tg-34c), or a neuronal-specific promoter for brain-specific expression of either microRNA transgene. One mutant, AGTcS1, was created with two copies of miR-34c in tandem repeat, to express two copies of this transgene in the brain, for a possible putative enhancing effect. All sequences used for this construct building are in the public domain and the person skilled in the art can obtain the desired sequence from various public available databases. We used the pPTuner vector as our backbone construct, obtained from Clontech, Incorporation (Catalog No. 632172). FIG. 6 illustrates the cloning steps to generate final constructs for injection into pronuclei for founder mice production. First, we generated two universal cassettes, as shown in Panel A; the only difference between the two is the promoter: mouse synapsin promoter (mSyn) for brain-specific expression; and human ubiquitin promoter (hUbi) for global expression. These two universal plasmid constructs were generated by PCR amplification of either the human or the mouse genome, with specific genomic sequence information for the respective Genebank references, as shown in FIGS. 7-8 for the mSyn plasmid, hUbi plasmid, human micro-33 plasmid, human growth hormone poly-A (hGH-polyA), and LacZ. LacZ from E. coli was used as detection marker for transgene expression in knock-in mouse strains; it was produced in the same fashion, using the bacterial genomic template for PCR amplification (FIG. 8, Panel A). The two universal cassettes, carrying either the mSyn or the hUbi promoter, were then generated by serial ligation and cloning to produce the mSyn-LacZ-hmiR-33-hGH-polyA and hUbi-LacZ-hmiR-33-hGH-polyA plasmids (FIG. 6, Panel A). These two plasmids were then used to produce mSyn-pTuner and hUbi-pTuner vectors, as shown in FIGS. 9 and 10, between the pUC ORI and SV40 early Poly A signal sites of the pPTuner backbone. We used human microRNA-33 (hmiR-33) as the backbone vector for the eventual microRNA transgene because of its unique feature, allowing all the precursor miRNAs to fold in the correct fashion to generate mature microRNAs [169]. We used human growth hormone poly-A sequences because they allow overexpression of the inserted microRNA transgenes under the respective promoters in mice, complementing the human miR-33 scaffold for human microRNA genes to be expressed in a mouse background [170].

Figure 14:
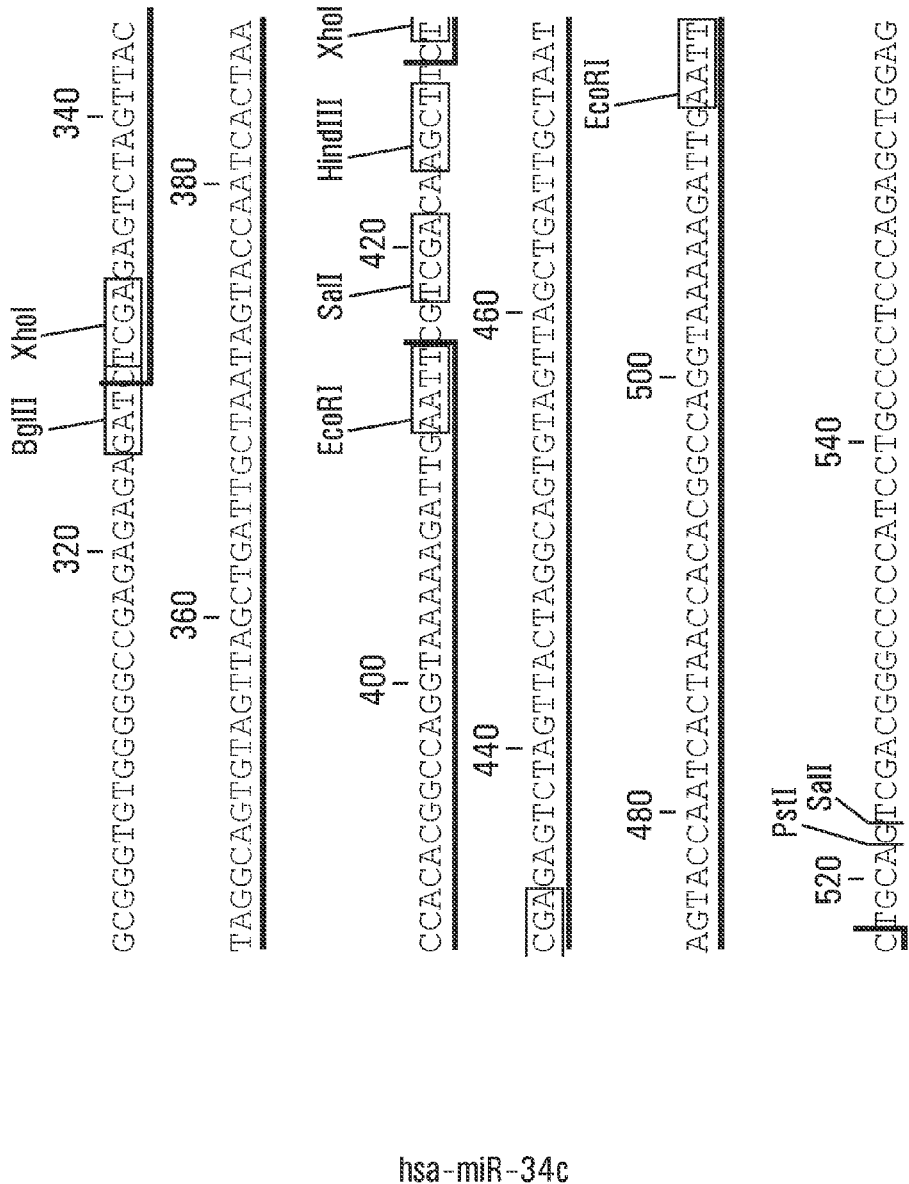
FIG. 14: Sequence showing 2 copies of miR-34c in tandem in clone 1 underlined (from XhoI to EcoRI).
Figure 15:
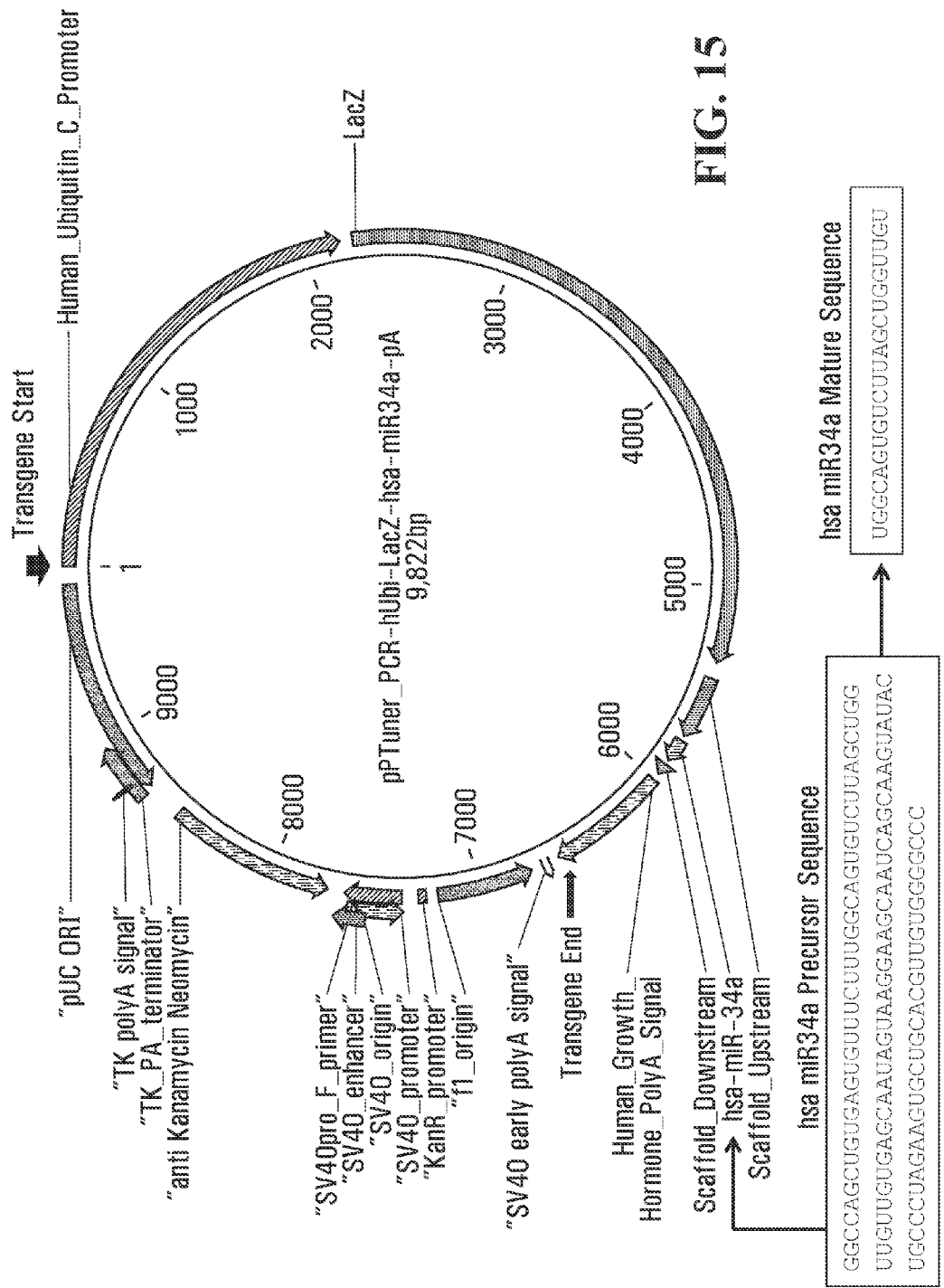
FIG. 15: Schematic showing a non-limiting illustration of the pPTuner-PCR-hUbi-LacZ-hsa-miR34a vector.
Figure 16:
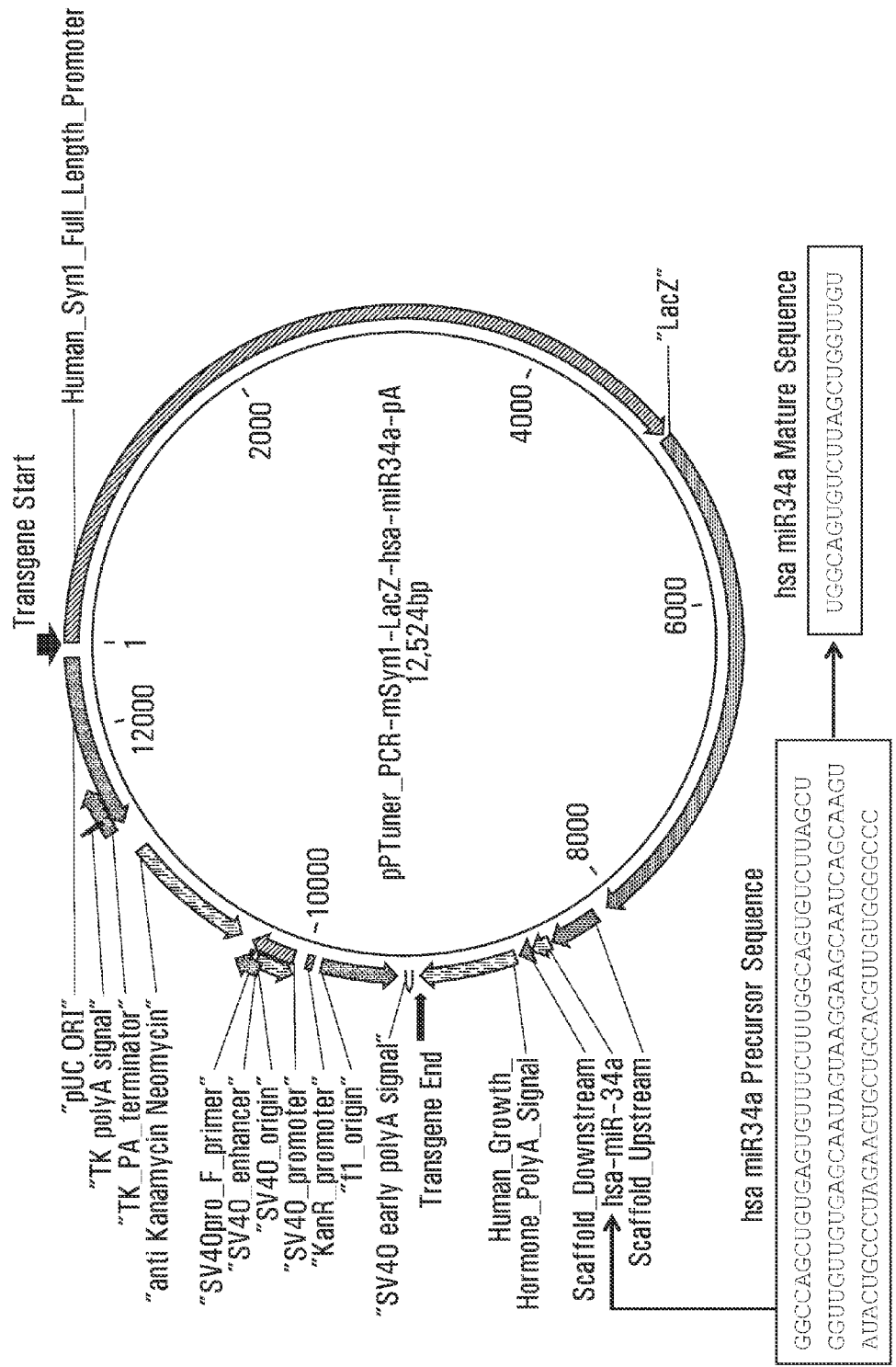
FIG. 16: Schematic showing a non-limiting illustration of the pPTuner-PCR-mSyn1-LacZ-hsa-miR34a vector.
Figure 17:
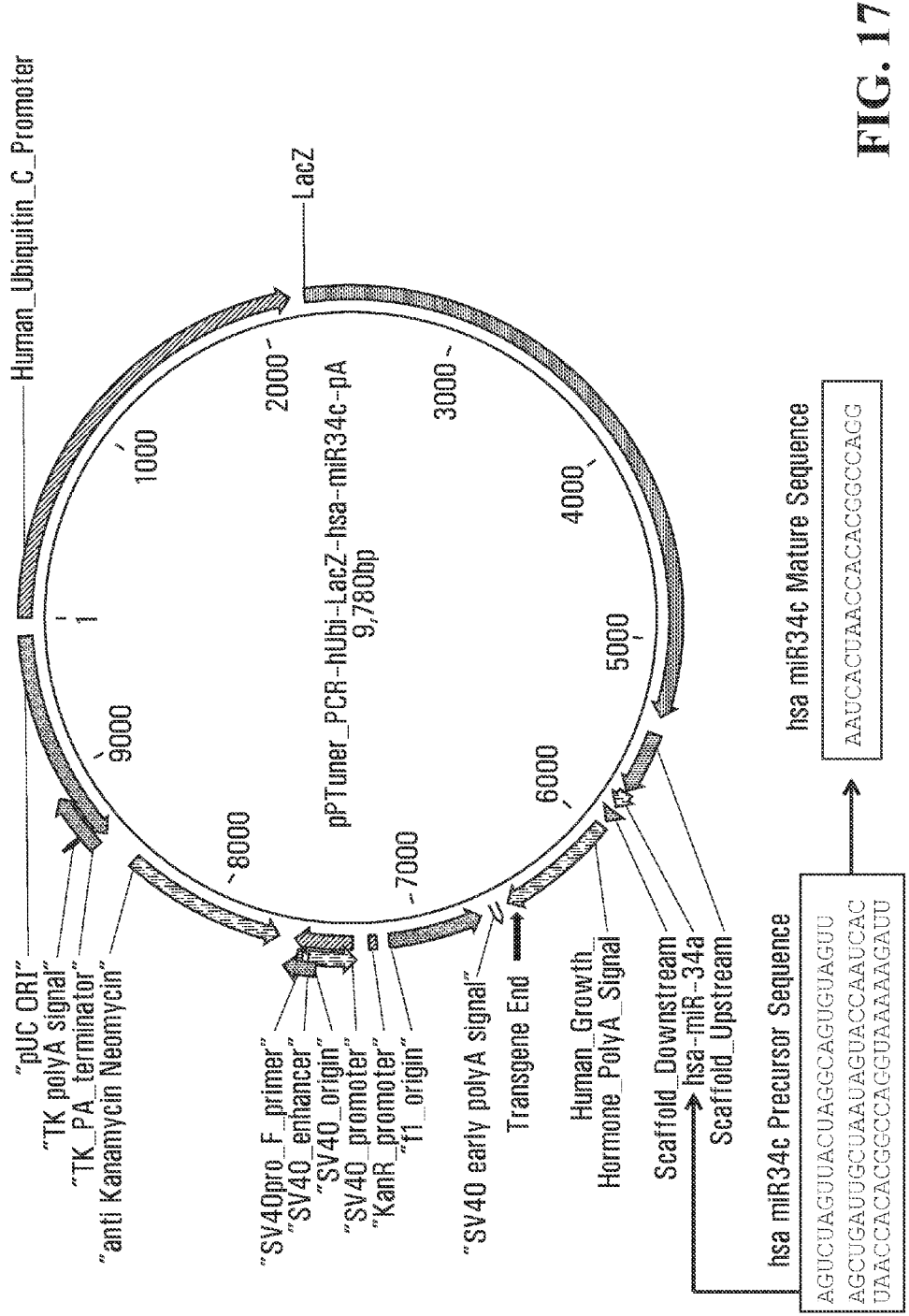
FIG. 17: Schematic showing a non-limiting illustration of the pPTuner-PCR-hUbi-LacZ-miR-hsa34c vector.
Figure 18:
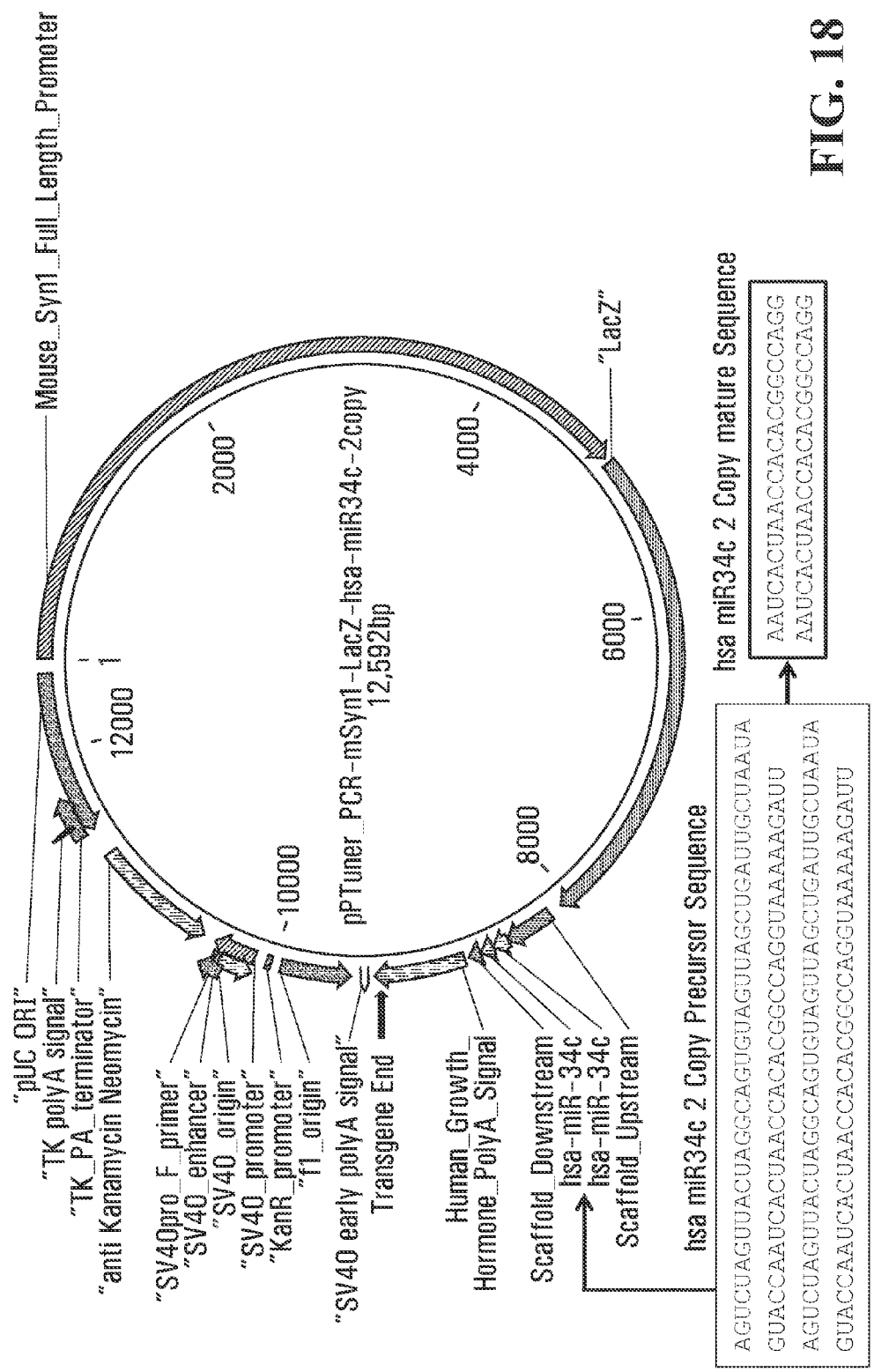
FIG. 18: Schematic showing a non-limiting illustration of the pPTuner-PCR-mSyn1-LacZ-hsa-miR34c 2 Copy vector.
Figure 19:
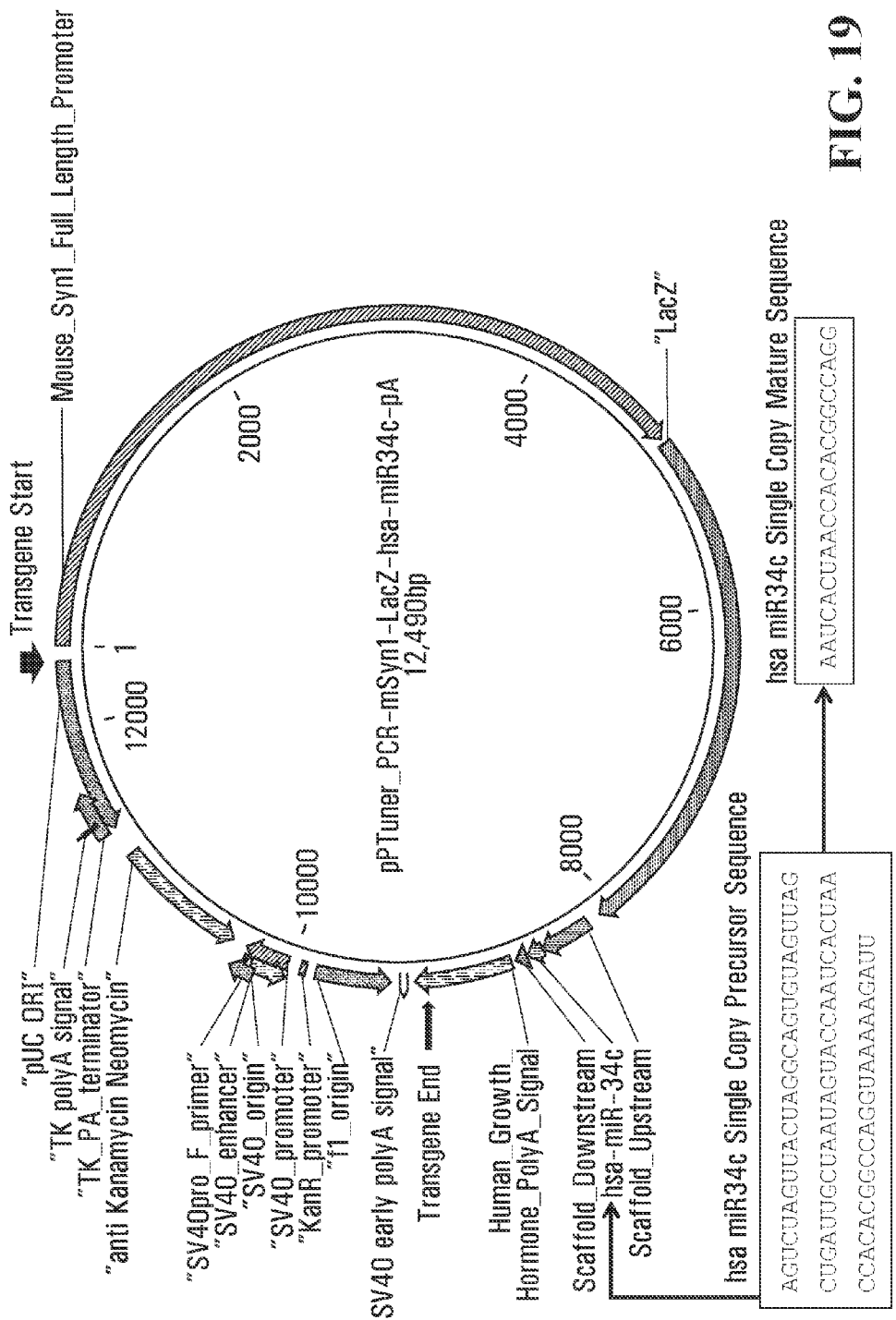
FIG. 19: Schematic showing a non-limiting illustration of the pPTuner-PCR-mSyn1-LacZ-hsa-miR34c Single Copy vector.

Following successful generation of these two pPTuner plasmids, mSyn-LacZ-miR-33-hGH-polyA and hUbi-LacZ-miR-33-hGH-polyA, precursor miR-34a or miR-34c was introduced by specific restriction sites within the microRNA-33 fragments (FIGS. 9 and 10). This was accomplished by specific sequence primers added to the precursor fragments of miR-34a or miR-34c, for the purpose of specific cloning into the mSyn or hUbi constructs (FIGS. 11 and 12). This step allows the final plasmids to produce the correct DNA fragments, with unique restriction sites that are not present in the miR-33 backbone vectors. Plasmids carrying all the added primers were generated by pDrive vector and sent out for sequencing (FIG. 13); results show all sequences to be correct by UCSC Genome Browser comparison, totally aligned with the human microRNA-34a or -34c sequences, by blasting with the known precursor sequences of these two microRNAs and the sequences of our clones are perfectly matched with the basepair sequences in the Genebank, except that the 2-copy miR-34c was examined manually, and showed the correct sequence, as seen in FIG. 14. The five different plasmids were then gel purified and excised for ligation to the correct restriction site in the pTuner backbone vector, carrying either of the two universal cassettes, as shown in FIGS. 15-19. For the final step to produce the transgene pronuclear injection, fragments from the Transgene start site, downstream from the pUC ORI site of the pPTuner backbone, to the transgene end site at the end of the hGH-polyA tail before the SV40 early polyA signal site of the pPTuner, were excised to produce the desired fragments, which were sent out for founder mice production, described below.

All five completed mutant constructs were evaluated for accuracy of all cloning steps, etc. by restriction enzyme digestion for fragment sizes, followed by direct sequencing of selected segments to verify their exact base pair information. Once these quality control steps were completed, the constructs were propagated in sufficient amounts for pronuclear injection, as described below.

Figure 20:
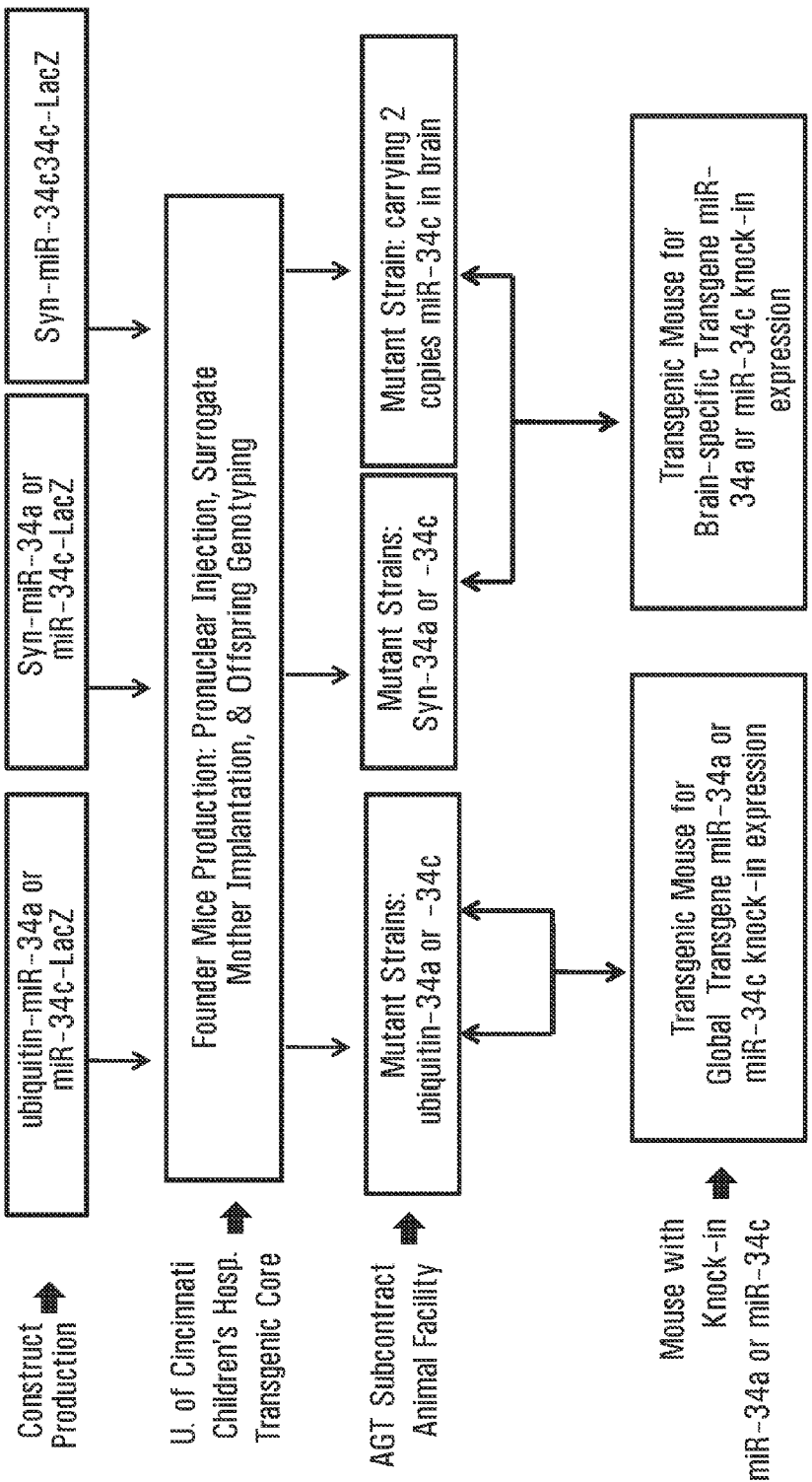
FIG. 20: Schematic showing a non-limiting plan for the production of founder mice for breeding transgenic mouse lines.
Figure 23:
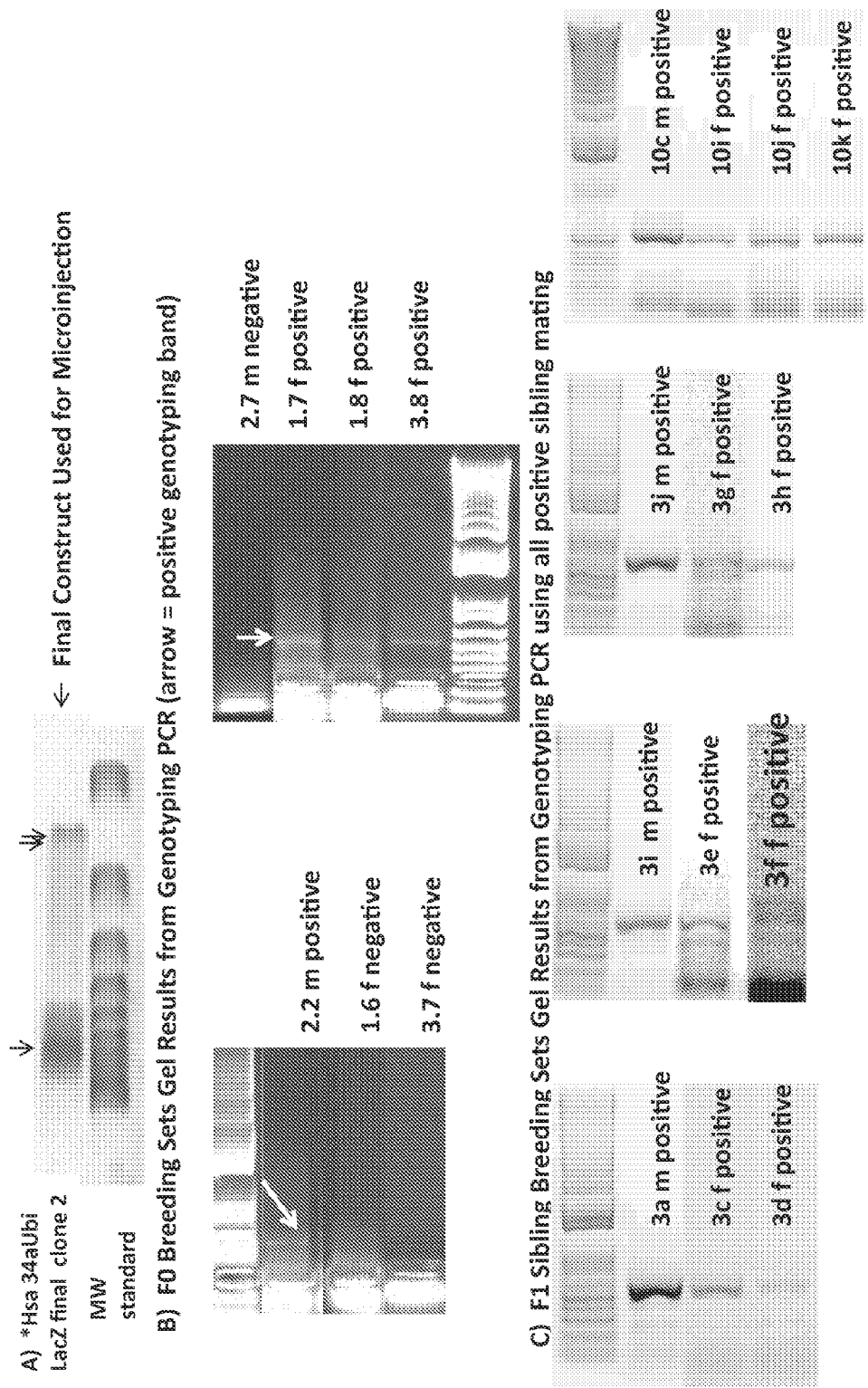
FIG. 23: hUbi-LacZ-hsa-miR34a (AGTaU2). Panel A: Final clone (single arrow) used for pronuclear injection; backbone is shown by the double arrow; Panel B: Founder mice with positive genotyped band (arrow) positive mice mated with negative mice; Panel C: The positive progenies showing the expected genotyped bands in the F1-generation.
Figure 25:
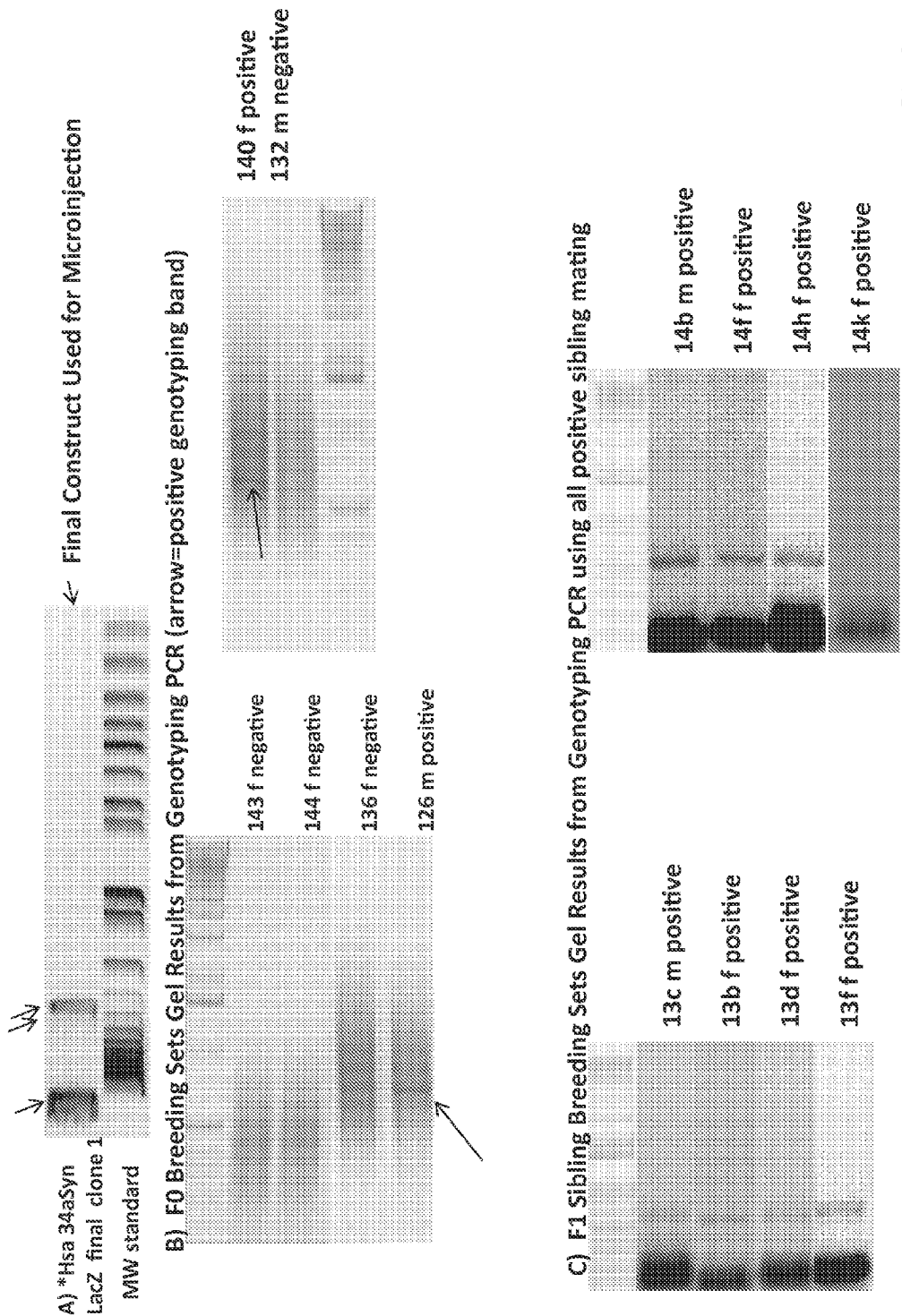
FIG. 25: mSyn1-LacZ-hsa-miR34a (AGTaS1). Panel A: Final clone (single arrow) used for pronuclear injection; backbone is shown by the double arrow; Panel B: Founder mice with positive genotyped band (arrow) positive mice mated with negative mice; Panel C: The positive progenies showing the expected genotyped bands in the F1-generation.
Figure 26:
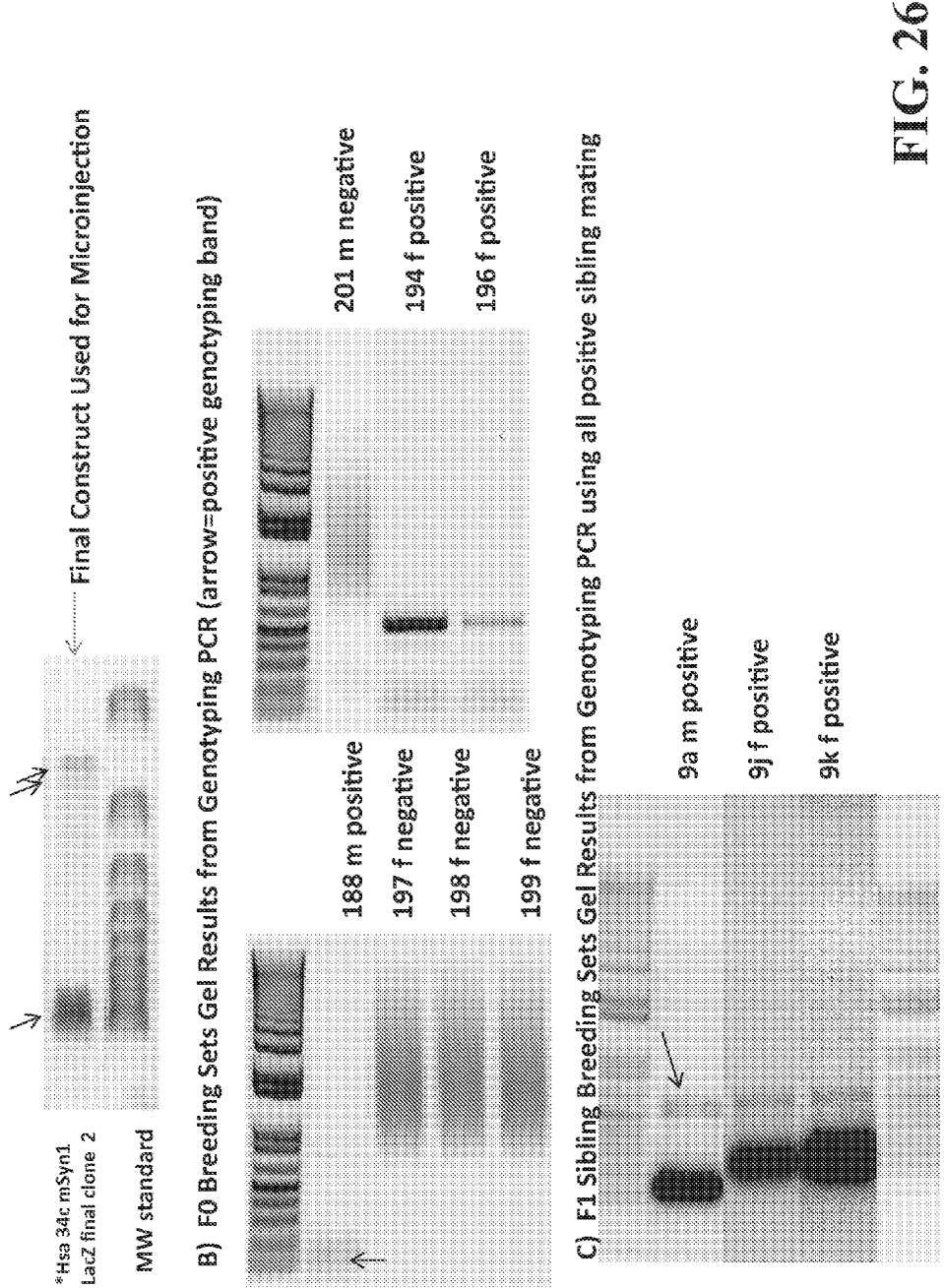
FIG. 26: mSyn1-LacZ-hsa-miR34c (AGTcS2). Panel A: Final clone (single arrow) used for pronuclear injection; backbone is shown by the double arrow; Panel B: Founder mice with positive genotyped band (arrow) positive mice mated with negative mice; Panel C: F1 mating of positive siblings all show positive bands.

Founder Mice Production, Genotyping and the F1-Breeding Program:

We used the pronuclear injection approach, which provides a jumpstart toward obtaining founder mice without the long procedure of cloning transgene-positive embryonic stem cells for injection, and subsequent backcrossing to select positive pups among chimeric offspring. We used the University of Cincinnati Children's Hospital Transgenic core service facility (CCHMC) for pronuclear injection and founder mice production. The founder mouse background strain is FVB/n, purchased from Harlan Labs. We provided the CCHMC with the five mutant construct plasmids; upon receiving them, they performed plasmid DNA purification and pronuclear transgenesis microinjection into mice of this strain. In general, one or two cycles of injection of 100-125 eggs were performed each time, then implanted into the surrogate mothers surgically. Pups born from these mothers are being genotyped by AGT staff, from tail snip samples provided by CCHMC. The pronuclear injection and hand-over to the Advanced Genomic Technology (AGT) animal facility for founder mice breeding are illustrated in FIG. 20.

Specific primers were designed, with sequences shown in FIGS. 21 and 22, for genotyping for human microRNA-34a (hsa miR-34a) and human microRNA-34c (hsa miR-34c). The pairs of primers, forward and reverse base pairs, were designed using the microRNA-33 scaffold sequences bracketing the miR-34a or miR-34c precursor sequences (in bold). FIGS. 23-27 show the complete genotyping exercise from the initial fragment used for pronuclear injection to the F0-generation genotyping then to the F1-generation genotyping: panel A of these five figures shows the clone containing the entire transgene for pronuclear injection; panel B shows positive and negative F0 founder mice, with the positive band by genotyping primers; and panel C shows the F1 generation with positive bands; these are for the sibling breeding program, shown in FIG. 28.

Figure 28:
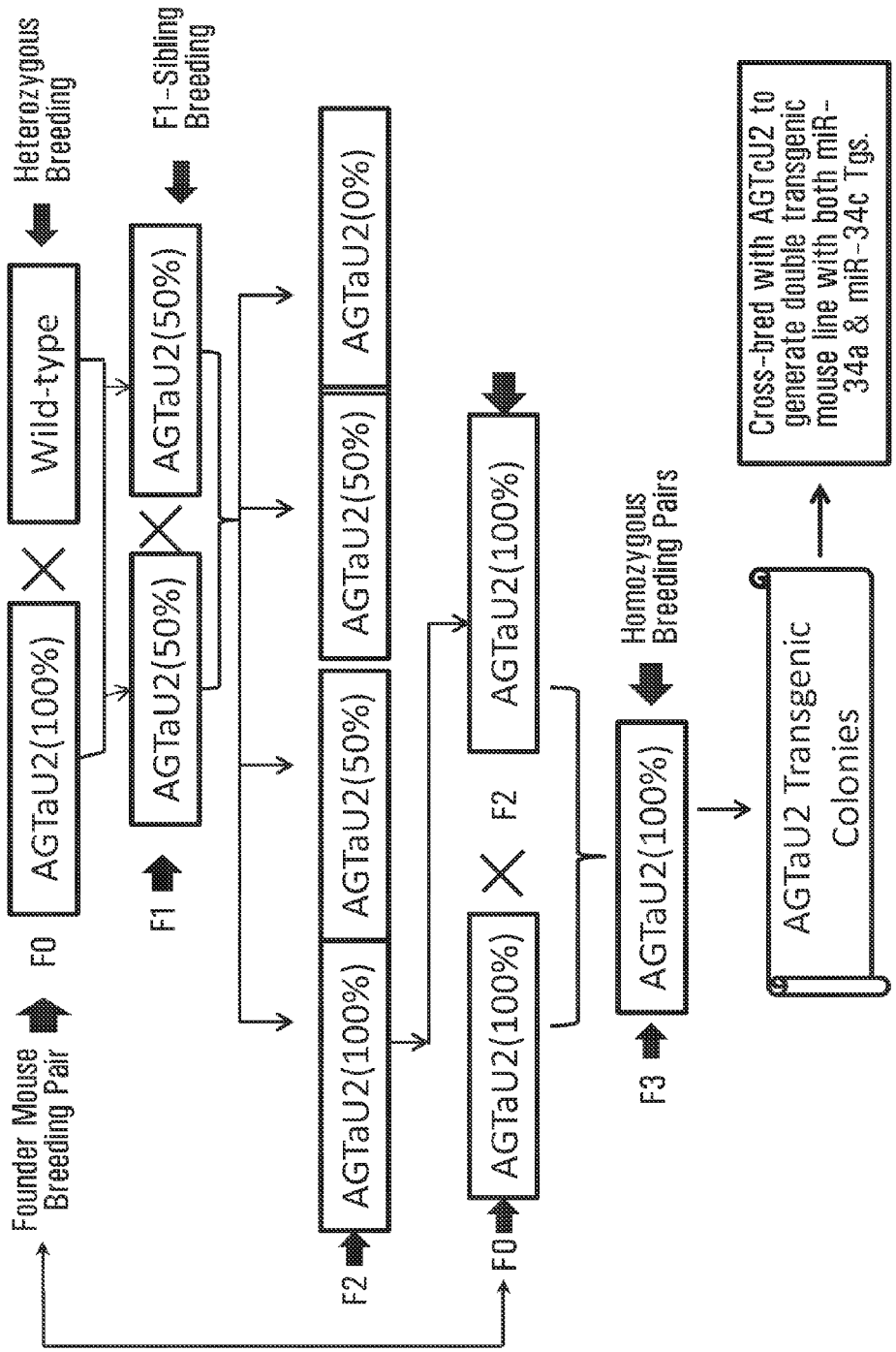
FIG. 28: Schematic diagram of a non-limiting breeding program from F0 founder generation to production of the F3 generation of homozygous breeding pairs, exemplified by AGTaU2, with the other four strains following the same general breeding program.

Cross-Breeding Five Founder Mouse Lines to Produce F1-Generation Transgenic Models:

The inventor has an existing subcontract with the University of Louisville for animal husbandry, breeding, colony establishment, etc. We have established colonies of founder mice of the five transgenic lines, in order to have enough mice for three purposes: a. sustaining the colony itself; b. crossing with other mutant lines to produce mutant models bearing both miR-34a & miR-34c; and c. as controls for characterizing the transgenic models. For F1 generation, we follow the protocol of mating positive males with negative females, so all the positive pups bear the same transgene insertion in terms of location and copy number as the male parental mouse; these positive pups are then used for F1 generation sibling breeding, to produce colonies of homozygous offspring. An additional breeding plan was performed with Tg-positive females mated with negative males, to generate F1 positive colonies for future breeding. However, F1 pups from these two mating schemes are not bred with each other, so that the chromosome locations of the Tg insertion is not mixed up. Genotyping is performed at each breeding cycle, for identification to correspond to the initial founders' identification, to ensure genotype specificity from tail specimens (FIG. 28).

Figure 29:
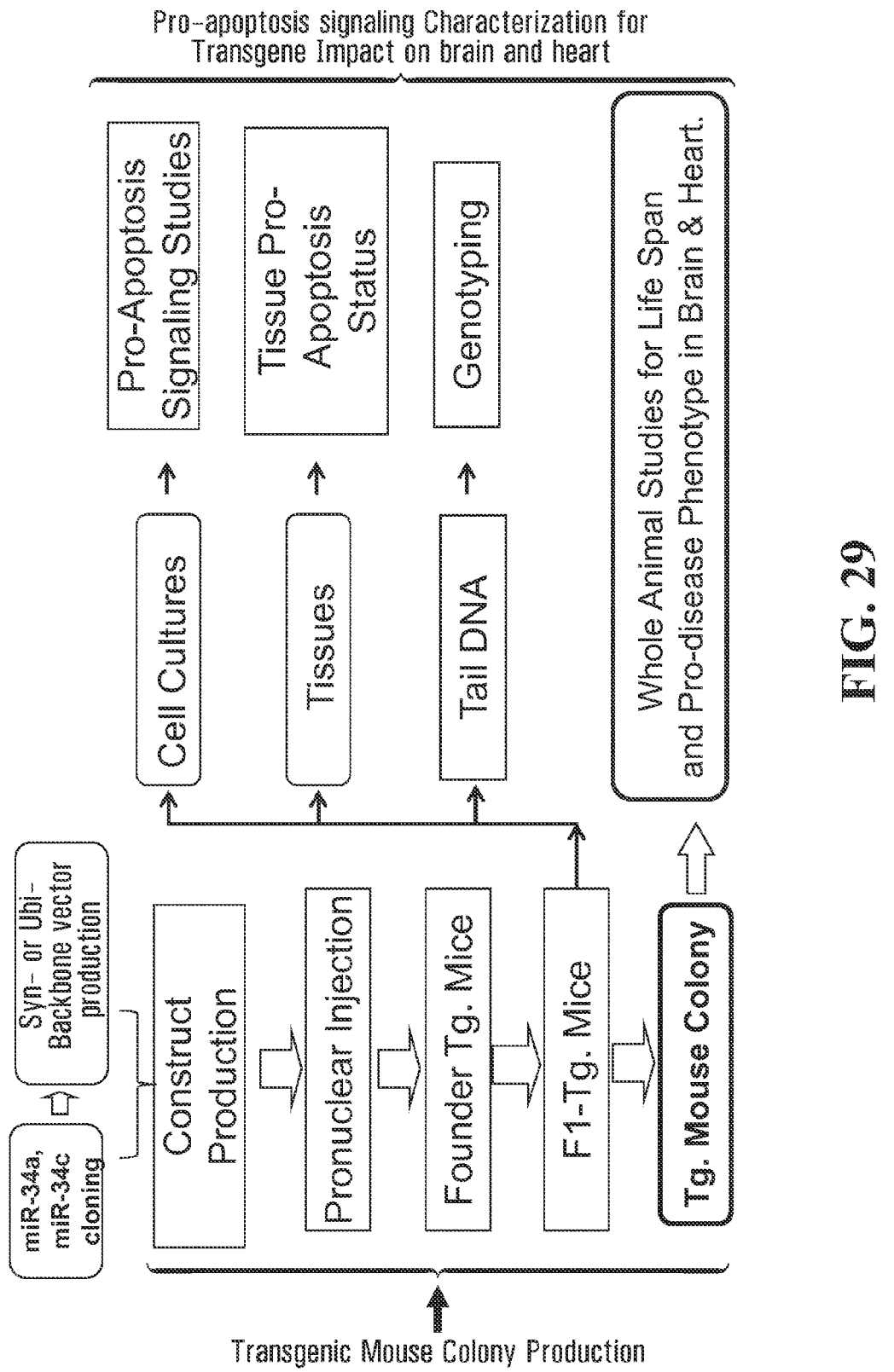
FIG. 29: Non-limiting flow chart of transgenic mouse production and characterization.

Initial Characterization of the Transgene Effect:

FIG. 29 summarizes a non-limiting example of a breeding program and characterization by: 1. Pro-apoptosis signalling increase in primary fibroblast cultures generated from kidney and lung of F1-positive transgenic mice; 2. Characterization of the presence of both precursor and mature forms of the transgenes, by qPCR with respective sequence information; 3. Characterization of putative suppression of the expression of selected target genes, such as Bcl2, SIRT1, etc.; and 4. Continuing genotyping validating the abundance of the transgene in cultures and tissues from positive mutants compared with negative controls.

Figure 31:
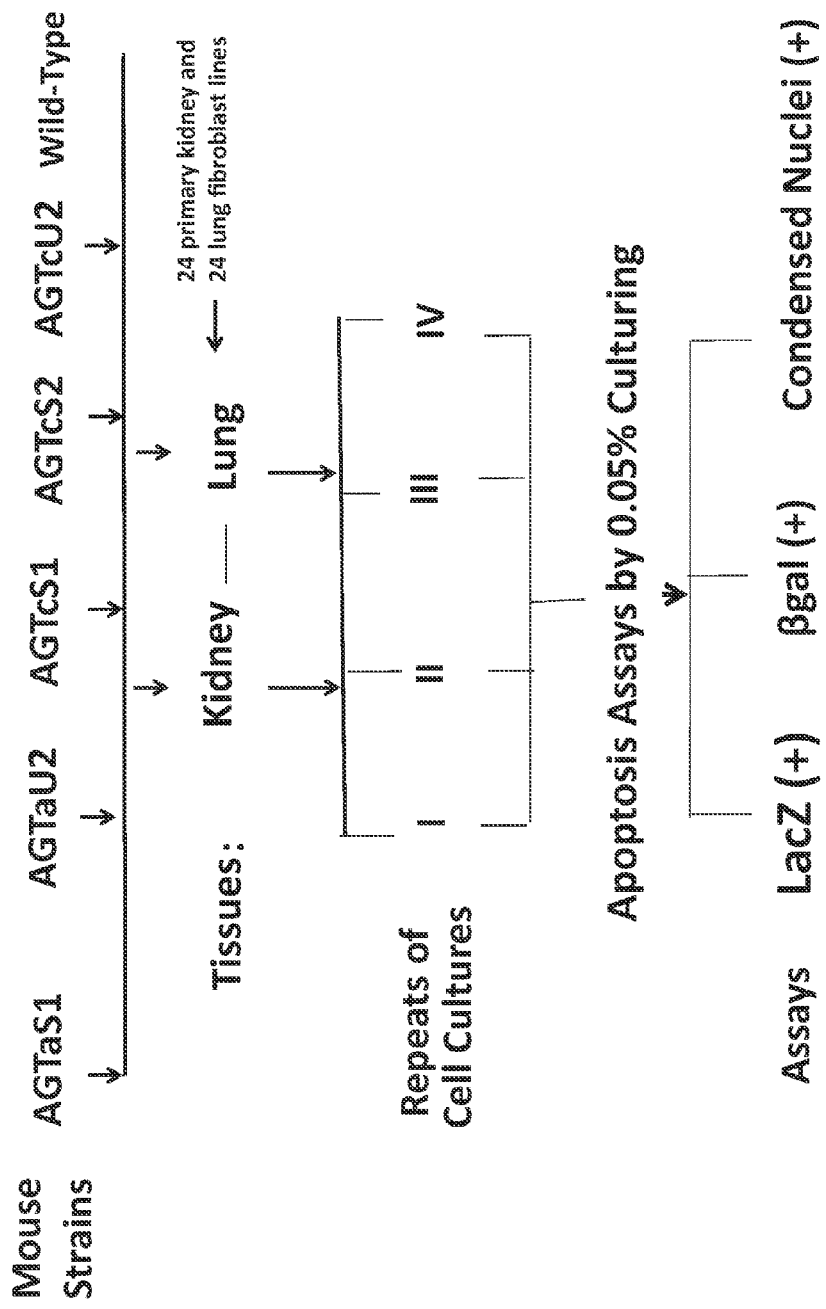
FIG. 31: Schematic diagram of a non-limiting strategy for primary Fibroblast culture assays for assessing pro-apoptosis phenotype.

Establishing Primary Fibroblast Cultures from Transgenic Mouse Pups, and Enhanced Apoptosis Assays:

We have established primary mouse fibroblast cultures from kidney and lung of four F1 positive mice from each of the five transgenic mutant lines, and four F1-negative mice. In total, there are 24 primary kidney fibroblast lines from the 5 transgenic mutant strains and one wild-type control, and 24 similar cultures generated from lung tissues of the same six mouse strains. FIG. 31 illustrates the first set of experiments assaying pro-apoptosis signalling in these cultures. In general, all cultures were established from kidney and lung tissues of male pups at postnatal day 15-20. After the initiation of cultures, i.e. culturing to no more than five population doubling levels (PDLs), most sister cultures were processed for long-term storage in −160° C. in complete medium supplemented with 10% dimethyl sulfoxide, and saved as founder cultures; the remaining ones are used as working cultures. So far all cultures are <8 PDLs, at which stages normally, senescence would not be observed.

Figure 32:
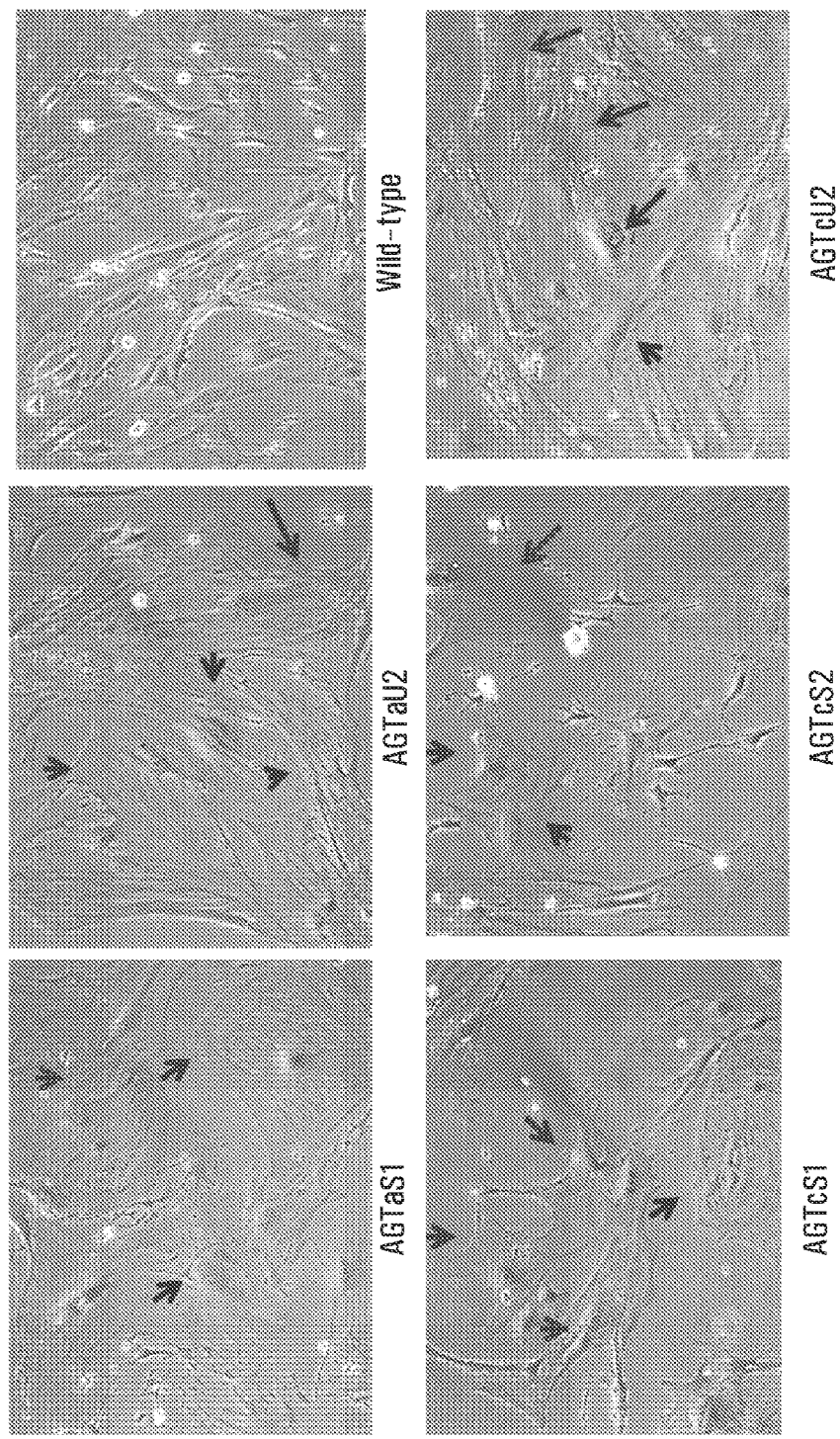
FIG. 32: Presence of increased number of cells with senescent phenotypes in all five transgenic fibroblast cell culture lines from both kidney and lung relative to wild type cell cultures. (Arrows point to fibroblasts with enlarged cell morphology typical of senescent fibroblasts.)
Figure 33:
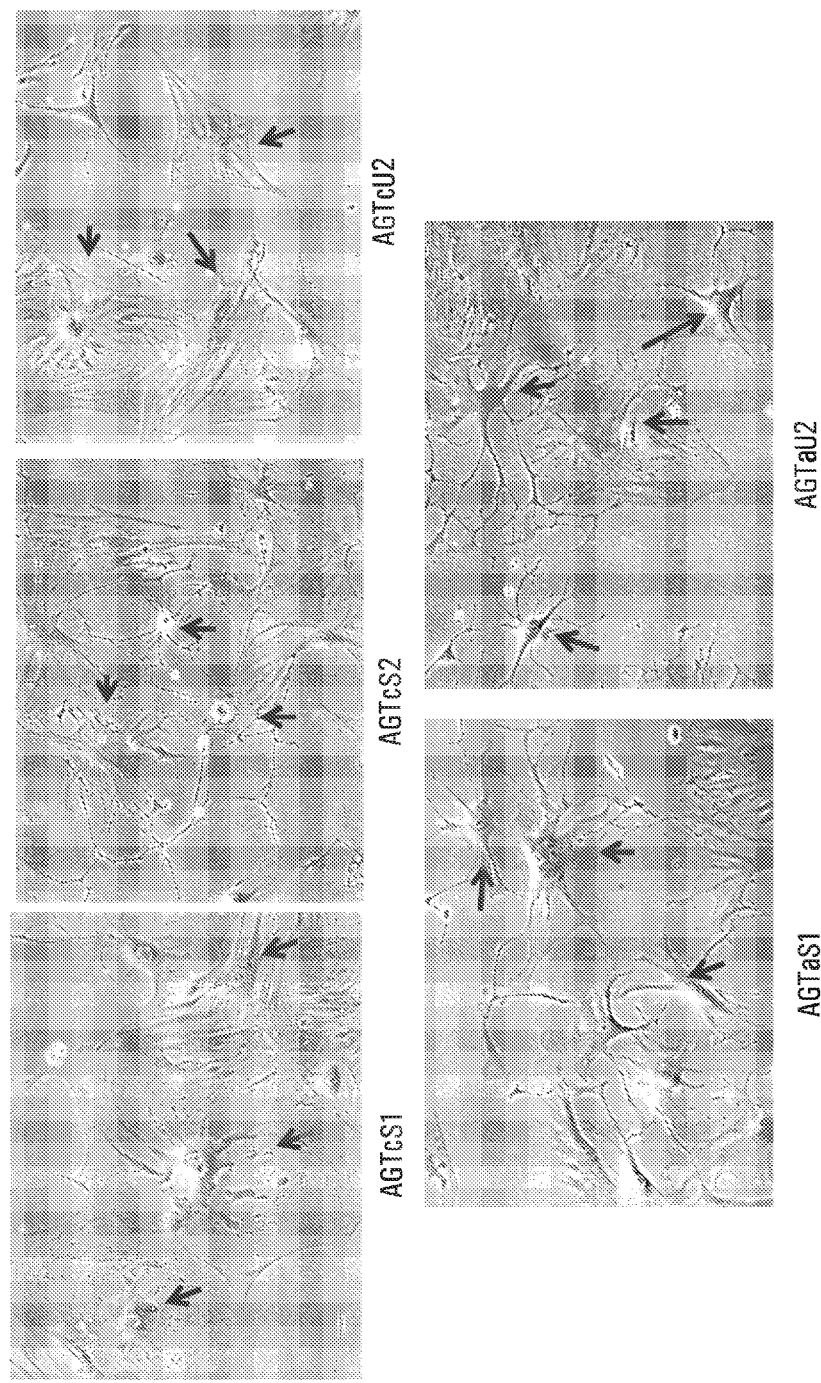
FIG. 33: Upon treatment with 0.05% serum-containing medium for 24 hours, most transgenic fibroblasts with senescent phenotypes undergo apoptotic death, showing shrinkage morphology typical of dying cells. (Arrows point to dying senescent fibroblasts.)

Replicatively Senescent Phenotype Characterization:

The replicatively senescent life span of cells derived from mice is measured by the standard determination of population doubling levels (PDLs). In general, the PDL of any given cell strain is obtained by serially passaging a strain of culture, once it is established from the tissue explant. We have used this methodology to investigate control mechanisms for replicative senescence; the replicative potential of any culture can be estimated by the remaining PDLs, calculated by subtracting the current from the cumulative PDL. In general, when cultured fibroblasts reach the replicatively senescent phenotype, one can observe irreversible growth arrest, increased cell size, distinct flat and enlarged morphology, beta-galactosidase (SA-beta-gal) activity, accumulation of lipofuscin granules, and broad changes in gene expression [99]. Cultured mouse fibroblasts differ from human in that the replicatively senescent period is often called "crisis", because a subsequent spontaneous transformation may take place in them which is generally never seen in human fibroblasts. Replicative life spans of mouse fibroblast cultures in general are significantly shorter than human cells, ranging around 15-20 PDLs when the mouse fibroblasts are cultured under an ambient $O_2$ level of 20%, compared to some 54-58 PDLs in the human WI38 cell strain. When mouse fibroblast cultures are kept at a physiological level of 3%, their replicative life span is significantly increased [171]. Nevertheless, we observe that our primary fibroblast cultures derived from kidney and lung exhibit enlarged cell morphology and beta-gal staining even at passage 1, without further serial passaging. In almost all cultures derived from kidney or lung, about 20% of cells show the enlarged phenotypes of flattened cell morphology, some showing double nuclei; cells showing this phenotype are at a significantly reduced level of 1-2% in cultures derived from the wild-type, transgene-negative mice (FIG. 32).

Transgene-Positive Cells are Pro-Apoptotic Death:

We used a simple method to test whether fibroblasts derived from transgenic mouse strains were more prone to apoptotic signaling. In general, serum deprivation, i.e., culturing in the absence of serum, is a standard method of inducing apoptosis. However, we found that in this case, almost all cell cultures from transgenic mouse strains die rapidly, within a hour. We then subjected our cultures to incubation in 0.05% serum-containing medium; most cultures survive in this low serum, but without proliferation, for up to a week. Interestingly, all cultures from the five transgenic lines undergo apoptotic death at 24-48 hours after culturing in 0.05% serum; moreover, the apoptotic morphology is most noticeable, with cells showing the senescent phenotype (FIGS. 33 and 34(A)-(E)). Triplicate sister cultures of the five transgenic mutant lines from kidney and lung all show condensed nuclear morphology by DAPI staining, and nearly no Bcl2 staining, in most of these dying fibroblasts (FIG. 35(A)-(E)). Almost all apoptotic cells are positive for the LacZ staining [175] which reflects the presence of transgene expression (FIG. 34, Panel B & E). At higher concentration of the staining, the dye stains for beta-galactosidase, the hallmark of senescent fibroblasts (FIG. 34, panel C & F). As shown, almost all cells showing condensed nuclei are those bearing the transgene-LacZ positivity, and beta-gal positive; these results suggests that the transgene may induce the senescent phenotype in the primary culture fibroblasts even at the very early stage of culturing and they are vulnerable to cell death.

Standard protocols for apoptotic indices include: (i) propidium iodide (PI) staining of condensed chromosomes, TUNEL staining for in situ DNA fragmentation assays, for binding of biotinylated UTP to nicked DNA, and localization of the bound UTP by fluorescence-tagged avidin labelling; (ii) DNA ladder assays, providing an overall DNA fragmentation profile; and (iii) flow cytometric assays of annexin and PI staining, to separate apoptotic (positive only for annexin) from necrotic (positive for both annexin and PI) cell profiles. The combined results from these assays provide a comprehensive understanding of apoptotic status, not only globally in the entire culture, but also individually in subpopulations.

Figures 36A, 36B:
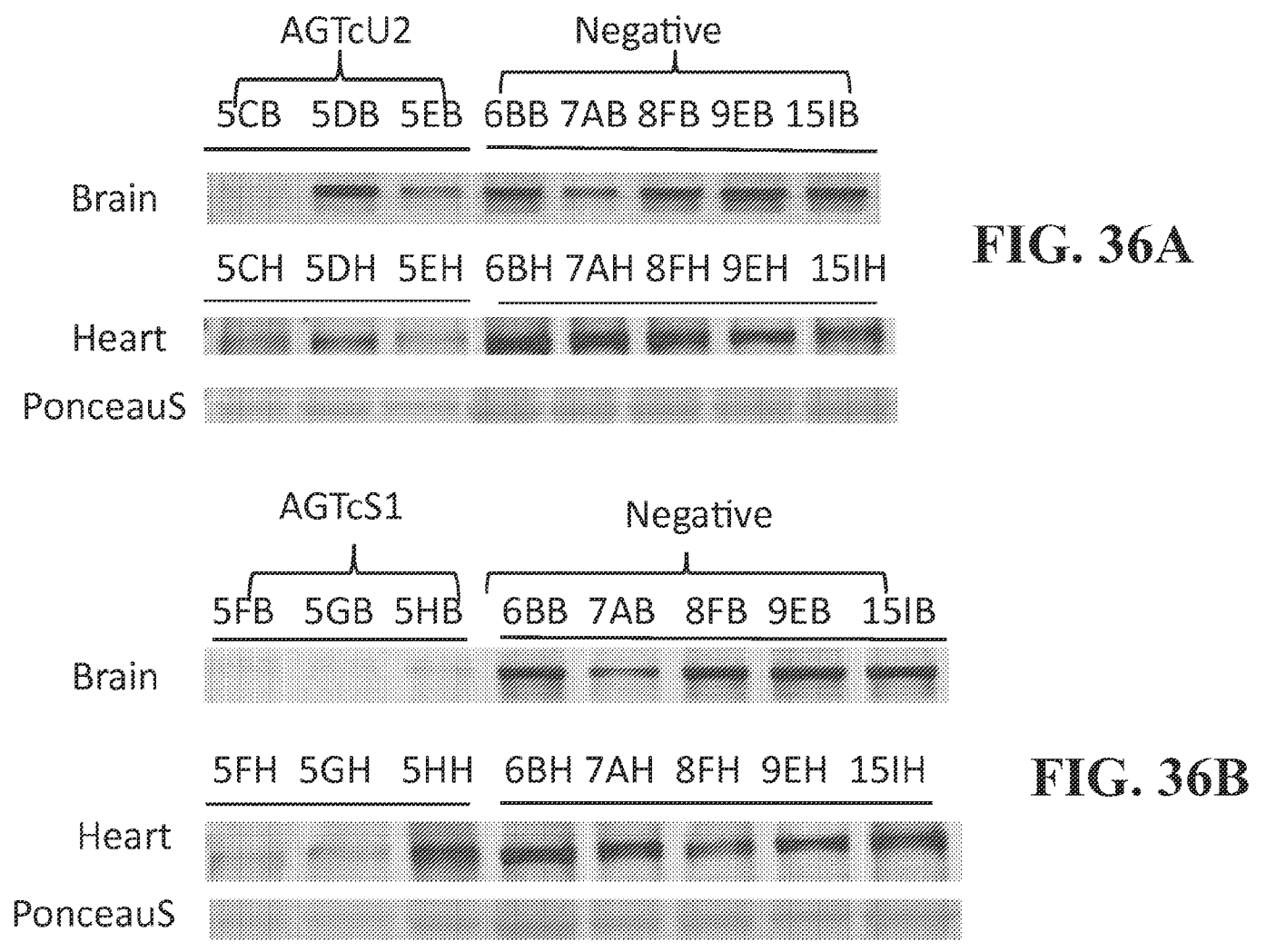
Figure 37:
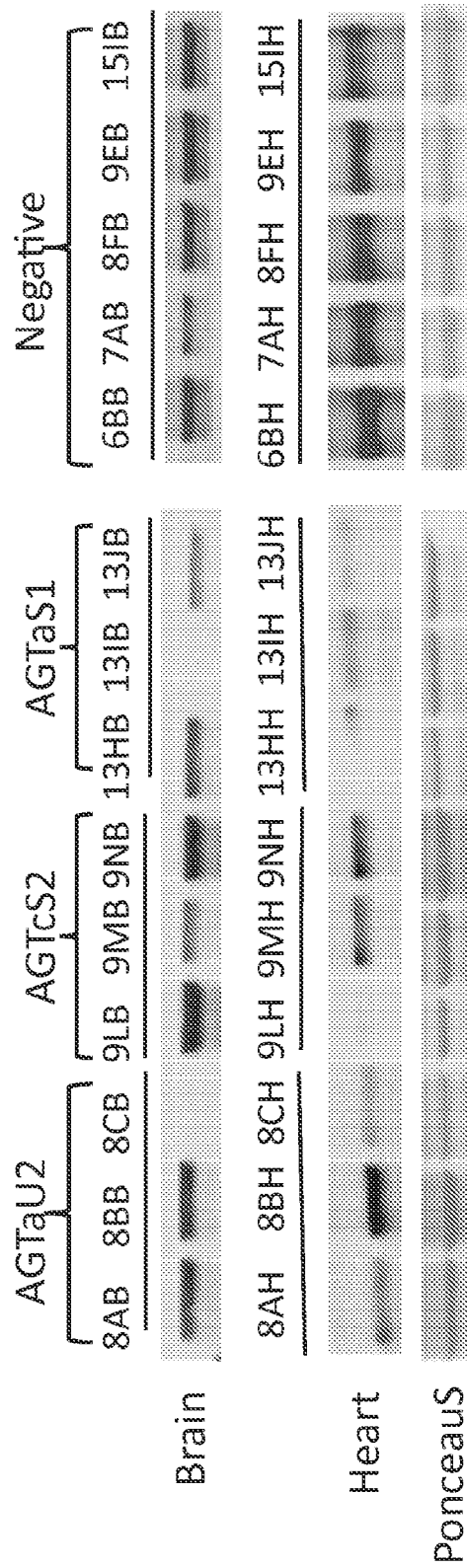
FIG. 37: Western blotting of SIRT1 abundance in three strains of transgenic mouse mutants: AGTaU2, with the Ubiquitin (U) promoter for global expression of miR-34a; AGTcS2, with the mSyn promoter for brain-specific expression; and AGTaS1, with the mSyn-promoter for brain-specific expression of miR-34a. Numbers denote individual transgenic mice, either positive for the specific mutant transgene expression, or negative showing no positive genotype bands. For brain samples, the loading control was actin; for heart specimens, a specific band of the same intensity was used as the loading control. Five negative control mice with no detectable positive genotype bands were used.
Figure 38A:
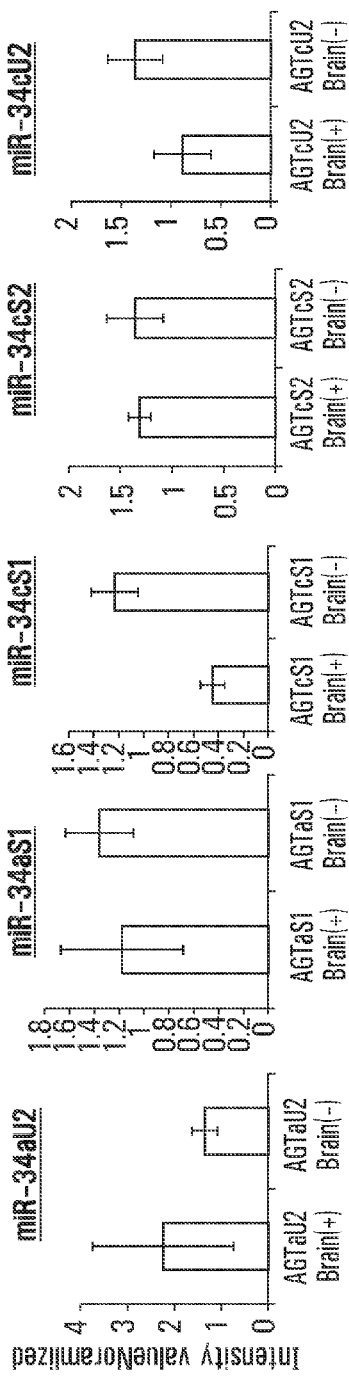
FIG. 38: Histographs showing quantification of SIRT1 band intensities in brain (Panel A) and heart (Panel B) of five transgenic mouse mutants: AGTaU2 with Ubiquitin-driven miR-34a; AGTaS1 with mSyn-driven miR-34a; AGTcS1 with mSyn-driven two copies of miR-34c; AGTcS2 with mSyn-driven one copy of miR-34c; and AGTcU2 with Ubiquitin-driven miR-34c. Three animals with different genotyped band intensities were used for prospective positive transgenic mutants, while five negative control mice with no detectable positive genotype bands were used.
Figure 38B:
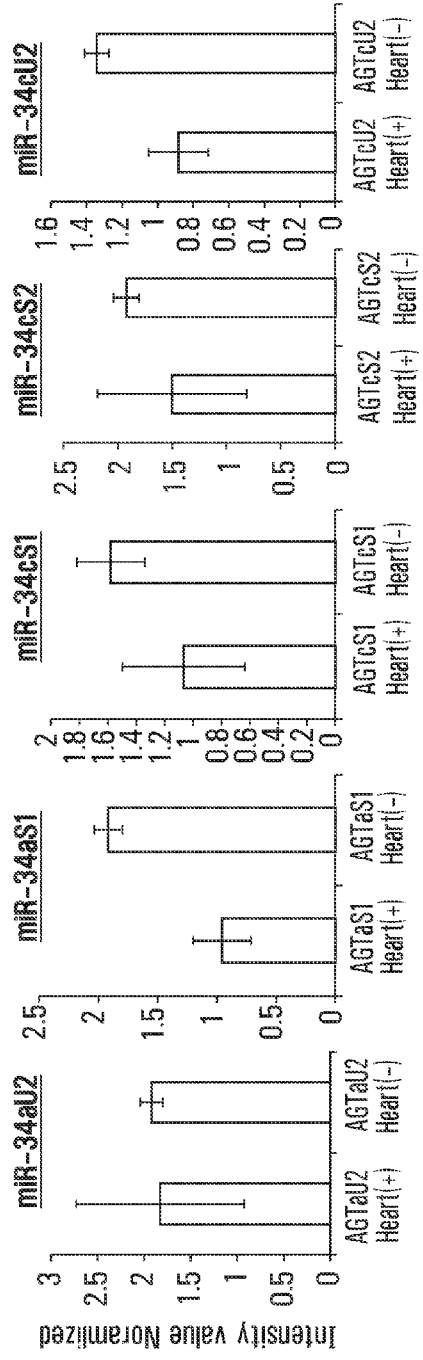

Since SIRT1 and Bcl2 are the best known functional targets of both miR-34a and miR-34c, we investigated whether the overexpression of these two microRNAs in our transgenic mutants would exhibit putative repression of these two target genes in brain and heart, two organs selected for either global expression, by ubiquitin promoter (Ubi), or brain-specific expression by mouse synapsin (mSyn) promoter. Levels of SIRT1 in brain and heart are shown in FIGS. 36-37 in actual gel images of band intensities of SIRT1 for five transgenic mutants: AGTcU2 for global overexpression of miR-34c; AGTcS1 for brain-specific expression of two copies of miR-34c; AGTaU2 for global overexpression of miR-34a; AGTcS2 for brain-specific expression of one copy of miR-34c; and AGTaS1 for brain-specific expression of miR-34a. These Western blotting analyses show that, except for AGTaU2 with Ubiquitin-driven miR-34a transgene, the other four strains show reduced levels of SIRT1 in both brain and heart. Interestingly, SIRT1 levels in heart show decreased levels even in strains carrying brain-specific expression of either miR-34a or miR-34c, compared with negative mice, litter mates with no detectable positive genotype bands. Also evident in this analysis is significant inter-animal variance among positive transgenic mice; this may be due to variance in transgene insertion efficiency into the parental genome of this F1 generation. This variance will be reduced as we proceed to F2 and F3 breeding, by a sibling mating program.

FIG. 39 shows reduced expression of the other target of both miR-34a and miR-34c, Bcl2 protein. For heart tissue, we selected the AGTcU2 strain for Ubiquitin-driven expression of miR-34c (Panel A: gel image; Panel B: histograms for band intensities), with three animals each of the transgenic mutant strain and four negative control mice. For brain tissue, we selected the AGTaS1 strain for brain-specific expression of miR-34a, and AGTaU2 for Ubiquitin-driven expression of miR-34a. In all three mutant strains, Bcl2 levels are reduced.

Results shown in FIGS. 36-39 demonstrate that both SIRT1 and Bcl2 are reduced in level, compared with littermates with negative presence of transgene genotyped bands observed as early as 1.5 month old since all tissues used in this study were harvested at this young age from both transgene mutants and their control negative mice. For SIRT1 expression, it seems that mutants carrying two copies of miR-34c in brain show the most significant repression of this target gene expression. As described above, this significant reduction of SIRT1 protein levels is even observed in heart tissues of mutants bearing transgenes driven by the mSyn promoter.

As described previously, so far age is the best predictor for AD; no animal model exactly approximates the late-onset, age-related AD which characterizes the majority of AD victims. SAMP8 mice, which show accelerated aging, are used as a model for sporadic AD, since it is based on age rather than gene mutants, as in the transgenic mice carrying AD mutations. SAMP8 mice have been bred since 1975, and were recently characterized as a model of accelerated aging. Recently, SAMP8 mice have been used to evaluate drug efficacy in terms of anti-Aging and/or anti-AD effects, such as reversing learning impairment by injecting anti-amyloid beta polypeptide antibody across the blood-brain barrier. Our results show that the level of miR-34a is increased in the brain of these mice, but at 3 months of age, nine months earlier than in C57/B6 mouse brain; the increase of the level of this microRNA may thus serve as a candidate biomarker for accelerated aging.

We have established colonies for both groups of animals for our Tissue Bank collection, so they are available for various assays for age-dependent changes. Table 2 shows all the strains, vendor sources and age groups from which data are being collected as baseline information for our transgenic mouse mutants. The age groups defined for each strain are based on literature reports of symptom manifestation. In the case of SAMP8 mice, we were only able to maintain the colony up to 8 months, since by this time, most of the mice are showing extreme old age phenotype and for the sake to collect the tissue samples before death set in, the maximal age group for SAMP8 mice was set to 8-months old. For all AD transgenic strains, literature reports maximal symptomatic manifestation at 12 months, starting at 6 months with detectable amyloid plaque formation and tau hyper-phosphorylation in brain tissues. Our tissue sample collection and monthly survival bleeding for collection of blood specimens started at 4 months of age.

TABLE 2

| SAMP8 | 3 months | 6 months | 9 months | 10-12 months |
|---|---|---|---|---|
| Brain, Liver, PBMC, & Plasma | 5 | 5 | 5 | 5 |

| SAMR1 | 3 months | 6 months | 9 months | 10-12 months |
|---|---|---|---|---|
| Brain, Liver, PBMC, & Plasma | 5 | 5 | 5 | 5 |
| 129S6.Cg-Tg(APP$^{SWE}$)2576Kh2789-M | | Taconic Laboratory | | |
| 695-a.a. isoform of human β-amyloid | a 14-fold in | | | |

TABLE 2-continued

| (Aβ) PP | Aβ(1-42/43) at 11-13 months of age | | | |
|---|---|---|---|---|
| Single transgenic (Aβ) PP-AD mice | 3 months | 6 months | 9 months | 12 months |
| Brain, Liver, PBMC, & Plasma Tg(Prnp-MAPT*P301L)JNPL3HImc (2508-M) P30L mutation of the microcrotubule associated protein tau gene (MAPT) | 5 | 5 Taconic Laboratory | 5 | 5 |
| Single transgenic Tau-AD mice | 3 months | 6 months | 9 months | 12 months |
| Brain, Liver, PBMC, & Plasma APP$^{SWE}$-Tau (2469-M) | 5 | 5 Taconic Laboratory | 5 | 5 |
| P301L mutation of microtubule-associated protein tau gene (MAPT) + 695-a.a. isoform of human β-amyloid (Aβ) PP | | | | |
| Double transgenic for Tau and Aβ | 3 months | 6 months | 9 months | 12 months |
| Brain, Liver, PBMC, & Plasma APP$^{SWE}$-Tau Control | 5 | 5 Taconic Laboratory | 5 | 5 |
| Control for either single or double tg for Tau and Aβ | 3 months | 6 months | 9 months | 12 months |
| Brain, Liver, PBMC, & Plasma | 5 | 5 | 5 | 5 |

Five animals for each study group were used, to ensure statistical significance of each experiment with microRNA expression and target studies. For tissue samples, we have brain and liver specimens; monthly blood samples were used to generate peripheral blood mononuclear cells (PBMC) and plasma.

Survival Bleeding Program, and Results from SAMP8 and AD-Tg Mice to Prove that Survival Bleeding is Noninvasive, a Sustainable Method for Tracing Systemic 'Footprints' for Increased miRNA Expression in Brain.

Figure 40:
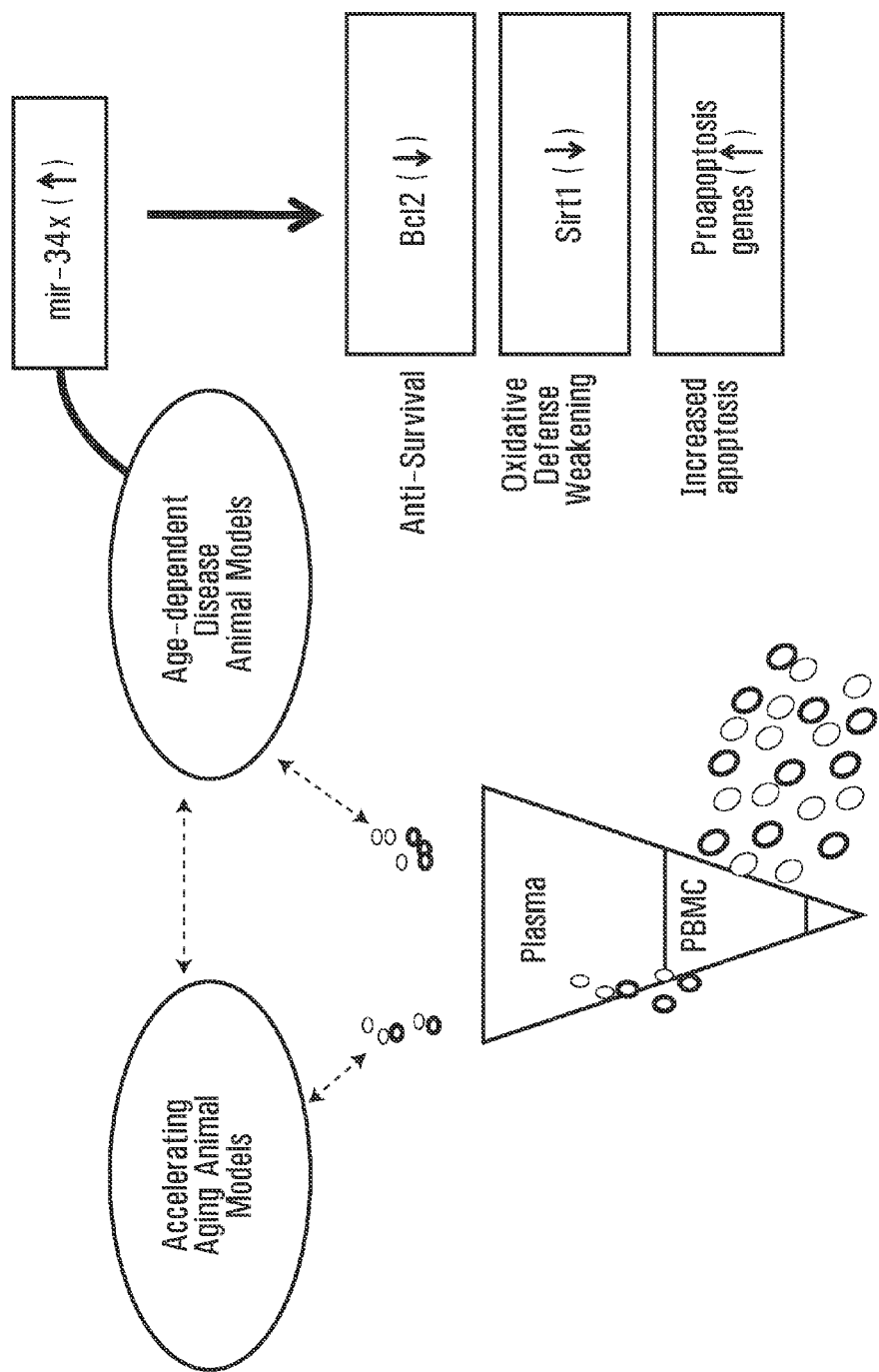
FIG. 40: Schematic showing a non-limiting illustration of survival bleeding samples, reflecting systemic abnormality by circulating microRNA 34× or circulating target polypeptide.

Currently, no literature has reported the use of animal plasma and/or PBMC to monitor staging or disease progression in preclinical model studies of any disease, including Alzheimer's disease. For preclinical model studies, to the inventor's knowledge, neither published papers nor companies report involvement in developing blood-based methodology for disease staging. To date, only a few papers have been published investigating microRNA expression in AD mouse mutants, and they are strictly working with end-stage brain specimen studies [56]. None has reported using circulating PBMC or plasma of mouse blood to measure early, intermediate, and late stages of brain disorder in mouse models; therefore we have adapted survival bleeding to obtain blood samples from mice at these stages, and examine levels of specific microRNAs and their target polypeptides in their blood, as non-invasive animal drug efficacy tests for a pre-clinical therapeutic discovery strategy. Most current anti-AD drug efficacy testing, besides behavioural studies, sacrifices animals at treatment intervals to quantify the development of plaque and tangle pathology. This not only requires costly large mouse colonies for investigation of temporal changes, but also data generated will be affected by built-in inter-animal variance among mice of different litters, etc. Longitudinal survival bleeding without euthanasia for fine mapping of AD staging, in serial blood specimens from 3 to 12 months, minimizes inter-animal variation and colony size. Moreover, blood-based changes in early phases before massive neuropathology develops in brain may be useful as pre-symptomatic markers. Such markers may be parameters for drug discovery to delay, slow down and/or reduce deleterious disease outcome in brain. FIG. 40 illustrates the use of survival bleeding to obtain blood specimens as systemic biomarkers for brain and heart pro-apoptosis signalling via increase of microRNA-34 family members.

Survival bleeding is traditionally practiced via retro-orbital, tail clipping, or cardiac puncture. Each of these approaches has its shortcomings: the retro-orbital vein method is not desirable due to its inhumane stress to the animal; cardiac puncture requires a highly skilled person, and is more frequently used in terminal than survival bleeding. Tail vein clipping yields only a few drops of blood, and cannot be repeated multiple times sequentially. Survival bleeding is reported for repeated bleeding in a humane way, with sufficient blood volume collected per sample. The procedure published by Golde, et al. [181] describes submandibular bleeding via the facial vein, using either lancet or 18 gauge needle, collecting 0.2 to 0.5 ml blood without anesthesia. The facial vein is located at the back of the mouse jaw, where orbital, submandibular and other veins join to form the beginning of the jugular vein. Access to this area can be accomplished by holding the mouse in a stress-free state, and then tapping the vein for blood collection (see details at reference 182) In general, survival bleeding by this procedure needs to consider body weight, species, and frequency of sampling; 0.2 to 0.5 ml of blood may be collected from each adult animal, with a 2 week rest interval. For the herein described results, although they are at adult 3 month age for the first bleeding, all mutant strains are considered not as robust as C57/B6, so we only collected 0.2 ml, and allowed 4 weeks rest interval between bleedings. We have practiced this protocol with our SAMP8 mutants and controls and the AD-transgenic mouse mutants, and find it suitable with minimal discomfort to the animals.

Figure 41:
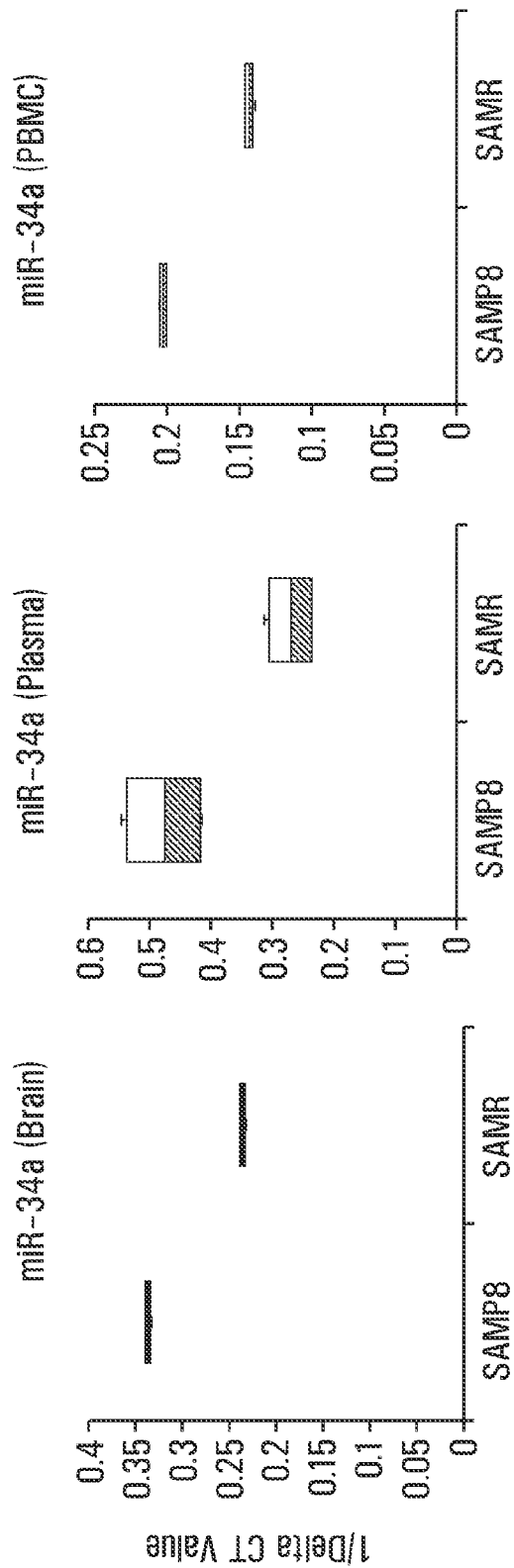
FIG. 41: Levels of miR-34a assayed by qPCR in brain, plasma and PBMC of 6 month old SAMP8 and control SAMR mice.

Proof-of-Principle that Plasma Levels are in Concordance with Levels in Brain:

We have used survival bleeding with our existing 6-month-old SAMP8 and control SAMR strains, and successfully demonstrate that 200 μl of blood can be serially collected from the submandibular facial vein, yielding ~1 μg PBMC RNA and ~1-3 μg plasma RNA specimens. These specimens support comparative analysis of specific microRNA expression levels in brain, PBMC and plasma, as illustrated in FIG. 41; up-regulated microRNAs are seen in all three samples in SAMP8 mutants compared to control SAMR mice. This result demonstrates that plasma levels are in concordance with levels in brain.

Survival Bleeding Schedules and Protocols for RNA and Polypeptide Isolation from Blood Samples:

After establishing the colonies shown in Table 2, our survival bleeding regimen started at 4 months old, continuing at one month intervals until the mice reached 12 months of age, or earlier depending upon animal health decline close to this time point. One month interval survival bleeding allows recovery exceeding the required 2 weeks. In general we used more than 3 mice per strain, to increase data output in case of inter-animal variation with survival bleeding, as well as attrition due to death. Monthly survival bleeding provided multiple data points, to examine the very first detectable increase of miRNA levels as pre-symptomatic markers, before any detectable behavioural, phenotypic and/or brain abnormalities. This allowed us to determine gradual trends of increase, and specific threshold points at which increased expression in plasma levels off, before brain disorders were observed at the histochemical level; the timing of these stabilized points served as the pre-symptomatic window in circulating blood samples for brain disorders.

Figure 42:
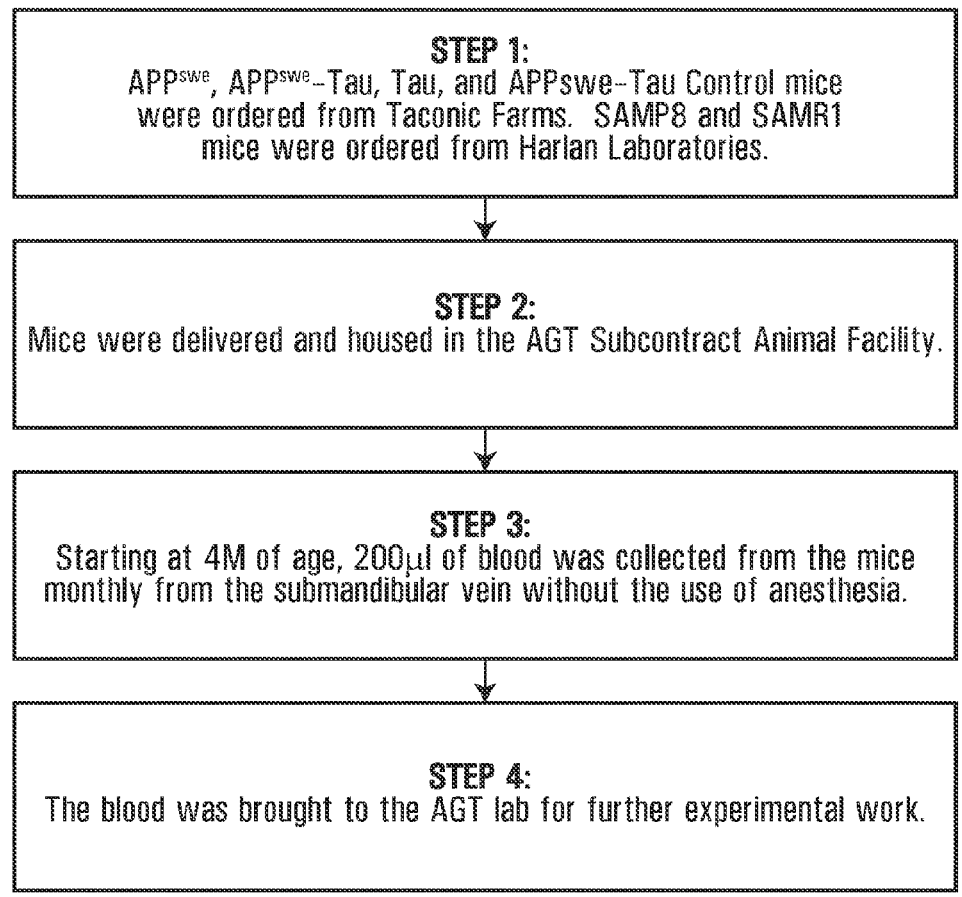
FIG. 42: Schematic showing a non-limiting illustration of a general plan for animal housing and blood collection.
Figure 43:
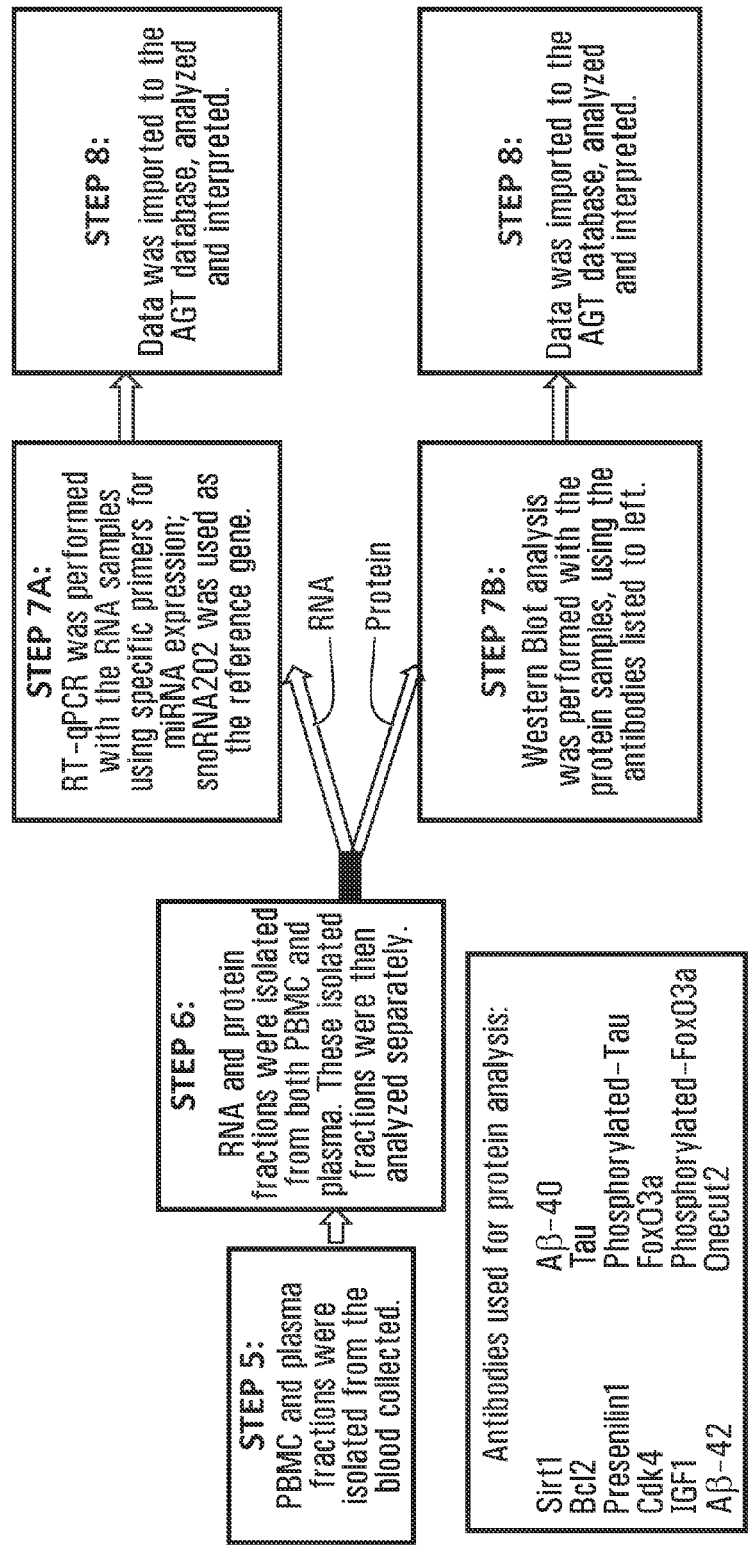
FIG. 43: Schematic showing a non-limiting illustration of a general plan for blood processing and analysis of polypeptide and microRNA levels.

FIGS. 42 and 43 illustrate a non-limiting example of a flow chart for survival bleeding studies, from the establishment of the animal colonies specified in Table 2. Our biorepository of survival bleeding samples and further processing them to obtain the RNA and polypeptide samples are shown in Table 3-7 with the selected month charts showing the quantities of RNA and polypeptide specimens obtained.

TABLE 3

| | Strain | Blood Collection #1 | | Blood Collection #2 | | Blood Collection #3 | |
|---|---|---|---|---|---|---|---|
| | | plasma (#animals) | PBMC (#animals) | plasma (#animals) | PBMC (#animals) | plasma (#animals) | PBMC (#animals) |
| AD Mice | WW | 4M (4) | | 5M (5) | | 6M (5) | |
| | APPSWE | 4M (3) | | 5M (3) | | 6M (3) | |
| | APPSWE-Tau | 4M (5) | | 5M (5) | | 6M (5) | |
| | Tau | 4M (4) | | 5M (5) | | 6M (5) | |
| SAMP8 and SAMR1 mice | SAMR1 | 3M (5) | | 4M (5) | | 5M (5) | |
| | SAMP8 | 3M (5) | | 4M (5) | | 5M (5) | |

| | Strain | Blood Collection #4 | | Blood Collection #5 | | Blood Collection #6 | |
|---|---|---|---|---|---|---|---|
| | | plasma (#animals) | PBMC (#animals) | plasma (#animals) | PBMC (#animals) | plasma (#animals) | PBMC (#animals) |
| AD Mice | WW | 7M (5) | | 8M (5) | | 9M (5) | |
| | APPSWE | 7M (3) | | 8M (2) | | 9M (2) | |
| | APPSWE-Tau | 7M (5) | | 8M (5) | | 9M (5) | |
| | Tau | 7M (5) | | 8M (5) | | 9M (5) | |
| SAMP8 and SAMR1 mice | SAMR1 | 6M (5) | | 7M (5) | | 8M (5) | |
| | SAMP8 | 6M (5) | | 7M (5) | | 8M (4) | |

| | Strain | Blood Collection #7 | | Blood Collection #8 | | Blood Collection #9 | |
|---|---|---|---|---|---|---|---|
| | | plasma (#animals) | PBMC (#animals) | plasma (#animals) | PBMC (#animals) | plasma (#animals) | PBMC (#animals) |
| AD Mice | WW | 10M (5) | | 11M (5) | | 12M (5) | |
| | APPSWE | 10M (4) | | 11M (4) | | 12M (4) | |
| | APPSWE-Tau | 10M (5) | | 11M (5) | | 12M (5) | |
| | Tau | 10M (5) | | 11M (5) | | 12M (5) | |
| SAMP8 and SAMR1 mice | SAMR1 | *SAMP8 and SAMR1 were sacrificed at 8M | | | | | |
| | SAMP8 | | | | | | |

TABLE 4

Three month old survival bled SAMP8 and SAMR1 specimens

| Strain | volume of blood | PBMC RNA conc. (ng/μl) | Plasma RNA conc. (ng/μl) | RNA total volume of each plasma and PBMC (μL) | PBMC protein conc. (μg/μl) | PBMC protein total volume (μl) | Plasma protein conc. (μg/μl) | Plasma protein total volume (μl) |
|---|---|---|---|---|---|---|---|---|
| SAMR1 | 200 μL | 19.6 | 33.8 | 20 | 1.2 | 35 | 19.7 | 200 |
|  |  | 16.4 | 28.7 | 20 | 1.0 | 35 | 18.1 | 200 |
|  |  | 20.9 | 32.7 | 20 | 1.6 | 35 | 18.2 | 200 |
|  |  | 17.6 | 35.6 | 20 | 0.8 | 35 | 18.4 | 200 |
|  |  | 55.5 | 36.1 | 20 | 2.3 | 35 | 18.3 | 200 |
| SAMP8 | 200 μL | 104.4 | 67.2 | 20 | 2.0 | 35 | 25.5 | 200 |
|  |  | 68.9 | 43.1 | 20 | 0.8 | 35 | 7.0 | 200 |
|  |  | 125.4 | 29.2 | 20 | 2.4 | 35 | 13.1 | 200 |
|  |  | 14.3 | 35.6 | 20 | 0.7 | 35 | 23.3 | 200 |
|  |  | 121.1 | 68.0 | 20 | 3.3 | 35 | 9.4 | 200 |

TABLE 5

Samples isolated from 200 μl blood of 4M AD mice

| Mouse | PBMC RNA Concentration ng/μl | Plasma RNA Concentration ng/μl | RNA total volume (μL) | PBMC Protein Concentration μg/μl | PBMC Protein total volume (μL) | Plasma Protein Concentration μg/μl | Plasma Protein total volume (μL) |
|---|---|---|---|---|---|---|---|
| WW1 | 623.2 | 158.6 | 20 | 1.3 | 35 | 7.2 | 100 |
| WW2 | 469.8 | 177.1 | 20 | 1.8 | 35 | 10.5 | 100 |
| WW3 | 396.4 | 146.1 | 20 | 1.2 | 35 | 8.2 | 100 |
| WW4 | 319.1 | 230.9 | 20 | 1.7 | 35 | 9.7 | 100 |
| WW5 |  |  |  |  |  |  |  |
| A2 | 545.8 | 277.7 | 20 | 1.9 | 35 | 8.9 | 100 |
| A3 | 372.1 | 170.9 | 20 | 1.7 | 35 | 10.2 | 100 |
| A4 | 782.4 | 222.8 | 20 | 1.7 | 35 | 14.2 | 100 |
| AT-1 | 574.5 | 187.0 | 20 | 1.9 | 35 | 7.8 | 100 |
| AT-2 | 330.5 | 245.8 | 20 | 1.4 | 35 | 4.0 | 100 |
| AT-3 | 306.7 | 272.5 | 20 | 1.2 | 35 | 9.2 | 100 |
| AT-4 | 427.5 | 215.8 | 20 | 1.8 | 35 | 7.3 | 100 |
| AT-5 | 371.8 | 220.9 | 20 | 1.6 | 35 | 4.8 | 100 |
| T6 | 292.6 | 132.6 | 20 | 1.9 | 35 | 11.7 | 100 |
| T7 | 273.4 | 227.6 | 20 | 1.4 | 35 | 16.7 | 100 |
| T8 | 341.7 | 217.1 | 20 | 1.5 | 35 | 13.4 | 100 |
| T9 | 60.6 | 64.5 | 20 | 0.3 | 35 | 7.2 | 100 |
| T10 |  |  |  |  |  |  |  |

AT = Amyloid tau (APP$^{SWE}$-Tau);
T = Tau;
WW = Wild/wild;
A = Amyloid (APP$^{SWE}$)

TABLE 6

Samples isolated from 200 μl blood of 5M AD mice

| Mouse | PBMC RNA Concentration ng/μl | Plasma RNA Concentration ng/μl | RNA total volume (μL) | PBMC Protein Concentration μg/μl | PBMC Protein total volume (μL) | Plasma Protein Concentration μg/μl | Plasma Protein total volume (μL) |
|---|---|---|---|---|---|---|---|
| WW1 | 18.8 | 187.8 | 20 | 1.8 | 40 | 6.0 | 300 |
| WW2 | 23.6 | 44.9 | 20 | 1.9 | 40 | 3.1 | 300 |
| WW3 | 46.5 | 29.8 | 20 | 1.1 | 40 | 8.7 | 300 |
| WW4 | 47.7 | 39.7 | 20 | 2.9 | 40 | 3.2 | 300 |
| WW5 | 20.0 | 40.4 | 20 | 1.2 | 40 | 2.9 | 300 |
| A2 | 26.9 | 47.8 | 20 | 1.7 | 40 | 4.1 | 300 |
| A3 | 25.9 | 131.8 | 20 | 1.3 | 40 | 3.4 | 300 |
| A4 | 71.1 | 75.5 | 20 | 1.9 | 40 | 8.2 | 300 |
| AT-1 | 26.4 | 72.6 | 20 | 1.6 | 40 | 8.1 | 300 |
| AT-2 | 11.5 | 37.8 | 20 | 1.1 | 40 | 7.8 | 300 |
| AT-3 | 73.3 | 67.9 | 20 | 2.1 | 40 | 2.7 | 300 |
| AT-4 | 18.8 | 45.6 | 20 | 2.8 | 40 | 3.3 | 300 |
| AT-5 | 116.9 | 63.0 | 20 | 0.9 | 40 | 5.7 | 300 |
| T6 | 74.9 | 56.1 | 20 | 2.2 | 40 | 7.0 | 300 |
| T7 | 52.9 | 70.0 | 20 | 1.4 | 40 | 1.8 | 300 |
| T8 | 34.6 | 192.7 | 20 | 1.2 | 40 | 3.4 | 300 |
| T9 | 55.6 | 38.1 | 20 | 2.0 | 40 | 7.0 | 300 |
| T10 | 20.1 | 82.9 | 20 | 1.1 | 40 | 8.0 | 300 |

AT = Amyloid tau (APP$^{SWE}$-Tau);
T = Tau;
WW = Wild/wild;
A = Amyloid (APP$^{SWE}$)

TABLE 7

Samples isolated from 200 μl blood of 6M AD mice

| Mouse | PBMC RNA Concentration ng/μl | Plasma RNA Concentration ng/μl | RNA total volume (μL) | PBMC Protein Concentration μg/μl | PBMC Protein total volume (μL) | Plasma Protein Concentration μg/μl | Plasma Protein total volume (μL) |
|---|---|---|---|---|---|---|---|
| WW1 | 30.3 | 28.8 | 20 | 0.5 | 90 | 7.1 | 300 |
| WW2 | 35.3 | 32.8 | 20 | 0.4 | 90 | 9.0 | 300 |
| WW3 | 160.6 | 38.3 | 20 | 1.6 | 90 | 17.7 | 300 |
| WW4 | 103.6 | 32.3 | 20 | 0.6 | 90 | 14.1 | 300 |
| WW5 | 77.1 | 9.5 | 20 | 0.6 | 90 | 8.2 | 300 |
| A2 | 40.6 | 11.0 | 20 | 0.3 | 90 | 10.4 | 300 |
| A3 | 35.7 | 34.7 | 20 | 0.7 | 90 | 8.5 | 300 |
| A4 | 24.1 | 7.9 | 20 | 0.8 | 90 | 16.7 | 300 |
| AT-1 | 39.1 | 24.8 | 20 | 0.5 | 90 | 9.6 | 300 |
| AT-2 | 30.7 | 28.9 | 20 | 0.2 | 90 | 15.9 | 300 |
| AT-3 | 74.9 | 25.5 | 20 | 1.1 | 90 | 7.9 | 300 |
| AT-4 | 31.4 | 19.1 | 20 | 0.4 | 90 | 10.2 | 300 |
| AT-5 | 77.6 | 43.9 | 20 | 0.7 | 90 | 16.1 | 300 |
| T6 | 34.4 | 31.5 | 20 | 0.8 | 90 | 9.1 | 300 |
| T7 | 37.5 | 13.1 | 20 | 0.3 | 90 | 6.6 | 300 |
| T8 | 32.0 | 11.1 | 20 | 0.5 | 90 | 9.8 | 300 |

TABLE 7-continued

Samples isolated from 200 µl blood of 6M AD mice

| Mouse | PBMC RNA Concentration ng/µl | Plasma RNA Concentration ng/µl | RNA total volume (µL) | PBMC Protein Concentration µg/µl | PBMC Protein total volume (µL) | Plasma Protein Concentration µg/µl | Plasma Protein total volume (µL) |
|---|---|---|---|---|---|---|---|
| T9 | 47.2 | 17.5 | 20 | 0.3 | 90 | 11.9 | 300 |
| T10 | 74.1 | 15.8 | 20 | 0.5 | 90 | 16.2 | 300 |

AT = Amyloid tau (APP$^{SWE}$-Tau);
T = Tau;
WW = Wild/wild;
A = Amyloid (APP$^{SWE}$)

As shown in these Tables, sufficient sample quantities are obtained for processing for RNA & polypeptide isolation, to qPCR and polypeptide abundance assays in these two biological samples, to eventual data analysis, storage and interpretation. RNA isolated from PBMC and plasma of mice for each survival bled sample has been processed to quantify miRNA expression by real time PCR (qPCR), using pre-defined target stem loop primers specific for this miRNA sequence with Taq-Man MicroRNA Assays (Applied BioSystems, Foster City, Calif.). This is a sensitive, two-step quantitative reverse transcriptase (TaqMan MicroRNA RT kit) and PCR reaction (TaqMan Fast Universal PCR, No AmpErase UNG), which quantifies only mature miRNAs, the functional unit of this noncoding RNA species. Positive controls include constitutively expressed small RNA reference genes, such as small nucleolar RNAs (i.e. RNU24 and U6 snRNA). Negative controls include quantifying a microRNA not expressed in mice (i.e. cellsy6), and a blank control without RNA template. All PCR assays are amplified in triplicate for individual specimens from each animal, yielding 3 data points X number of animals used for each specimen type in individual mouse groups, i.e. 3 AD Tg mice and their controls, or SAMP8 and their controls. These quantitative PCR (qPCR) results are calculated by the delta $C_T$ method, using differences in $\Delta C_T$ values between the specific miRNA and a small RNA reference gene [183]. Fold changes are estimated by comparative analysis, using the average $C_T$ values from each group for inter-animal and inter-group comparison, and expressed as box plots. Fine-tuning the qPCR assay allows us to estimate a range from 2 to 10 million copies per unit of blood volume. Approximate 200 µl of blood can be serially collected from the submandibular facial vein, yielding both PBMC and plasma RNA specimens, with RNA integrity numbers>8 for the former, and peaks at the 0-150 nt region for the latter since they do not contain the 28S and 18S RNA species [184]

For measuring the target polypeptide level in the same samples, we used quantitative Western blotting. Here, to minimize work-load burden-associated human errors, we process polypeptide specimens of all 3 AD Tg mutants and controls, and SAM P8 and controls, as one set; repeats of animals for each group provide more than triplicate data for statistical analysis. This design is planned to avoid inter-gel variation in Western analysis; it uses protocols optimized in our laboratory, and has produced preliminary results with minimal background noise and accurate antigenic detectability. We find antibody to β-actin to be a preferable loading control for calculating target polypeptide/β-actin ratios in PBMC samples; since β-actin is not found at stable levels in the plasma polypeptide pool, we used constant Ponceau red staining as our loading control here. (An added step is the use of affinity columns to remove plasma serum albumin; we succeed in reducing its abundance to <10%.) Negative controls such as minus primary antibody and normal serum are also employed. Intensities on Western blots are quantified by a computer image scanner system, allowing us to determine levels of polypeptide bands for each blot, calculated as a ratio to the tubulin band, or major band intensity for plasma polypeptide samples. Averages of triplicate blots provide the target expression index for each animal of each age group.

Establishing the Biorepository of Survival Bled Samples:

The survival bleeding program was begun with senescence-accelerated mice (SAMP8) and control strain SAMR at 3 months of age, and AD transgenic strains, APP$^{swe}$, Tau, APP$^{swe}$/Tau, and wild-wild (WW) control for both APP and Tau mutant strains, at 4 months. This contributes to our biorepository six consecutive survival-bled specimens, separated into PBMC and plasma fractions, as shown in Table 3. For the senescence-accelerated mouse strain, although literature reports their life span to be 12 months, the mice used in our study already show extreme old age syndrome, i.e. loss of hair, hair coat not smooth with yellowish tint, and significant decrease of mobility and food intake. Thus, the final bleeding was at 8 months of age, with sacrifice so that tissues of brain, liver, spleen, kidney, muscle, skin, bone, heart, and testes were collected, and stored with the bled PBMC and plasma samples. For the AD transgenic mouse strains, the bleeding program was implemented at 4 months of age, due to the fact that these mice are fragile and were not shipped from the vendor to our facility until they were >3 months old; thus the first possible bleeding was at 4 months. Unfortunately, for the APP$^{swe}$ group, one of the three mice died due to animal care error; this strain only has 2 mice after the fourth bleeding. Nonetheless, we have four complete bleeding cycles up to 7 months for the AD transgenic mouse strains, and six complete bleeding cycles for the SAMP8 and SAMR1 strains. Since both SAM P8 and the AD-Tg mouse strains manifest initial signs of amyloid-positive structures in brain at 6-7 months old, we have at least two bled cycle samples for the AD mouse strains, and five samples for the SAMP8/SAMR1 strains. These samples are of particular interest, because data obtained from them will indicate invaluable pre-symptomatic blood-based biomarkers before gross brain histochemical disorders and behavior changes are observed.

Polypeptide Characterization of Survival Bled Blood Specimens:

Survival bled samples of 4-6 month old AD transgenic mouse strains were studied for plasma levels of target polypeptides of miR-34a and miR-34c, and two other downstream genes, Cdk4 and Aβ42; we used three animals per group for statistical significance tests. These values were used to measure: a. Strain progression biomarker expression during this time window; b. comparative analysis between tested mice and controls: SAMP8 vs. SAMR1; APP$^{swe}$ vs. wild-type; Tau vs. wild-type, APP$^{swe}$/Tau vs. wild-type; and c. cross-Tg strain comparison, esp. APP$^{swe}$ vs. Tau, or single Tg vs. double Tg mutants, i.e. Tau vs. APP$^{swe}$/Tau, etc.

Western blotting analysis of 4-6 month old plasma specimens from AD transgenic mouse strains was performed for Bcl2, Onecut2, Presenilin 1, Cdk4 and Aβ42 and is shown in panel A of each of FIGS. 44-48. As described earlier, β-actin levels normally used as loading standard cannot be used for plasma Western blotting assays; we instead used Ponceau red-stained bands, which show constant staining intensities across all lanes within a gel-transferred polypeptide membrane. All western blot Figures show three representative animals' blotting results for each strain; antibody intensities for each of the three animals are quantified by image analysis, as described above. The average of the intensities is then used for histogram plotting, as shown in Panel B of each of FIGS. 44-48, while Panel C shows immunoblot images of the specific polypeptide bands detected by their designated antibodies for all three animals used per mouse strain. Presentation of three animals for each of the bleeding cycles, i.e. 4, 5, & 6 month old bled samples, allowed us not only to determine inter-animal differences within a mouse strain across these three age groups, but also to compare the same age groups across the four mouse strains. As shown in FIG. 44(A)-(D), Bcl2 polypeptide levels are maintained in all three age groups from 4-6 months in wild-wild type controls, but not in the three AD transgenic mouse strains. Interestingly, Tau-Tg mice show lower levels of Bcl2 polypeptide at 4 months, and also decrease at a much steeper rate than the other two AD Tg mice. Nonetheless, all three mouse strains show significantly reduced levels of circulating Bcl2 polypeptide at 6 months old. Similar trends of decrease in circulating levels from four to six months are also seen in Onecut 2 (FIGS. 45(A)-(D)) and Presenilin1 (FIG. 46(A)-(D)) polypeptides, with no detectable decrease in the wild-type control. Differing from the Bcl2 polypeptide levels' decrease, both Presenilin 1 and Onecut2 levels decrease as early as the first bled samples; the 4-month old samples with $APP^{swe}$ show lowest levels of Presenilin 1 and Onecut2, followed by the Tau mice, with the double transgenic mice exhibiting reduced levels slightly above the two single transgenic mouse strains.

Interestingly, although Cdk4 (FIG. 47) is a candidate target polypeptide of miR-34a or miR-34c, its level is surprisingly and unexpectedly increased. This result suggests that our findings concord with the literature report that Cdk4 up-regulation is observed in Alzheimer's disease [185,186], and this gene is therefore likely not a target functionally silenced by miR-34x.

Along with decreased Bcl2, Psen1, and Onecut2 in the same plasma samples is a corresponding increase of Aβ42 (FIG. 48(A)-(C)), starting at 4 months for mutants bearing Tau-hyperphosphorylation and the double transgenic carrying both Tau and APP mutations, while the transgenic mutant bearing APP alone shows significant difference only at 6 months of age.

Figure 49:
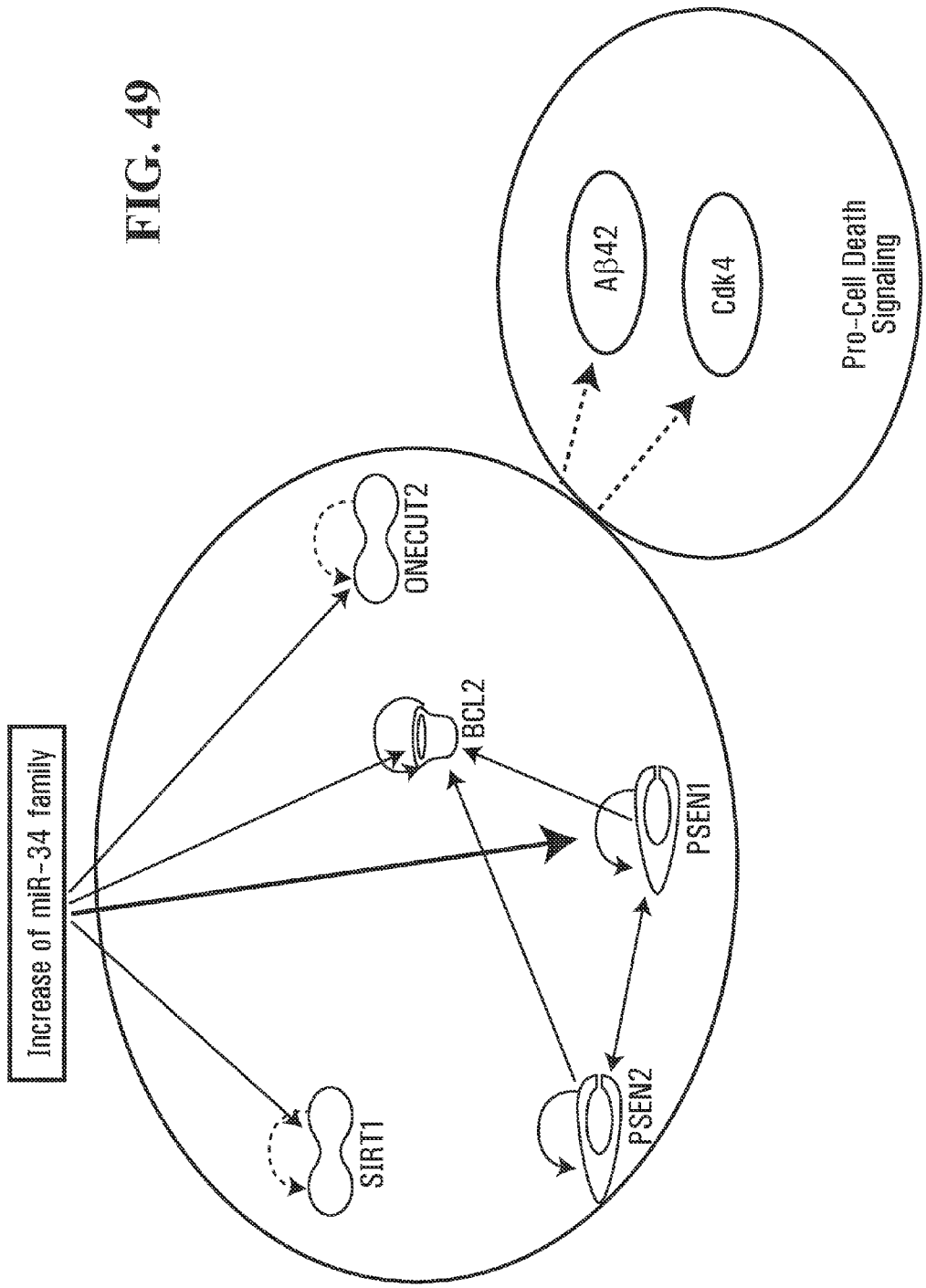
FIG. 49: Schematic showing a non-limiting illustration that proposes a working model for the observed decrease of Bcl2, Presenilin 1 (PS1 or PSEN1), and Onecut2 and increase of Cdk4 and Aβ-42 levels in plasma of transgenic mouse mutants bearing the AD-mutations and the increase of miR-34 family plasma level and the increase of cell death signalling.

In conclusion, plasma polypeptide level from survival bled blood specimens show that: 1. Polypeptide-based biomarkers can be tracked consistently within the same animals, and the trends can be used for changes before or at the time observed in brain; 2. the changes in the increase of Onecut2, Bcl2, and Psen1 suggests the increase of miR-34 family members, since all three are their known target genes; and 3. the increase of Cdk4 and Aβ42 suggest a downstream effect of increased pro-cell death signalling, as illustrated in FIG. 49.

Increased microRNA in Plasma Specimens as Early as 4 Months in Accelerated Aging SAMP8 Mutant and AD Tg Mouse Mutants:

Quantitative PCR (qPCR) analyses were performed with RNA samples isolated from survival bled blood plasma from 4 to 12 months old for AD Tg mice, and from 4-8 months for SAMP8 mice, with the last monthly survival bleeding denoting extreme old age for each of these two mutant mice. Three animals were used from each age group selected for the study; for those of 4-6 month old survival bled samples, the qPCR and polypeptide analyses were done with specimens from the same animals.

Figure 50:
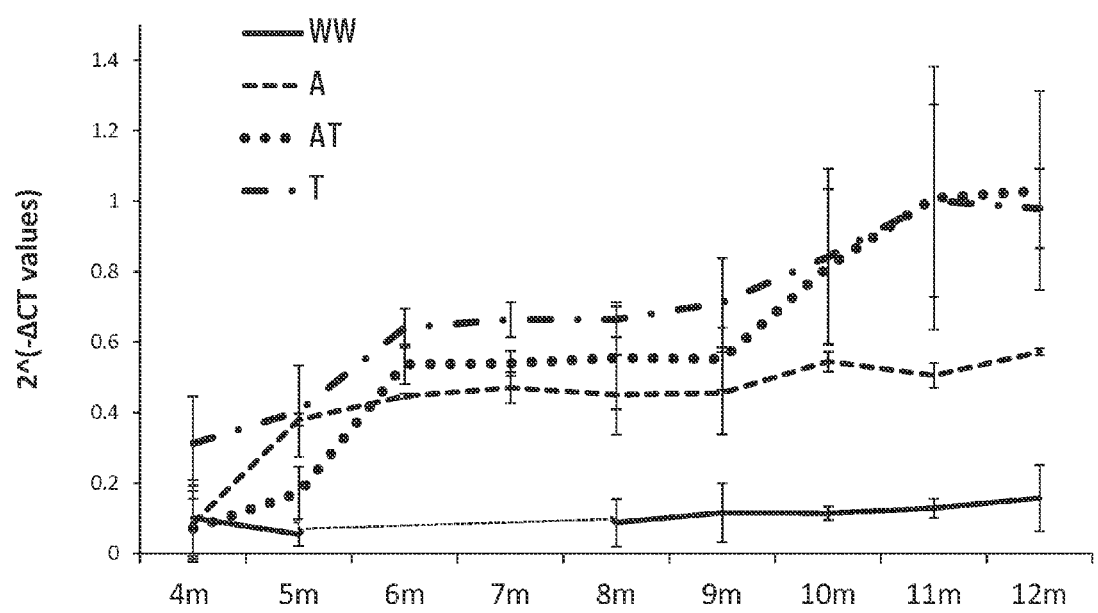
FIG. 50: Age-dependent increased levels of miR-34a in plasma samples of AD transgenic (Tg) mice assayed by qPCR. (n≥3; three different animals were used from each age group selected for the study) compared with their control counterparts. (ww: control for all three Tg mice; A: APP$^{SWE}$ mice; T: Tau hyperphosphorylation mice; AT: double transgenic carrying both APP$^{SWE}$ mutation and hyperphosphorylated Tau.) (m=month.)
Figure 51:
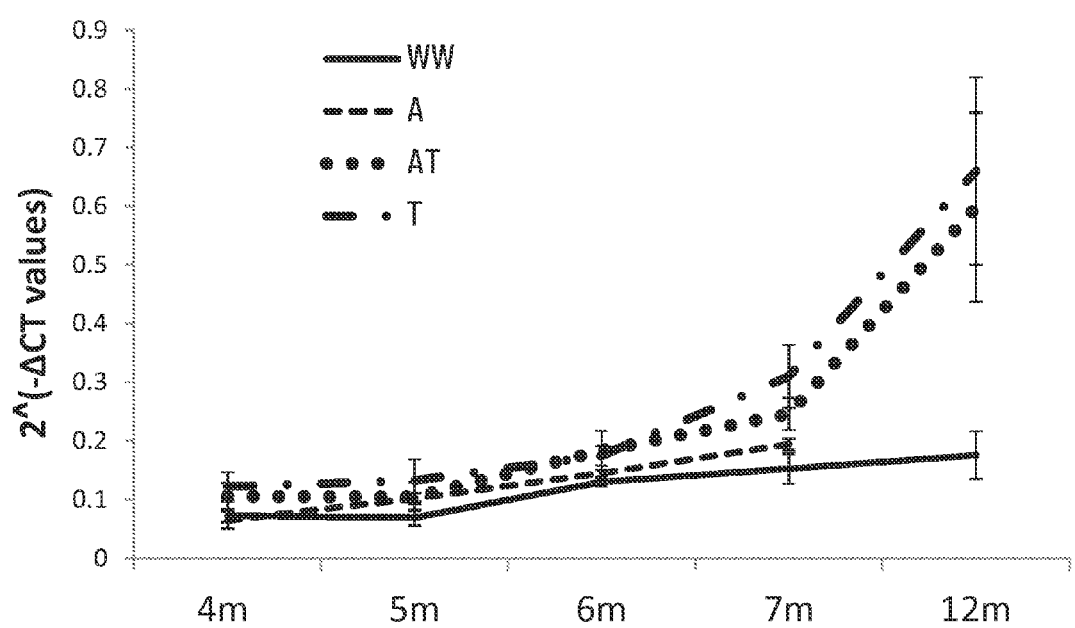
FIG. 51: Age-dependent increased levels of miR-34c in plasma samples of AD transgenic (Tg) mice assayed by qPCR. (n≥3; three or more different animals were used from each age group selected for the study) compared with their control counterparts. (ww: control for all three Tg mice; A: APP$^{SWE}$ mice; T: Tau hyperphosphorylation mice; AT: double transgenic carrying both APP$^{SWE}$ mutation and hyperphosphorylated Tau.) (m=month.)
Figure 52A:
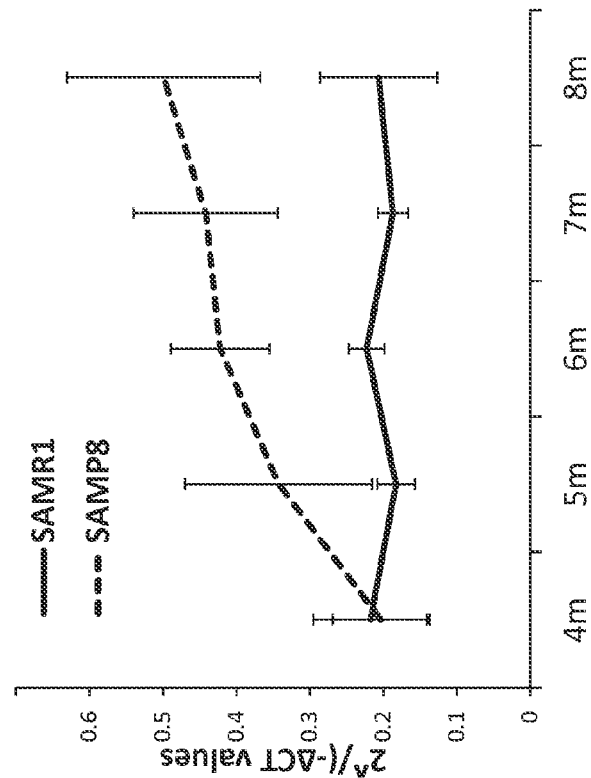
FIG. 52: Age-dependent increased levels of miR-34a (Panel A) and miR-34c (Panel B) in plasma samples of SAMP8 comparing to their control counterparts (SAMR1) assayed by qPCR. (n≥3; three different animals were used from each age group selected for the study.) (m=month.)
Figure 52B:
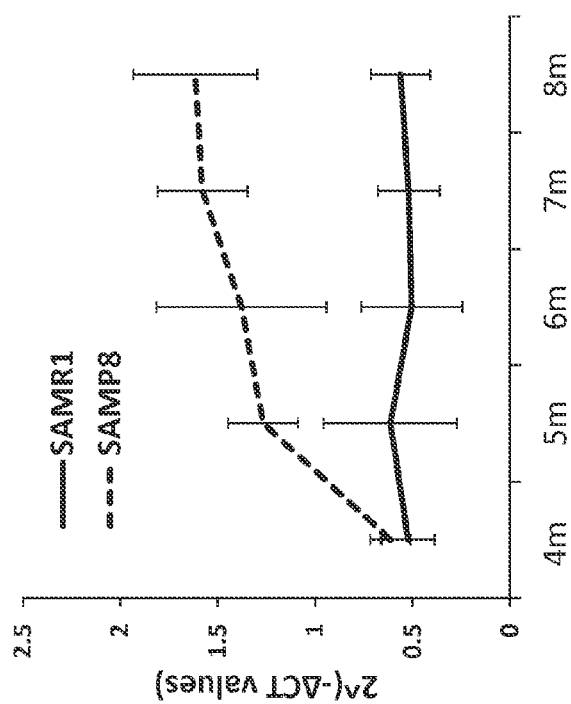

This survival bleeding study shows that from birth, Tau transgenic mice already have higher miR-34a at 4 months of age, and by 5 months, all three transgenics, $APP^{SWE}$, T, and double transgenic $APP^{SWE}$+T show higher miR-34a than wild-type controls (WW) (FIG. 50). This increase continues to 6-12 months of age. A similar increase at 5 months, continuing through the rest of the life span until 12 months old, is also seen in miR-34c expression in monthly blood samples from 4 till 12 months of age (FIG. 51). In the accelerated aging SAMP8 mutant mouse strain, we have only collected survival blood samples till 8 months of age, the median life span for these animals before mortality-associated pathology sets in. FIG. 52 shows miR-34a and miR-34c expression from 4 to 8 month old survival-bled SAMP8 specimens; again, significant increase of these two microRNAs' expression is evident by 5 months of age.

In summary, all these analyses of RNA samples isolated from survival-bled plasma from 4 to 12 months are presented graphically as expression levels of miR-34a & miR-34c using quantitative PCR, represented as $2^{\wedge}(-\Delta C_T)$ values from their individual box plot values. As described above, the age groups included for SAMP8 and SAMR1 are from 4 to 8 months. Panels A and B of FIG. 52 show expression levels of miR-34a and miR-34c in 4 to 8 month old mice (n≥3; three or more different animals were used from each age group selected for the study); the graphical representation of expression levels of these two microRNAs are derived from quantitative PCR data, giving rise to the $2^{\wedge}(-\Delta C_T)$ values as box plots for plasma samples.

In summary, the results demonstrate that increases in level of two microRNAs, miR-34a and miR-34c, are indeed observed as early as 5 months of age in all three transgenic AD model mouse strains and SAMP8, compared with the respective control mouse strains. Among all strains studied so far, the increase in the transgenic mouse model carrying the hyperphosphorylation mutation is the most significant. This increase is most dramatic, even as early as 4 months of age, the earliest time point available for our study. In all strains, increased level of miR-34a and miR-34c is observed at 5 and 6 months of age, and then levels off in strains carrying the $APP^{SWE}$ mutation. This levelling off of the increase of the two microRNAs from 6 months onward is only observed until 9 months of age, with yet another increase after this age in two transgenic mouse lines, the one carrying the Tau phosphorylation mutation and the double transgenic mutants bearing both Tau and APP mutations. In the SAMP8 strain, this increase starts at 5 months and continues to rise until the end, i.e. 8 months.

Figure 53:
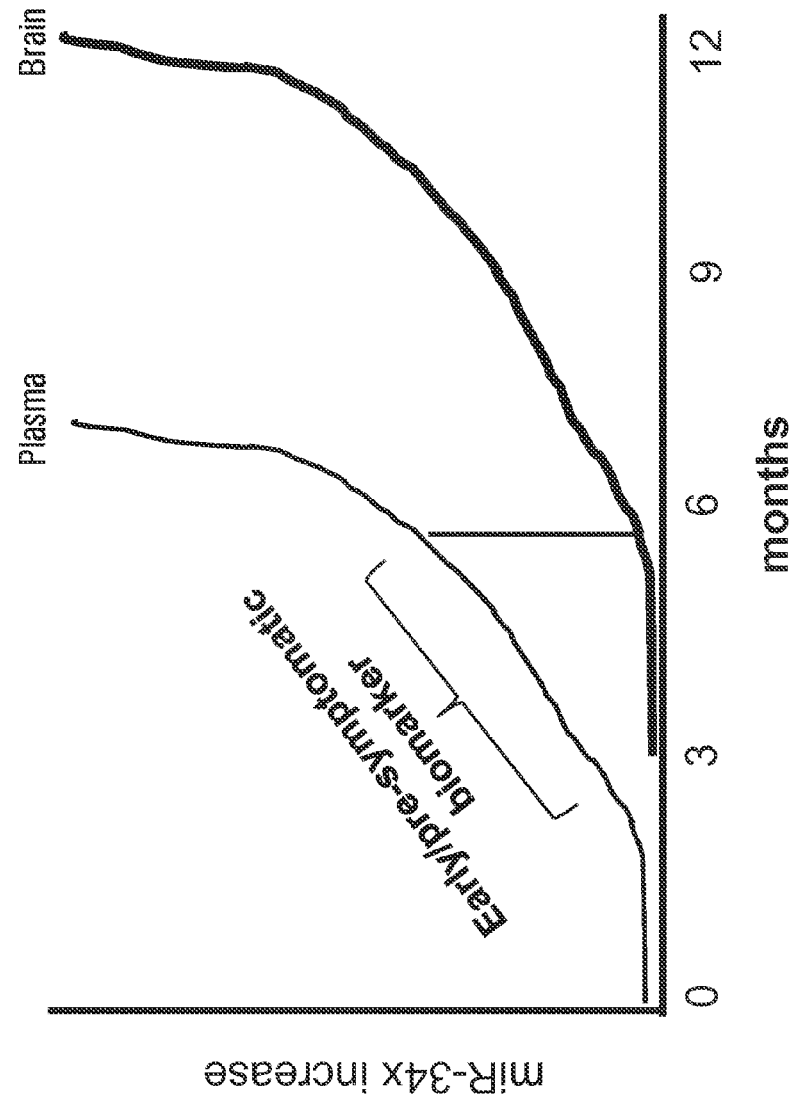
FIG. 53: Schematic showing a non-limiting illustration of the use of plasma miR-34× level increase as an early/pre-symptomatic biomarker for its increase in brain.

In conclusion, the results of our survival bled samples suggest the following:

Survival bleeding specimens can be obtained from the same individual mice at early, intermediate, and late life stages of strains modeling familial Alzheimer's disease and accelerated aging;

Survival bled samples show valuable pre-symptomatic biomarkers represented by circulating microRNAs, before the earliest detectable brain pathology presentation (FIG. 53);

Early detection of abnormal level increases of miR-34a and miR-34c constitutes a guide for human study for early detection of an age-related symptom, such as Alzheimer's disease, by pre-symptomatic biomarkers, because of the possibility of studying temporal kinetics of efficacy in the same individual animals, without concern over inter-animal variation; and Low animal cost with smaller animal colony size, without sacrificing animals for each time point study.

A major roadblock to overcome the current severe shortage of pipeline drugs for age-dependent disease therapeutic development is the cost of supporting large animal colonies required by long-term experimental design, sacrificing many animals at multiple time points to evaluate drug effects evident as late as 10-12 months of age, for example when mouse brain develops the full manifestation of plaque and tangle deposits. Adapting the survival bleeding method, serial blood samples can be obtained from mice, avoiding the invasive use of the retro-orbital vein or cardiac puncture at euthanasia. This protocol allows us to obtain ~200 µl of blood from the submandibular vein, a procedure not requiring anaesthesia, with rapid healthy recovery with minimal invasiveness. From these 200 µl blood specimens, we can process blood mononuclear cells (PBMC) and plasma samples for RNA and polypeptide isolation, in sufficient quantities for both qPCR assays and Western blotting for measuring levels of microRNAs and their target polypeptides. The herein described survival bleeding for blood microRNA biomarkers supports:
1) Analyzing the same set of animals at multiple time points, a true temporal kinetic evaluation for efficacy;
2) Longitudinal intra-animal studies, a prelude to individualized mouse efficacy testing without inter-animal variation (requiring many fewer animals without multiplying the number of animals needed per time point due to euthanasia).

Figure 54:
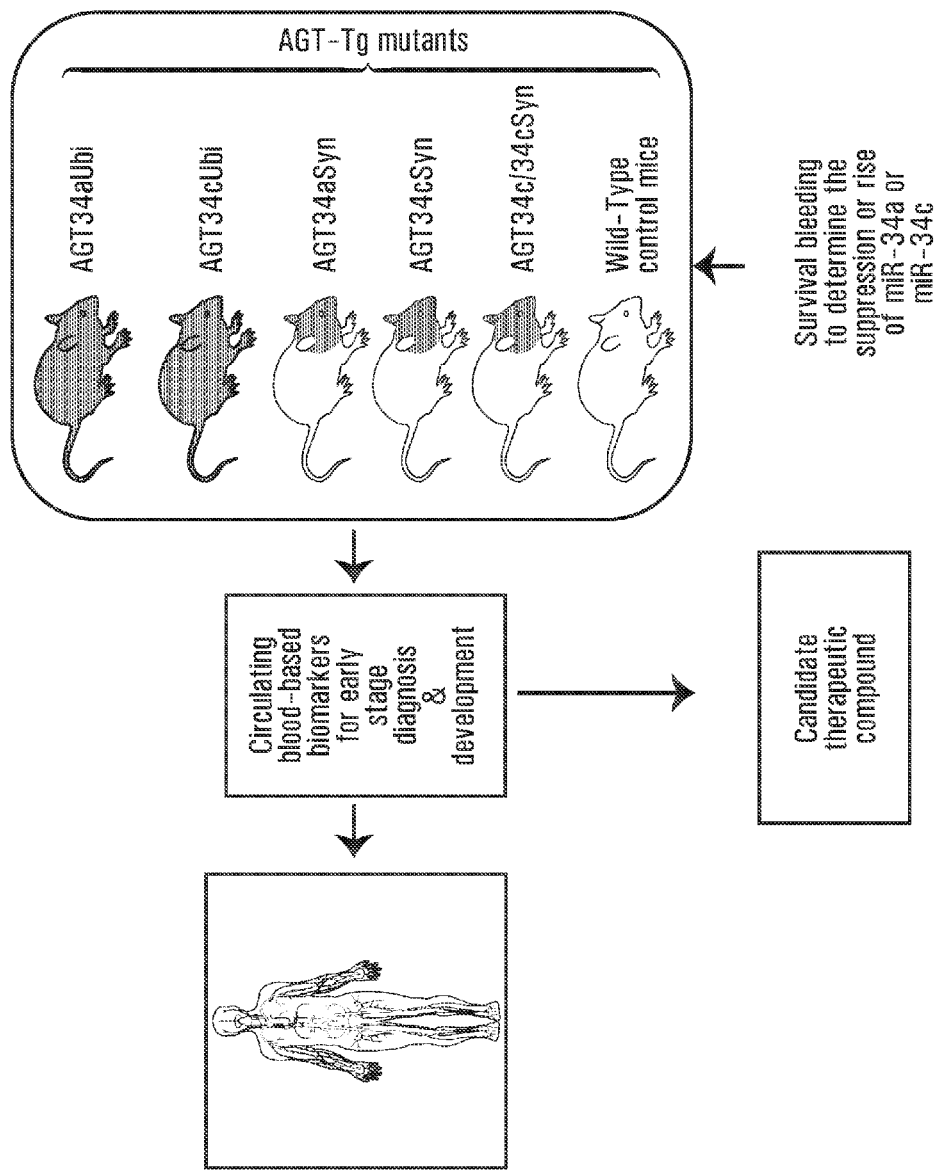
FIG. 54: Schematic showing a non-limiting illustration of the use of survival bleeding protocol for candidate therapeutic compound screening assay using embodiments of the herein described non-human transgenic models.
Figure 55:
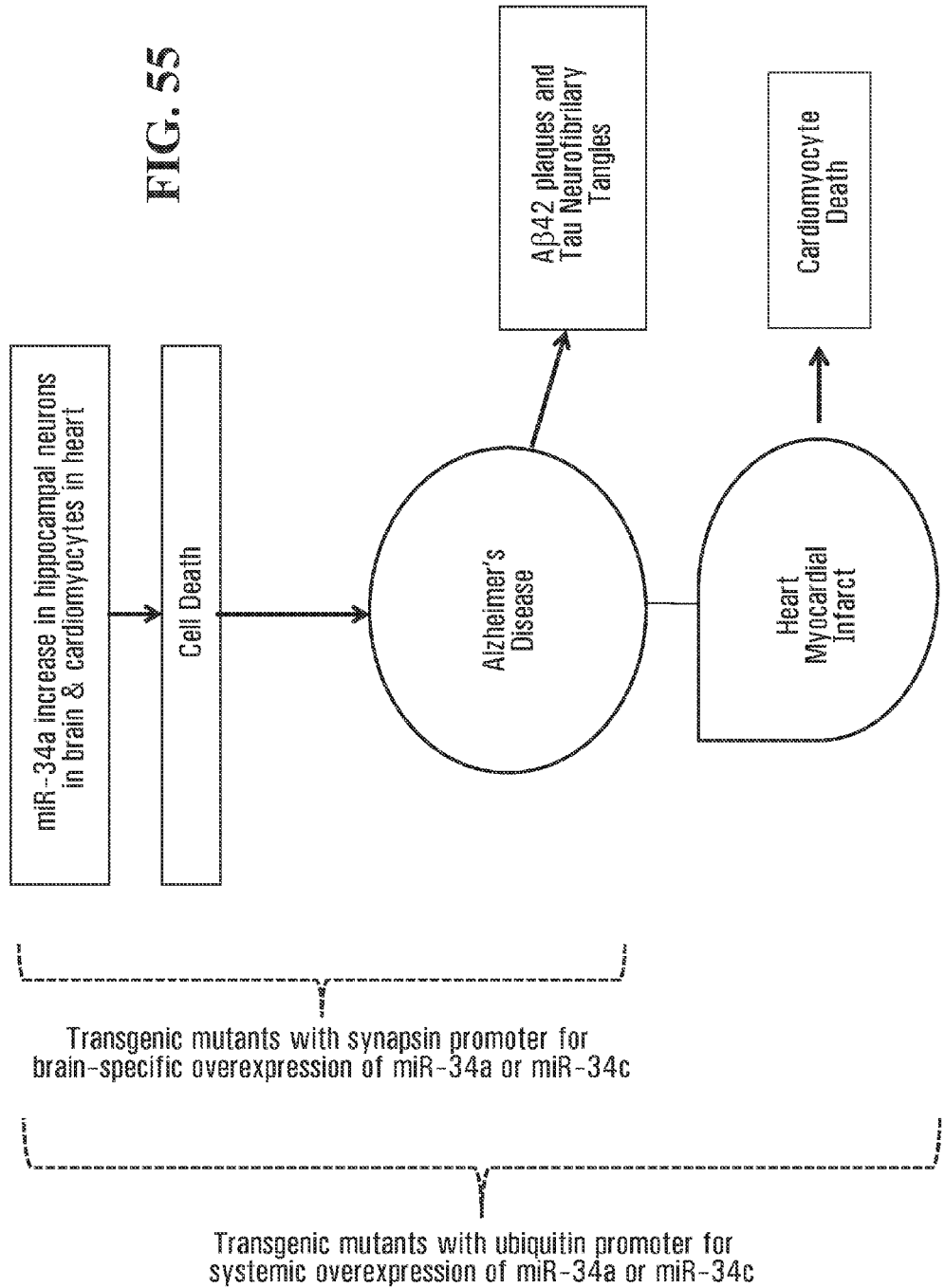
FIG. 55: Schematic showing a non-limiting summary of the herein described miR-34a and miR-34c knock-in impact on heart and brain disease.

Combining the herein described survival bleeding methodology with the herein described transgenic non-human animals overexpressing either miR-34a or miR-34c, in particular the herein described five transgenic mouse mutants listed in Table 1, renders feasible the herein described screening assays for selecting anti-accelerating and/or anti-age-related disease (or symptom) candidate therapeutic compound (FIGS. 54 and 55). The present invention may also be useful for overcoming the current severe shortage of pipeline anti-age-related therapeutic compounds, such as anti-AD and/or for anti-myocardiac infarction, because it involves:
  Applicability to future human application for AD disease staging: Linking early, intermediate and late AD staging in animal models to early and late MCI and bona fide AD (see PCT/US2012/049971);
  Non-invasive analysis of brain and/or heart dysfunction by circulating microRNA qPCR assays;
  Compatible technical assays, with miR-34a, miR-34c and other microRNAs conserved between man and mice; and
  Lower animal costs with smaller animal colony size, supporting temporal kinetics of efficacy in the same animal cohorts, by means of survival bleeding.

6. Discussion

The current research in the microRNA area may be summarized as: 1. a single microRNA may silence many key genes, or 'hubs' of various signalling pathways; 2. an individual target message may be targeted ('dimmed') by several microRNAs acting on it; 3. >1200 human miRNAs have been identified; 4. selected microRNAs are conserved from plants to humans, with species-specific ones emerging for unique signalling pathways; 5. microRNAs' genomic locations are often clustered as polycistronic transcription units; 6. Mapping of microRNA genomic clusters and their target binding sites reveals significant single nucleotide polymorphisms (SNP) for key phenotype manifestation [14-17]; 7. Some miRNAs are cell type-specific, e.g. neuron-specific miRNAs dictate a neuronal lineage [18.19]; and 8. MicroRNAs are regulated by their own specific promoters; individual microRNAs have their own promoters, and can be regulated by their own target polypeptide products in feedback loops [20-23].

So far, work in cancer [24-27] may be summarized as: 1. causes of miRNA modulation in cancer resemble familiar genetic abnormalities, i.e. mutations, deletions, amplifications, and re-arrangement of genomic composition of both miRNAs and the binding domains of their target genes; 2. germline mutations in miRNAs are associated with familial cancers; 3. miRNA profiles of tumours can be used to classify them as to their origins; 4. therapy and prognosis can be monitored by microRNA profiling; and 5. global microRNA expression is in general down-regulated in tumours compared with normal tissues [28,29]. Non-cancer clinical applications are fast following the cancer field, expanding beyond diagnosis to therapeutic promise. For example, in diabetes, miR-375 inhibits insulin secretion in mouse β-cells; its target is myotrophin, a polypeptide known to induce insulin granules [30]. Over-expression of miR-375 reduces glucose-induced insulin secretion, and inhibition of miR-375 has the opposite effect. Thus pharmacologically, sense or antisense analogues of distinct microRNAs may serve as novel therapeutic interventions, following the knock-in or knock-out strategy to induce or suppress their expression [31-35].

The expression of microRNAs themselves strongly resembles the transcription of genes encoding a message; i.e. each has its own promoter and transcription start site (TSS), with cis-sequence domains specific for binding to various designated transcription factor(s) (TF), including not only traditional TFs but also their co-activators and/or repressor(s). Close to half of the presently known microRNAs are clustered in polycistronic fashion with a common TSS; the final product may exceed several kb in length, composed of several primary microRNA transcripts. Some microRNA genes are embedded in the intron region of a host gene, and may be transcribed by either their own or the host TSS sites. TF binding to the TSS, precipitating successful transcription, is usually determined by the acetylation status of the transcription factors; this reveals the significance of the impact of many enzymes such as deacetylase in the regulation of microRNA expression. The microRNA 34 family or cluster is composed of 3 members, miR-34a, miR-34b and miR-34c. MicroRNA-34b and -34c are organized as a bi-cistronic transcription unit; however, although often they are up-regulated or down-regulated in unison, such as their decreases in cancer and Parkinson disease, divergent loss or increase is also observed, such as reported by Liang, et al [36].

Among all the microRNAs, miR-34a is relatively well understood, not only in terms of promoter regulation, but also by the target genes which it suppresses. The multi-target nature of any given microRNA prompts enormous effort by various bioinformatic means to predict miR/target pairs. In general, this is performed by popular algorithms, mapping either complete or partial complementarity of microRNAs and their target genes at either their coding or 3'-untranslated regions (3'-UTR). Dozens or even hundreds of targets for a given microRNA may be generated in this fashion. Despite this effort, true targets must be identified by painstaking functional validation studies. Targets of miR-34a have been validated by both bioinformatics and functional experiments to participate in three signaling pathways: 1. Bcl2 for survival/apoptosis; 2. Cdk4, Cdk6, and Cyclin E2 for growth arrest/senescence signalling; and 3. SIRT1 deacetylase for p53 or neuroprotection signaling [37-43]. Up-regulation of miR-34a may cause either repression of Bcl2 encoding mRNA, and thus apoptotic death; a decrease in the necessary cell cycle kinase, and thus cellular growth arrest and even senescence; or reduction of SIRT1 and hence a reduction of its deacetylating action on p53 or FoxO3a, required for neuroprotection (see following section for more detailed explanation).

The p53 network is involved in probably the best known tumor suppression signaling; assorted genotoxic and oxidative stresses may activate p53 expression, which in turn activates either the apoptosis pathway, through its action on the Bax/Puma dependent pathway, or the growth arrest/senescence pathway, through its action on p21 and others to inhibit cell-cycle dependent kinases and thus halt cell proliferation, etc. Interestingly, p53 is the very factor which activates both miR-34a and bicistronic miR-34b/c [44,45]. Of the three, miR-34a is most ubiquitously present in many tissues, while miR-34b & miR-34c are specifically expressed in lung [46, 47]. p53's own expression level is controlled by yet another microRNA: miR-29 down-regulates CDC42 and p85α, the co-repressors of p53; these two polypeptides' repression by miR-29 in turn leads to activation of p53 [48]. As suggested earlier, the transcription factor(s) for the expression of a given microRNA often function in a feed-back loop. Here a third party, SIRT1, is involved, whose deacetylation of p53 regulates the latter's binding to the transcription start site of miR-34a expression; this function of p53 is however dependent on the latter being acetylated, which is inhibited by SIRT1, disabling p53 by de-acetylation [49]; de-acetylated p53 reduces the transcriptional activation of miR-34a, since only the acetylated state can activate miR-34a, as shown in FIG. 1.

Mid-Life Decline (MLD) is Well-Recognized in Physiology- and Neurobiology-Based Research on Aging:

It is well known that long-lived individuals, either humans or rodents, exhibit less cognitive decline than controls (for review see ref. [58]); this background enabled the present inventor to seek out the missing link, i.e. epigenetic molecular mechanisms as the cause of MLD phenotypic manifestation. Moreover, it provided the opportunity to analyze systemic vs. tissue-specific declines, by identifying epigenomic parameters to measure qualitatively and/or quantitatively. Our results on shared vs. tissue-specific key miRNAs in brain and liver suggest that mid-life decline may be stimulated by: 1. a systemic deterioration of signaling in diverse tissues, e.g. impacted by up-regulated shared miRs, e.g. miR-34a, and 2. individual tissue functional declines regulated by tissue-specific miRs, such as miR-669c, -712, -93, -214 in liver, and miR-22, -101a, -720. -721 in brain [66]. This suggestion implies overlapping 'two-tier' MLD regulation, with systemic miRs as the unifying 'hub', connecting many "axes" of tissue-specific miRs, starting the decline at middle age.

Figure 2:
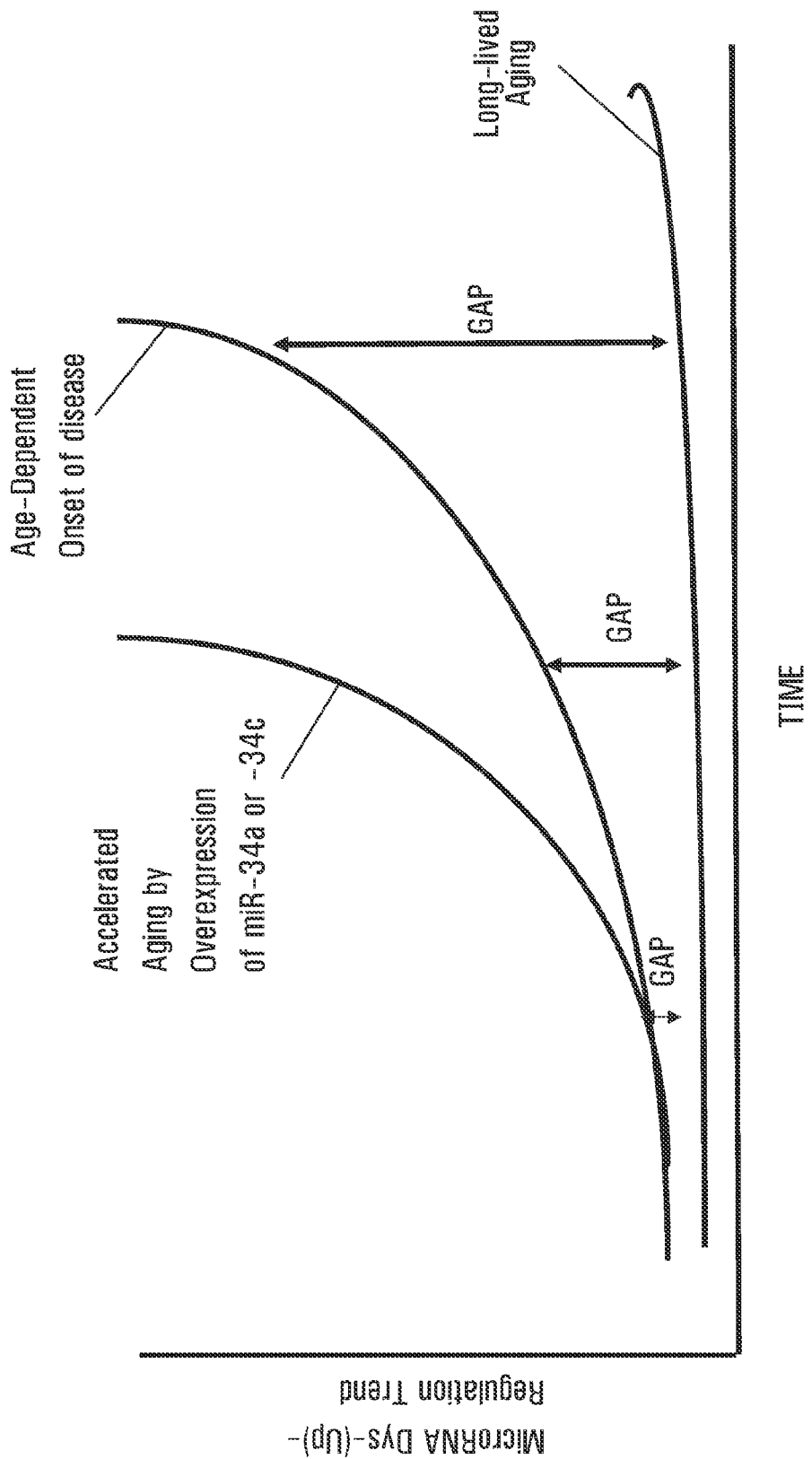
FIG. 2: Schematic showing a non-limiting illustration that proposes over-expression of miR-34a or miR-34c to accelerate the aging process, as a strategy to create a non-human animal model for accelerated aging and age-related symptom.

Accelerated Aging and Mid-Life Decline:

At present, there are at least two discussions among biogerontologists on accelerated aging, due to either the rate of aging or specific mutations. The latter involve mostly mutations in genes that cause rare syndromes such as Hutchinson-Gilford (Progeria) Syndrome or Werner syndrome; both are characterized in human victims by clinical features mimicking physiological aging at an early age [67,68]. The present approach is not to generate non-human animals modeling these two diseases, rare forms of premature aging due to specific gene mutations, such as prelamin A (farnesyl-prelamin A) in Hutchinson-Gilford (Progeria) Syndrome, or WRN helicase in the mouse model of Werner syndrome [69]; rather, we intend to create accelerated aging models of specific late-life onset diseases (or symptoms) due to increased cell death (FIG. 2). The most noted diseases involving aberrant cell survival are Alzheimer's disease and myocardial infarction; both are associated with increased cell death, the former in affected hippocampal neurons, and the latter in cardiomyocytes.

Figure 3:
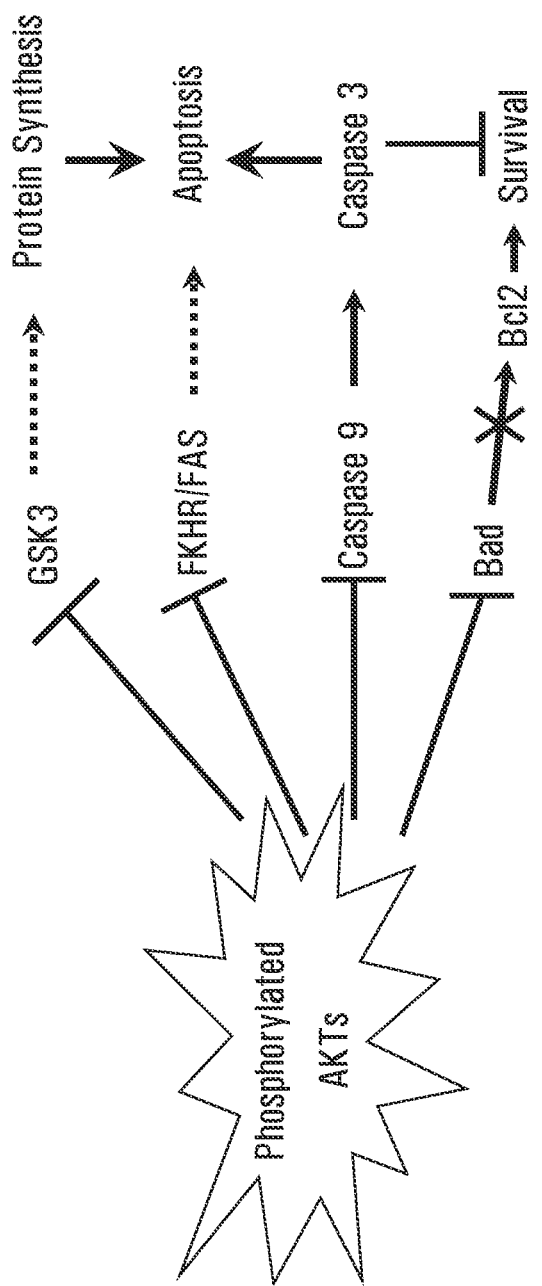
FIG. 3: Schematic showing a non-limiting illustration that proposes a working model for multifunctional Involvement of phosphorylated AKTs.

Apoptosis, Free Radical Generation and Anti-Oxidative Defense Against Cell Death:

Neurons and cardiomyocytes are well known by a common feature that they are both post-mitotic. Cells of these two types in older animals endure life-long insult of oxidative stress and with the increased rate of aging, manifested as a defence against oxygen free radicals (ROS), is weakened; continuous, lifelong free radical exposure overwhelms the cellular antioxidant capability, resulting in subsequent signalling to activate the apoptosis pathway. However, to prevent accidental triggering of apoptosis, nature has designed a Yin-Yang mechanism, with two large camps of genes fostering or hindering actual apoptotic death. Noted among the pro-apoptosis genes is a cascade action of caspases, whose proteolytic action cleaves themselves or other targeted genes. Interestingly, bcl2, the best-known anti-apoptosis survival factor, functions in an antioxidant manner by reducing lipid peroxidation or maintaining glutathione (GSH) levels by binding to GSH peroxidase, thus causally counteracting the lethal action of ROS species during apoptosis. Clearly, the oxidative pathway is linked downstream to either pro-survival or pro-cell death signalling, with the level of ROS acting as the determiner (FIG. 3). Other factors involved in this loss of oxidative defence are SIRT1 and Sirtuin. The involvement of mitochondria in generating ROS, oxidative susceptibility and defence is not covered here, but discussed in several review articles [70-73]. The two microRNAs, miR-34a and miR-34c, are both known to suppress Bcl2 and SIRT1; the overexpression of these two microRNAs in an animal may exasperate the suppression of Bcl2 and SIRT1 signalling, and thus increase the age-dependent increased loss of oxidative defence.

Cellular Senescence, Oxidative Stress and Premature Senescence:

Since the discovery in the 1960's that normal human and animal cells have a limited lifespan in culture [74-78], cultured human and mouse diploid fibroblasts have become popular in vitro cell systems to study the mechanisms of senescence, by analyzing what controls the loss of replicative potential. Extensive studies by several groups of investigators have established a parallelism between the lifespan of cultured skin fibroblasts and the age of their donors. In brief, an inverse relationship pertains between in vitro lifespan and donor age, i.e. decreased replicative capacity is observed with increasing donor age [76,77]. Replicative lifespan is genetically determined, with little or no significant difference within twin pairs, but significant differences between pairs [76]. In mouse fibroblasts, the number of population doublings (PD) is much shorter than in human cells, with most cell cultures reaching ~15 doubling levels or passage 6-7 times before they reach the senescent phenotype, acquiring large, flat "pancake" shaped cells, mostly bi- or multi-nucleated.

Findings in the investigation of molecular mechanisms determining replicative senescence so far can be summarized as: 1. permanent loss of replication is dominant, and resides on chromosomes 1, 4, 6 [79-81]; 2. c-fos is repressed and RB is not phosphorylated in senescent cells [82,83]; 3. telomere shortening is a clocking mechanism for the serial passage times needed to reach replicative senescence [84,85]; 4. cyclin-dependent kinase inhibitors p16 and p21 are abundant in senescent cells [86-88], and p16 may be the chief regulator of replicative senescence [89,90]; 5. over-expression of Ras or Raf oncogenes or cyclin-dependent kinase inhibitors may induce premature replicative senescence [91-93], which can also be induced by ceramide treatment [94] or over-expression of c-Myc-associated E-box elements [95]; 6. senescent human fibroblasts are resistant to programmed cell death [96]; and 7. the presence of p53 and RB is necessary to establish the senescent phenotype [97]. Recent discoveries show that fibroblast replicative senescence is accelerated by conditions such as UV, radiation exposure, or treatment with agents that activate stress responses in cells [92-95]; these are the same conditions often associated with physiological damage from injury. Therefore, the fact that replicatively senescent fibroblasts exist in adult and elderly tissues is bad enough in hindering the wound healing process; making it worse is the possibility that healthy cells can be accelerated to become replicatively senescent by injury conditions. Thus, individual host defences against injury, i.e. the ability to sustain a fast wound healing process, may be compromised on three fronts: 1. the existence of replicatively senescent fibroblasts; 2. remaining healthy cells being accelerated to replicative senescence; and 3. the potential to over- or under-produce fibroblast-derived factors which contribute to health disparities of wound healing and fibrotic lesion development. Premature senescence in cultured endothelial cells has been observed by overexpression of miR-34a [98].

Thus, for cells with proliferative potential such as fibroblasts, expression of miR-34a may be viewed as anti-proliferative activity, and controlling neoplastic growth and overexpression of miR-34a could induce premature senescence. Lacking miR-34a and miR-34b/c are then hallmarks of the pre-cancerous state.

miR-34 Family and Others Representing Antagonistic Pleiotropism for Age-Associated Decline:

Early life gain at the expense of late life detriment is a phenomenon called by evolutionary biologists 'antagonistic pleiotropism'. For example, the cell senescence program gains tumour suppression in early life, but persistent senescent fibroblasts resist apoptosis, as documented in our report [96], creating a later pro-tumorigenic tissue milieu [99]. MicroRNA of the 34× family may be prime examples of such a scenario: their benefit during development and young adulthood may be at the expense of late life loss of neuronal health and cognitive robustness. (See, [36] for details of miR-34 sisters' relationship, p53-directed transcriptional regulation, and SIRT-repressing activity; their absence in cancer [49, 100], and increases in aged [101], but not calorie-restricted, rodents [102] and increases in AD transgenic mice [103,104].) A contrasting scenario is reported in miR-34 knock-ins, extending life span and retarding neurodegeneration in flies [105]; a mir-34 loss-of-function mutation in C. elegans delays age-associated decline, and extends lifespan [106]. Thus, miR-34 may function both for and against longevity and neurodegeneration [107,108], depending upon contrastive functional target partnerships. Nature exquisitely designed this microRNA versatility; in mammals, the age-dependent increase may primarily direct apoptosis signalling and synaptic dysfunction in adult brain.

Among all candidate polypeptide targets, Onecut2 is a target by both miR-34a and miR-34c, followed by Bcl2, Psen1 and SIRT1, in terms of 'hits' calculated by both programs. A surprise from this analysis is the fact that Onecut2 is the most likely common candidate, compared with known survival factor Bcl2, whose repression by miR-34a to induce apoptosis and Bax up-regulation is recognized in our own papers and those of other labs [101, 102, 109, 110]. What is not clear is the link between Onecut2 and neuronal homeostasis; this gene is a member of the three-gene Onecut family, functioning as a homeo-box transcription factor (TF), most noted for its control of genes involved in hepatocyte differentiation [111]. This gene, also known as human enzyme cathepsin O [112], is regulated by bone morphogenetic polypeptide 4 (BMP4); mice lacking the Onecut2 gene lack spatial patterning, and show retrograde regulation of gene expression in sensory and spinal motor neuronal development [113,114]. Onecut2 is also involved in stimulus-induced exocytosis, as an integral part of synaptic function; Onecut2 down-regulation may increase synaptotic exocytosis [115], thus our suggestion of repressed Onecut2 impact on synaptosis signalling.

Decreased Psen1 level in transgenic and human AD plasma may suggest that this is another target polypeptide lead, based not only on reports of its role in amyloid plaque formation, but also its additional role in maintaining synaptic transport [116, 117]. This suggests a dual functional role of this polypeptide, beyond pathogenetic amyloid formation. Finally, increased Cdk4 presents another polypeptide marker lead, since Cdk4 increase is associated with increased apoptosis signalling in AD [118]. Interestingly, while Cdk4 is a known target of miR-34a [119], this functional relationship may pertain only to suppressing proliferation signalling in the context of tumour suppression, and not to inducing apoptosis signalling in our working model. This is another example of microRNA versatility, in partnerships catering to the requirements of various temporal and spatial cellular niches.

Pro- and Anti-Apoptosis Programs, Aging, and Longevity for Post-Mitotic Neurons and Cardiomyocytes:

Control of appropriate apoptotic programs has long been recognized as crucial to the aging process. However, it is important to realize that different tissues and cell types may have varying predestined programs to either promote or deter apoptotic programs, to rescue cells from death or induce them to die. These predestined programs may have molecularly tailored signalling networks functionally favouring life or death. For example, irreplaceable post-mitotic cells, such as neurons and cardiomyocytes, must survive as long as possible, while hepatocytes better tolerate committing apoptotic death, because the regenerative ability of the host tissue can readily replace cells lost thereby. Thus, but without being bound by any theory, a phenotypic manifestation of extended life span may be a weighted sum of all organs, with their respective host cells functioning optimally. The optimization of this functionality may operate in opposite modalities, such as the observation that the dwarf mutation decreases high dose insulin response in skeletal muscle, while exerting the opposite effect in liver.

Fibroblasts from long-lived dwarf mice are hallmarked by their tolerance to stress treatment; the underlying mechanism may relate to high bcl2/bax ratio functions, in the context of entire cellular signalling profiles. However, there are also reports that anti-free radical signalling such as MnSOD and Catalase increase in these long-lived mice, as well as in caloric restricted mice with extended life span. This suggests that there may be two lines of defence, a front-line defence operated by high MnSOD to counteract the oxidative assault, and a second line of defence involving the phospho-AKT anti-apoptotic signalling pathway; the low bcl2/bax ratio may be a unique design by nature for oxidative defence. The tug-of-war between pro- and anti-apoptotic controls may be key to the second line defence scenario; for neurons and cardiomyocytes, the key to survival is to maintain a high level of bcl2 expression and other associated anti-defence genes, such as SIRT1.

Anti-Oxidative Defence, Repair, and Apoptosis:

Clearly, the defence against oxygen free radicals (ROS) operates in a "tug-of-war" fashion, when a sudden burst of ROS occurs and overwhelms the cellular antioxidant capability; subsequent signalling to activate apoptosis pathways then occurs. Interestingly, bcl2, the best-known survival factor, functions as an antioxidant by reducing lipid peroxidation, or maintaining glutathione (GSH) levels by binding to GSH peroxidase, then causally counteracts the lethal action of ROS species, whose threshold levels may then stimulate signals for apoptosis. Clearly the oxidative pathway is linked downstream to either pro-survival or pro-cell death signalling, with the level of ROS determining the outcome. For the involvement of mitochondria in generating ROS, oxidative defence, aging, and apoptosis, please see reviews by Zhang and Herman [120], Martindale and Holbrook [121], and others [122-125].

The Multi-Pathway Involvement of AKT Phosphorylation:

Serine/threonine polypeptide kinase B (PKB)/AKT is the downstream effector for PI3Kinase. Inactivated AKT is unphosphorylated and localized in the cytoplasm; upon phosphorylation at threonine 308 and serine 473, the polypeptide is translocated to the plasma membrane [126,127]. The activated phosphorylated form exerts multi-inhibitory functions on several target polypeptides, as seen in FIG. 3. Phospho-AKTs inhibit Caspase 9 cleavage and therefore its activation, and cascade action on Caspase 3 cleavage and activation; therefore the PI3K/AKT pathway is known also as anti-apoptotic. What is not illustrated in FIG. 3 is that AKT functions in affecting mTOR, which through p70 S6Kinase can also regulate polypeptide synthesis, as GSK3 does.

Respiratory metabolic action in mitochondria causes by-product generation of free radicals (ROS). To contain this cost of aerobic living, Nature provides a host of antioxidant genes, primarily to convert ROS to nontoxic biochemical entities. However, incompleteness in this action causes the accumulation of non-converted ROS, thought over time to be a major factor in the aging process. Thus, longevity in many species is positively correlated with cellular anti-oxidative status, and antioxidant treatment or over-expression of antioxidant gene expression causes life span extension in fruit flies, worms and yeast, while knocking out superoxide dismutase significantly shortens the mouse life span [128-142]. Findings from the herein described cell model studies from the transgenic mouse mutants overexpressing the miR-34a or miR-34c may not only provide understanding of cellular mechanisms involved in life span determination, but may also reveal leads to long-term life-span studies in either transgenic or recombinant non-human animal mutants. These fibroblast models may become a working system as a prelude or parallel experimental strategy with studies with the herein described transgenic non-human animals.

SIRT1 and Neuroprotection:

Nicotine-adenine dinucleotide (NAD)-dependent Silent Information Regulator 2 polypeptide (Sir2), found in yeast, deacetylates both histone and nonhistone substrates [142]. In mammals, there are seven homologues. SIRT1 is the most closely related to Sir2; its functions have been linked to extending longevity in models including yeast, *Caenorhabditis elegans* and *Drosophila* [143]. It is suggested to act similarly to prolong life span in mammals. The well-known phenomenon of caloric restriction (CR) extension of life span is thought to act through increasing SIRT1 expression [144-147]. The CR effect trigger of SIRT1 is mimicked by resveratrol, a red wine polyphenol, also found in purple wine, peanuts and several other plants; CR/SIRT1 extension of longevity is also linked to improved protection against neurodegeneration in several models of Alzheimer's disease and amyotrophic lateral sclerosis [148-151]. The neuroprotective action of SIRT1 is largely due to its potent enzymatic action, deacetylating a large group of substrates including p53, liver X factor, nuclear factor κB (NFκB), Forkhead transcription factor (FoxO3a), and peroxisome proliferator-activator receptor gamma co-activator-1α (PGC-1α) [152-157]. SIRT1's relevance to neurodegeneration is best exemplified by two known signaling axes. This is by no means comprehensive for the multifaceted functions of SIRT1; nevertheless, the major function of SIRT deacetylation may render PGC-1α deacetylated, and thus able to bind to the transcription start site of a variety of mitochondrial genes including PGC-1 and NRF-1, which detoxify through the superoxide dismutase (SOD)/catalase pathway. Another SIRT1 action deacetylates FoxO3a, and thus inactivates its action of Rock transcription, which in turn increases α-secretase activity, leading to the production of soluble APPα, rather than the direction leading to $A\beta_{42}$ production. Thus, SIRT1's deacetylation of FoxO3a causes downstream channeling of APP processing in the non-amyloidogenic direction, rather than the amyloidogenic direction via γ-secretase to produce toxic Aβ.

Tau Accumulation and SIRT Reduction:

Perhaps the most exciting studies of SIRT-1 protection against neurodegeneration are those in two transgenic models; p25/AD, and mutant SOD mice for amyotrophic lateral sclerosis (ALS) [156]. p25/AD mice inducibly express a toxic co-activator of cyclin-dependent kinase 5 (p25), which develops massive forebrain neuronal loss and tau pathology [158, 159]. Resveratrol protects them from p25 toxicity via p53-dependent neuronal apoptosis, by deacetylating the latter. PGC-1α acetylation is also decreased by resveratrol; mice gain neuroprotection in terms of decreased tau pathology and cognitive decline [160-161]. Examination of cerebral cortex of AD brains shows an inverse correlation between reduced SIRT1 level and accumulation of Tau [162]. Interestingly, although the SIRT1 gene resides on chromosome 10, in a region known for high risk of late onset AD, the SNP study shows no correlation between this gene's polymorphism and disease incidence [157]. This result suggests strongly the post-transcriptional regulation of SIRT1 activity by the miR-34a/p53 axis, rendering this microRNA the most potent candidate for epigenetic regulation of sporadic AD etiopathogenesis.

SIRT1 and Cardiac Protection:

Post-infarct restoration of blood flow in the ischemic heart is suggested to be the major cause of tissue damage in ischemic myocardium, due to the massive free radical increase during the re-oxygenation process [163]. The reperfusion injury seems to be generated by mitochondria; its severity increases with age and mitochondrial dysfunction. Thus, immediately following a heart attack, cardiac reperfusion can cause many complications; tissue damage associated with this process is called myocardial reperfusion injury. Cardiomyocytes within the injured heart may undergo cell death, which causes increased risk of myocardial infarction. Therapeutic approaches to reperfusion-induced free-radical damage have largely concentrated on attempting to protect the tissues from OH* damage, either through antioxidant enzymes including superoxide dismutase and catalase, described above as the first line defence, or the use of scavengers and/or spin traps to directly remove the oxygen radicals. Nature has endowed the heart with pre-conditioning against ischemic injury during the hypoxic phase, by inducing transcription factors such as Hypoxia inducible factor (Hif)-1α; overexpression of this polypeptide results in smaller infarcts [164]. The other factor functioning as pre-conditioning protection is deacetylase polypeptide sirtuin 1, the above described SIRT1, which confers a plethora of protective function through the MAP Kinase pathway to increase ERK phosphorylation, contributing to pro-survival signaling for cardiomyocytes. Resveratrol may induce this overexpression [165], protect from ischemic injury, and consequently relieve the development of cardiac remodelling and failure. Thus, the age-dependent decline of SIRT1 may be directly or indirectly associated with cardiac resistance to ischemic pre-conditioning; therapeutic intervention to extend the sustenance of SIRT1 is a focus of preventing age-dependent reperfusion-induced injury, and thus a pro-longevity approach against myocardial infarction. However, constitutive overexpression of SIRT1 reduces cardiac function associated with dysfunctional mitochondria in mice; besides its pro-survival activity, resveratrol-induced SIRT1 may also cause myocardial hypertrophy.

Repression of SIRT1 via miR-34 family members may suppress the unwanted effect of too much SIRT1 inducing hypertrophy and dysfunctional mitochondria signalling; this program may be in balance during early life span, while with age, increased miR-34 expression in the heart may reduce baseline production of SIRT1 needed for pre-conditioning protection from ischemic injury. Since the miR-34 family is activated by p53, which is in turn activated by oxidative stress such as that during reperfusion-induced tissue response, a therapeutic strategy to inhibit all three members of this microRNA family, i.e. miR-34a, -34b, and -34c, by delivering seed 8-mer locked nucleic acid (LNA)-modified antimiR (LNA-antimiR-34), protects mice against stress-induced tissue damage by increasing expression of multiple targets [166], including vascular endothelial growth factors, vinculin, polypeptide O-fucosyltranferase 1, Notch1, and semaphorin 4B. Thus, the miR-34 family is a therapeutic target to rescue ischemic cardiac damage and provide new heart-related pro-longevity leads [166-168].

Figure 4:
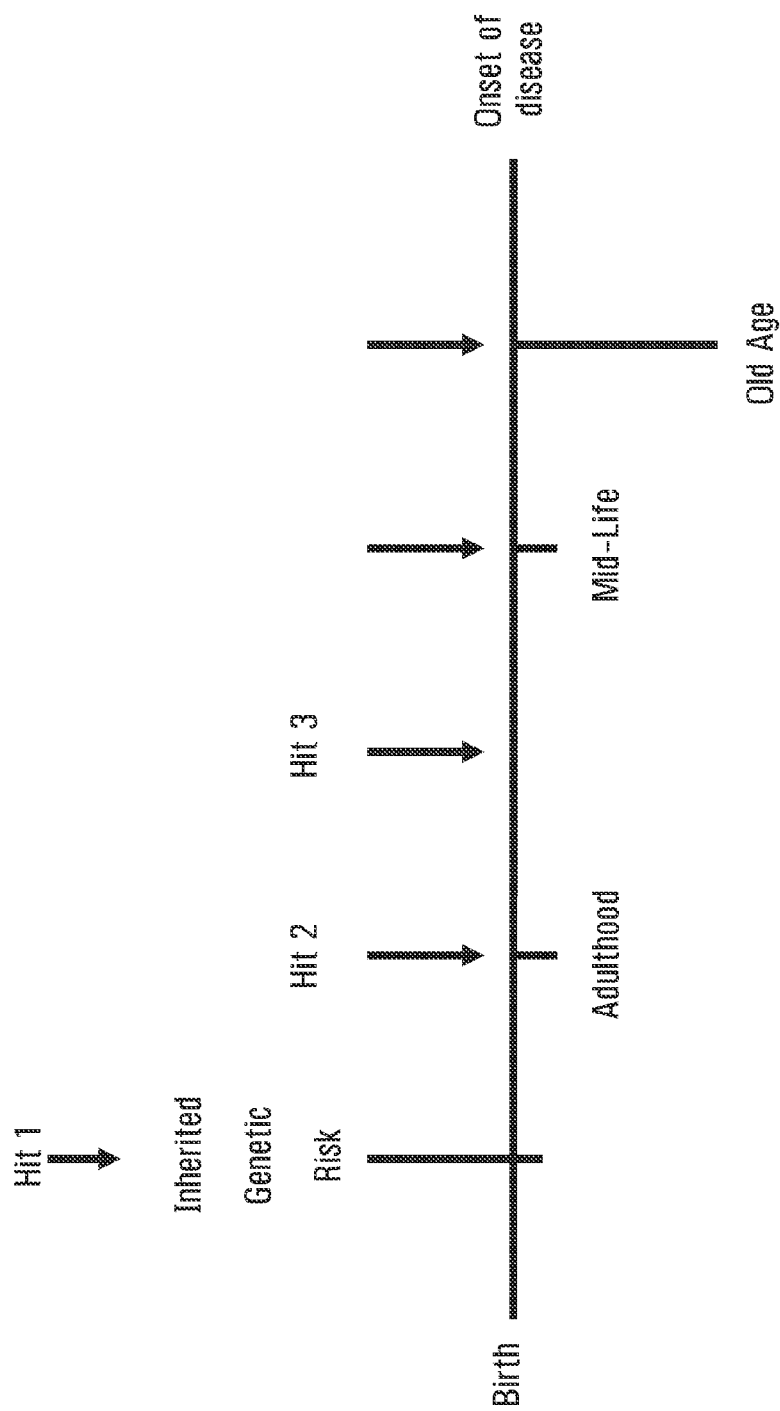
FIG. 4: Schematic showing a non-limiting illustration that proposes a working model for multi-hit gene and environmental insults, leading to age-dependent disease onset.
Figure 5:
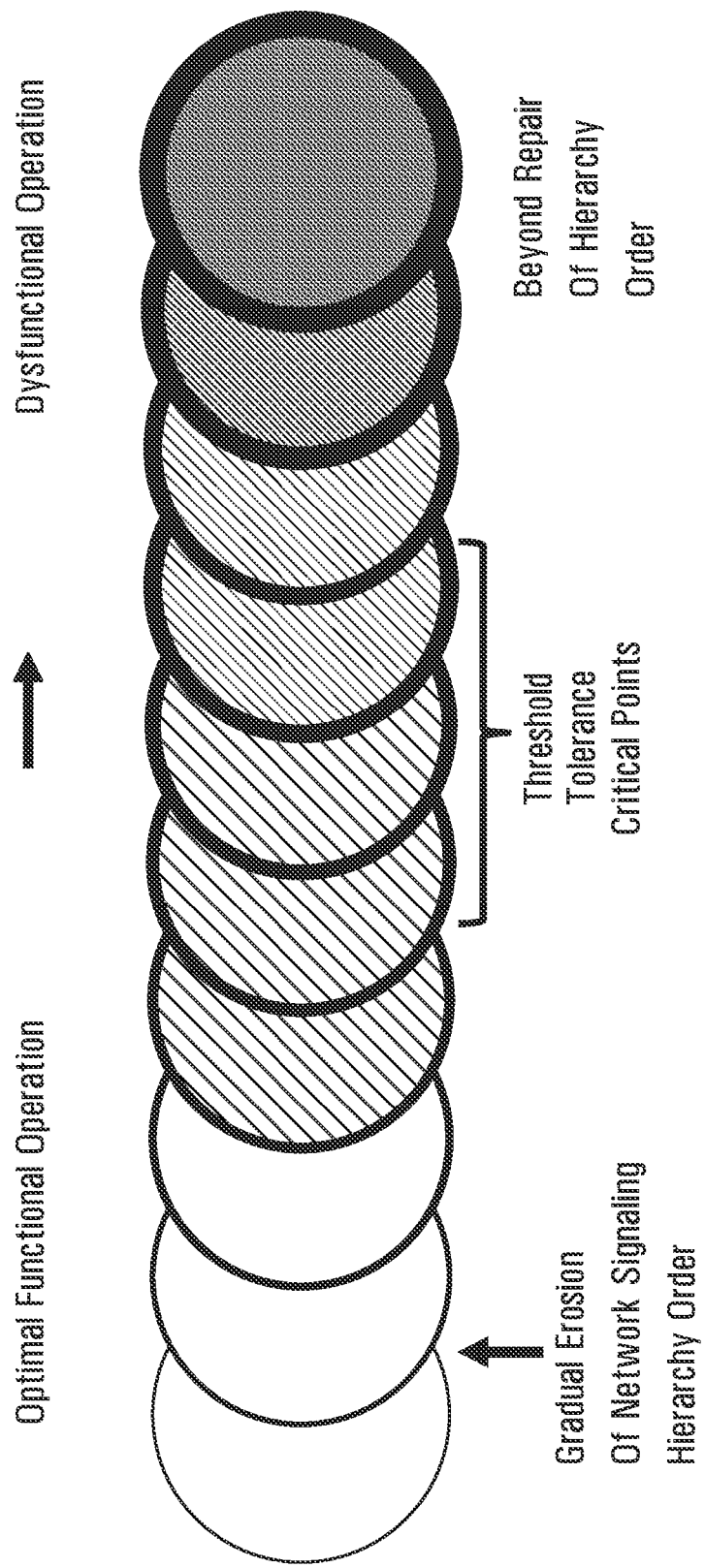
FIG. 5: Schematic showing a non-limiting illustration that proposes a working model for erosion of network signaling during aging.

MicroRNA-34 Family, the Pro-Apoptosis Program in Terminally Differentiated Cardiomyocytes and Neurons, and the Multi-Hit Theory of Age-Dependent Decline:

Beside neuroneogenesis and cardioneogenesis, brain and heart are functionally dependent upon the critical mass of post-mitotic neurons and cardiomyocytes. These permanently non-proliferating cells endure assaults during our life time; over time these accumulated hits lead to disease presentation in later life. The combination of genes and environmental hits may be the simple explanation of the causes underlying the onset of diseases in old age, as illustrated in the FIGS. 4 & 5. Free radical hits come from normal tissue wear-and-tear, and may then activate the microRNA 34 family's expression through a p53-dependent process; eventually the accumulation of such hits may be manifested as increased miR-34a and miR-34c expression in hippocampal neurons, linked to the neuronal cell death observed in Alzheimer's disease by repressing pro-survival factor Bcl2. In the heart, increased levels of miR-34 family members may cause a decrease of SIRT1, which renders the heart undefended from reperfusion-induced injury. Thus, the life-long accumulation of free-radical "hits" may encourage the gradual, steady unwanted increase of miR-34a and miR-34c, which are the roots of decreased prosurvival factor Bcl2 and anti-oxidative defense SIRT1; the combined loss of these two key genes for cell survival and oxidative defense then precipitates pro-cell death signaling in hippocampal neurons and cardiomyocytes.

Preventive Medicine Against Age-Dependent Increase of the miR-34 Family:

Plaque and tangle formation are known as 'tombstone markers' in AD autopsy brains, whose causes occurred many steps and decades prior to their manifestation. Obviously, drugs developed based upon them are retrospective in strategy, aiming to eliminate and/or remove plaque and tangle deposits at the end stage of disease progression. Not surprisingly, many drugs based on this strategy provide little or no benefit. Similarly, the age-dependent decline in defence against post-ischemia reperfusion injury in heart is also approached retrospectively, i.e. how to increase SIRT1 production for robust pre-conditioning to halt further damage to heart tissues. To advance beyond these retroactive approaches, we need an out-of-the-box angle, developing drugs based on reducing the levels of expression of age-dependent increased miRNAs such as the miR-34 family, at mid-life or even earlier, before disease progression or staging such as AD developing to the symptomatic, 'tombstone' stage, or for the heart to suffer impaired response to reperfusion injury-induced tissue damage, as shown by the FIG. 5, preventing miR-34a and miR-34c from increasing beyond the threshold of tolerance. The herein described non-human animal models with overexpression of the key miR-34 family, miR-34a and miR-34c, mimic old-age increased levels, and support candidate therapeutic compound development towards prospective strategies to retard, reduce, and possibly halt their increase and consequential disease development, by dampening the increase away from the threshold "unsafe" zone, through new compounds, such as for example exosomic shuttles to provide antagomirs to inhibit miR-34 family function or reduce their production.

The following clauses provide a further description of examples of transgenic, non-human animal model for accelerated aging and/or age-related symptom, recombinant nucleic acid molecules, cells and methods that can be used to make such animal model and cells, methods of using the animal model and cells, to descendants of the transgenic non-human animal, obtained by breeding with the same or with another phenotype, and to a cell line or primary cell culture or to an organotypic brain slice culture, derived from the transgenic non-human animal or its descendants.

1. A non-human transgenic animal or progeny thereof model for accelerated aging and/or an age-related symptom, where the genome of the non-human transgenic animal or progeny thereof comprises a promoter construct operably linked to a heterologous nucleic acid molecule comprising a microRNA sequence selected from miR-34a and miR-34c.

2. A non-human transgenic animal or progeny thereof according to clause 1, wherein the promoter is a brain specific promoter.

3. A non-human transgenic animal or progeny thereof according to clause 1 or 2, wherein the promoter is the synapsin (SYN) promoter.

4. A non-human transgenic animal or progeny thereof according to clause 1, wherein the promoter is a systemic promoter.

5. A non-human transgenic animal or progeny thereof according to clause 1 or 4, wherein the promoter is the Ubiquitin C (UBI) promoter.

6. A non-human transgenic animal or progeny thereof according to any one of clauses 1 to 5, wherein the microRNA is miR-34c.

7. A non-human transgenic animal or progeny thereof according to any one of clauses 1 to 5, wherein the microRNA is miR-34a.

8. A non-human transgenic animal or progeny thereof according to any one of clauses 1 to 5, wherein the age-related symptom is a neurodegenerative disease, preferably Alzheimer's disease.

9. A non-human transgenic animal or progeny thereof according to any one of clauses 1 to 5, wherein the age-related symptom is a cardiovascular disease, preferably myocardial infarction.

10. A non-human transgenic animal or progeny thereof according to any one of clauses 1 to 9, wherein the animal is a rodent.

11. A non-human transgenic animal or progeny thereof according to any one of clauses 1 to 9, wherein the animal is a mouse.

12. A non-human transgenic animal or progeny thereof according to any one of clauses 1 to 10, wherein the sequence is selected from a microRNA precursor sequence, a pro-microRNA sequence, a mature sequence, or any combinations thereof.

13. A method for use in connection with a process for selecting a candidate therapeutic compound for treating, preventing or delaying accelerated aging and/or an age-related symptom, said method comprising: processing a sample from a non-human transgenic animal or progeny thereof according to any one of clauses 1 to 12 for determining a level of a circulating microRNA selected from miR-34a and miR-34c, and/or a circulating level of a target polypeptide thereof, wherein the non-human transgenic animal or progeny thereof has been contacted with a compound; processing the level of the respective circulating microRNA and/or polypeptide target thereof at least in part based on a reference level to derive information conveying whether the compound has therapeutic activity for treating, delaying or preventing accelerated aging and/or an age-related symptom; and causing conveyance of the information to a recipient for selecting the candidate therapeutic compound at least partly based on the information.

14. A method for selecting a candidate therapeutic compound for treating, preventing or delaying accelerated aging and/or an age-related symptom, said method comprising: causing a non-human transgenic animal or progeny thereof according to any one of clauses 1 to 12 to contact with a compound; causing a determination of a level of a circulating microRNA selected from miR-34a and miR-34c, and/or a circulating level of a target polypeptide thereof from the animal or progeny thereof; obtaining information that is indicative of whether the compound is a candidate therapeutic compound for treating, delaying or preventing accelerated aging and/or an age-associated symptom, said information being obtained from a comparison of the level of the respective circulating microRNA and/or target polypeptide thereof in presence of the compound to a reference level, and selecting the candidate therapeutic compound at least partly based on said information.

15. A recombinant nucleic acid molecule comprising a promoter operably linked to a heterologous nucleic acid molecule comprising the microRNA sequence selected from miR-34a, miR-34c, or a combination thereof.

16. A recombinant nucleic acid molecule according to clause 15, wherein the sequence is selected from a microRNA precursor sequence, a pro-microRNA sequence, a mature sequence, or any combinations thereof.

17. A recombinant nucleic acid molecule according to clause 15 or 16, wherein the promoter is a brain specific promoter.

18. A recombinant nucleic acid molecule according to clause 17, wherein the promoter is the Synapsin (SYN) promoter.

19. A recombinant nucleic acid molecule according to clause 15 or 16, wherein the promoter is a systemic promoter.

20. A recombinant nucleic acid molecule according to clause 19, wherein the promoter is the Ubiquitin C (UBI) promoter.

21. A host cell comprising the recombinant nucleic acid molecule according to any one of clauses 15 to 20.

22. A method of making a non-human transgenic animal model for accelerated aging and/or an age-related symptom, the method comprising introducing a recombinant nucleic acid according to any one of clauses 15 to 20 into an egg cell or embryonic cell of a non-human embryo, implanting the egg or embryonic cell into a compatible female host, and raising the egg or embryonic cell to viability in the female host.

23. A method for selecting a candidate therapeutic compound for treating, delaying or preventing accelerated aging and/or an age-associated symptom, the method comprises providing a cell that includes a transgene capable of expressing a microRNA selected from miR-34a and miR-34c; determining the intracellular level of the microRNA and/or of a target polypeptide thereof after contacting the cell with a compound; processing the intracellular level at least in part based on a reference level to derive information conveying whether the compound has therapeutic activity for treating, delaying or preventing accelerated aging and/or an age-associated symptom; and selecting the candidate therapeutic compound at least partly based on this information.

24. A method for selecting a candidate therapeutic compound for treating, delaying or preventing accelerated aging and/or an age-associated symptom, comprising measuring an intracellular level of a microRNA selected from miR-34a and miR-34c or target polypeptide thereof in a cell that includes a transgene capable of expressing said microRNA, said level being a first level; contacting the cell with a compound; measuring the intracellular level of said microRNA or target polypeptide thereof after the contacting step, said level being a second level; processing the second level at least in part based on the first level to derive information conveying whether the compound has therapeutic activity for treating, delaying or preventing accelerated aging and/or an age-associated symptom; and selecting the candidate therapeutic compound at least partly based on this information.

25. A cell isolated from, or a cell line obtained from, or a primary cell culture obtained from, or an organotypic brain slice culture obtained from the transgenic non-human animal or progeny thereof according to any one of clauses 1 to 12.

26. A primary cell culture according to clause 25, wherein the primary cell culture is a neuronal primary cell culture, or a cardiac primary cell culture, or a stem cell primary cell culture.

27. A primary cell culture according to clause 26, wherein the stem cell primary cell culture is differentiated into a fibroblast cell culture.

28. A primary cell culture according to clause 27, wherein the fibroblast cell culture is reprogrammed into inducible pleuripotent stem (iPS) cell culture.

29. A primary cell culture according to clause 28, wherein the iPS cell culture is differentiated into neuronal stem or cardiomyocytes stem lineage cell culture.

Without intent to limit the scope of the invention, exemplary instruments, apparatus, methods and their related results according to embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the present disclosure without regard for any particular theory or scheme of action.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps. It will also be understood by those of skill in the art that the transitional phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Although the present invention has been described in considerable detail with reference to certain embodiments thereof, variations and refinements are possible without departing from the spirit of the invention. While the compositions and methods of this invention have been described in terms of preferred embodiments, it will be apparent to those of skill in the art that variations can be applied to the compositions and/or methods and in the steps or in the sequence of steps of the method described herein without departing from the concept and scope of the invention. All such similar substitutes and modifications apparent to those skilled in the art are deemed to be within the scope and concept of the invention as defined by the appended claims.

All U.S. patent and patent application references cited throughout the specification are hereby incorporated by reference in their entirety.

The foregoing is considered as illustrative only of the principles of the invention. Further, since numerous modifications and changes will readily occur to those skilled in the art, it is not desired to limit the invention to the exact examples and embodiments shown and described, and accordingly, all suitable modifications and equivalents may be resorted to, falling within the scope of the invention.

REFERENCES

1. Ruvkun, G., Wightman, B., and Ha, I. (2004) The 20 years it took to recognize the importance of tiny RNAs. *Cell* S116: S93-S96 ff.
2. Kosik, K. S, and Krichevsky, A. M. (2005) The elegance of the MicroRNAs: a neuronal perspective. *Neuron* 47: 779-782.
3. Croce, C. M. and Calin, G. A. (2005) miRNAs, cancer, and stem cell division. *Cell* 122(1): 6-7.
4. Costa, F. F. (2005) Non-coding RNAs: new players in eukaryotic biology. *Gene* 357(2): 83-94.
5. Finnegan, E. J. and Matzke, M. A. (2003) The small RNA world. *Journal of Cell Science* 116: 1489-1493.
6. Lau, N. C., Lim, L. P., Weinstein, E. G., and Bartel, D. P. (2001) An abundant class of tiny RNAs with probable regulatory roles in *Caenorhabditis elegans*. *Science* 294: 858-862.
7. Meltzer, P. S. (2005) Cancer genomics: small RNAs with big impacts. *Nature* 435: 745-746.
8. Bartel, D. P. (2004) MicroRNAs: genomics, biogenesis, mechanism, and function. *Cell* 116: 281-297.
9. Smith, C. (2005) Genomics: getting down to details. *Nature* 435(7044): 991-994.
10. Lim, L. P., Glasner, M. E., Yekta, S., Burge, C. B., and Bartel, D. P. (2003) Vertebrate microRNA genes. *Science* 299: 1540.
11. Reinhart, B. J., Slack, F. J., Basson, M., Pasquinelli, A. E., Bettinger, J. C., Rougvie, A. E., Horvitz, H. R., and Ruvkun, G. (2000) The 21-nucleotide let-7 RNA regulates developmental timing in *Caenorhabditis elegans*. *Nature* 403: 901-906.
12. Mourelatos, Z. (2008) Small RNAs: the seeds of silence. *Nature* 455: 44-45.
13. Baek, D., Villen, J., Shin, C., Camargo, F. D., Gygi, S. P., and Bartel, D. P. (2008) The impact of microRNAs on protein output. *Nature* 455: 64-71.
14. Chen, K. and Rajewsky, N. (2006) Natural selection on human microRNA binding sites inferred from SNP data. *Nat. Genet.* 38(12), 1452-1456.
15. Clop, A., Marcq, F., Takeda, H., Pirottin, D., Tordoir, X., Bibe, B., Bouix, J., Caiment, F., Elsen, J. M., Eychenne, F., Larzul, C., Laville, E., Meish, F., Milenkovic, D., Tobin, J., Charlier, C., and Georges, M. (2006) A mutation creating a potential illegitimate microRNA target site in the myostatin gene affects muscularity in sheep. *Nat. Genet.* 38(7): 813-818.
16. Brendle, A., Lei, H., Brandt, A., Johansson, R., Enquist, K., Henriksson, R., Hemminki, K., Lenner, P., and Forsti, A. (2008) Polymorphisms in predicted microRNA-binding sites in integrin genes and breast cancer: ITGB4 as prognostic marker. *Carcinogenesis* 29: 1394-1399.
17. Lodygin, D., Tarasov, V., Epanchintsev, A., Berking, C., Knyazeva, T., Körner, H., Knyazev, P., Diebold, J., and Hermeking, H. (2008) Inactivation of miR-34a by aberrant CpG methylation in multiple types of cancer. *Cell Cycle* 7(16): 2591-2600.
18. Qiu, Z. and Ghosh, A. (2008) A brief history of neuronal gene expression: regulatory mechanisms and cellular consequences. *Neuron* 60(3): 449-455.
19. Ooi, L. and Wood, I. C. (2008) Regulation of gene expression in the nervous system. *Biochem. J.* 414: 327-341.
20. Sylvestre, Y., deGuire, V., Querido, E., Mukhopadhyay, U. L., Bourdeau, V., Major, F., Ferbeyre, G., and Chartrand, P. (2007) An E2F/miR-20a autoregulatory feed-back loop. *J. Biol. Chem.* 282(4): 2135-2145.
21. Cannell, I. G., Kong, Y. W., and Bushell, M. (2008) How do microRNAs regulate gene expression? *Biochem. Soc. Trans.* 36: 1224-1231.
22. Kong, W., Yang, H., He, L., Zhao, J. J., Coppola, D., Dalton, W. S., and Cheng, J. Q. (2008) MicroRNA-155 is regulated by the transforming growth factor beta/Smad pathway and contributes to epithelial cell plasticity by targeting RhoA. *Mol. Cell. Biol.* 22: 6773-6784.
23. Bracken, C. P., Gregory, P. A., Kolesnikoff, N., Bert, A. G., Wang, J., Shannon, M. F., and Goodall, G. J. (2008) A double-negative feedback loop between ZEB1-S1P1 and the microRNA-200 family regulates epithelial-mesenchymal transition. *Cancer Res.* 68: 7846-7854.
24. Medina, P. P. and Slack, F. J. (2008) microRNAs and cancer: An overview. *Cell Cycle* 7(16): 2485-2492.
25. Woods, K., Thomson, J. M., and Hammond, S. M. (2007) Direct regulation of an oncogenic microRNA cluster by E2F transcription factors. *J. Biol. Chem.* 282(4): 2130-2134.
26. Garzon, R., Fabbri, M., Cimmino, A., Calin, G. A., and Croce, C. M. (2006) MicroRNA expression and function in cancer. *Trends Mol. Med.* 12(12): 580-587.
27. Kato, M. and Slack, F. J. (2008) microRNAs: small molecules with big roles—*C. elegans* to human cancer. *Biol. Cell* 100(2): 71-81.
28. Wang, Y., Liang, Y., and Lu, Q. (2008) MicroRNA epigenetic alterations: predicting biomarkers and therapeutic targets in human diseases. *Clin Genet.* 74(4):307-315.
29. Yu, F., Yao, H., Zhu, P., Zhang, X., Pan, Q., Gong, C., Huang, Y., Hu, X., Su, F., Lieberman, J., and Song, E. (2007) let-7 regulates self renewal and tumorigenicity of breast cancer cells. *Cell* 131(6): 1109-1123.
30. El Ouaamari, A., Baroukh, N., Martens, G. A., Lebrun, P., Pipeleers, D., and van Obberghen, E. (2008) miR-375 targets 3'-phosphoinositides-dependent protein kinase-1 and regulates glucone-induced biological responses in pancreatic beta-cells. *Diabetes* 10: 2708-2717.
31. Krützfeldt, J., Rajewsky, N., Braich, R., Rajeev, K. G. Tuschl, T., Manoharan, M., and Stoffel, M. (2005) Silencing of microRNAs in vivo with 'antagomirs'. *Nature* 348: 685-689.
32. van Rooij, E., Sutherland, L. B., Thatcher, J. E., DiMaio, J. M., Naseem, R. H., Marschall, W. S., Hill, J. A., and Olson, E. N. (2008) Dysregulation of microRNAs after myocardial infarction reveals a role of miR-29 in cardiac fibrosis. *Proc. Natl. Acad. Sci. USA* 105: 13027-12032.
33. Succharov, V., Bristow, M. R., and Port, J. D. (2008) miRNA expression in the failing human heart: functional correlates. *J. Mol. Cell. Cardiol.* 45: 185-192.
34. van Rooij, E., Sutherland, L. B., Oi, X., Richardson, J. A., Hill, J., and Olson, E. N. (2007) Control of stress-dependent cardiac growth and gene expression by a microRNA. *Science* 316: 575-579.
35. van Rooij, E., Sutherland, L. B. Liu, N., Williams, A. H., McAnally, J., Gerard, R. D., Richardson, J. A., and Olson, E. N. (2006) A signature pattern of stress-responsive microRNAs that can evoke cardiac hypertrophy and heart failure. *Proc. Natl. Acad. Sci. USA* 203: 18255-18260.
36. Liang, R., Bates, D. J., and Wang, E. Epigenetic Control of MicroRNA Expression and Aging. *Current Genomics* 10: 184-193.
37. He, L., He, X. Y., Lowe, S. W., and Hannon, G. J. (2007) microRNAs join the p53 network—another piece in the tumour-suppression puzzle. *Nature* (Review) 7: 819-822.
38. He, X. Y., He, L., and Hannon, G. J. (2007) The Guardian's little helper: microRNAs in the p53 tumor suppressor network. *Cancer Res.* 67: 11099-10101.
39. Hermeking, H. (2007) p53 enters the microRNA world. Cell 12: 4148.
40. He, L., He, X. Y., Lim, L. P., Stanchina, E. D., Xuan, Z. Y., Liang, Y., Xue, W., Zender, L., Magnus, J., Ridzon, D., Jackson, A. L., Linsley, P. S., Chen, C., Lowe, S. W., Cleary, M., and Hannon, G. J. (2007) A microRNA component of the p53 tumor suppressor network. *Nature* 447: 1130-1134.
41. Yamakuchi, M., Ferlito, M., and Lowenstein, C. J. (2008) miR-34a repression of SIRT1 regulates apoptosis. *Proc. Nat'l Acad. Sci. USA* 105: 13421-13426.
42. Wei, J. S., Song, Y. K., Durinck, S., Chen, Q. R., Cheuk, A. T., Tsang, P., Zhang, Q., Theiele, C. J., Slack, A., Shohet, J., and Khan, J. (2008) The MYCN oncogene is a direct target of miR-34a. *Oncogene* 27: 5204-5213.
43. Sun, F., Fu, H., Liu, Q., Tie, Y., Zhu, J., Xing, R., Sun, Z., and Zheng, X. (2008) Downregulation of CCND1 and CDK6 by miR-34a induces cell cycle arrest. *FEBS Lett.* 582: 1564-1568.
44. Tazawa, H., Tsuchiya, N., Izumiya, M., and Nakagama, H. (2007) Tumor-suppressive miR-34a induces senescence-like growth arrest through modulation of the E2F pathway in human colon cancer cells. *Proc. Nat'l Acad. Sci. USA* 104(39):15472-15477.
45. Tarasov, V., Jung, P., Verdoodt, B., Lodygin, D., Epanchintsev, A., Menssen, A., and Meister, G. (2007) Differential regulation of microRNAs by p53 revealed by massively parallel sequencing: miR-34a is a p53 target that induces apoptosis and G1-arrest. *Cell Cycle* 6(13):1586-1593.
46. Corney, D. C., Flesken-Nikitin, A., Godwin, A. K., Wang, W., and Nikitin, A. Y. (2007) MicroRNA-34b and MicroRNA-34c are targets of p53 and cooperate in control of cell proliferation and adhesion-independent growth. *Cancer Res.* 67: 8433-8438.
47. Liang, Y. (2008) An expression meta-analysis of predicted microRNA targets identifies a diagnostic signature for lung cancer. *BMC Med. Genomics* 1: 61.
48. Park, S. Y., Lee, J. H., Ha, M., Nam, J. W., and Kim, V. N. (2009) miR-29 miRNAs activate p53 by targeting p85 alpha and CDC42. *Nat. Struct. Mol. Biol.* 16(1):23-29.
49. Yamakuchi, M. and Lowenstein, C. J. (2009) MiR-34, SIRT1, and p53: the feedback loop. *Cell Cycle* 8: 712-715.
50. Walsh, D. M. and Selkoe, D. J. (2007) A beta oligomers—a decade of discovery. *J. Neurochem.* 101: 1172-1184.
51. Hardy, J. and Selkoe, D. J. (2002) The amyloid hypothesis of Alzheimer's disease: progress and problems on the road to therapeutics. *Science* 297: 353-356.
52. McGowan, E., Eriksen, J., and Hutton, M. (2006) A decade of modeling Alzheimer's disease in transgenic mice. *Trends Genet.* 22(5): 281-9.
53. Zhang, Q., Zhang, X., and Sun, A. (2009) Truncated tau at D421 is associated with neurodegeneration and tangle formation in the brain of Alzheimer transgenic models. *Acta Neuropathol.* 117(6): 687-97.
54. Benveniste, H., Ma, Y., Dhawan, J., Gifford, A., Smith, S. D., Feinstein, I., Du, C., Grant, S. C., and H of, P. R. (2007) Anatomical and functional phenotyping of mice models of Alzheimer's disease by MR microscopy. *Ann NY Acad. Sci.* 1097: 12-29.
55. Pallasa, M., Caminsa, A., Smith, M. A., Perry, G., Leeb, H., and Casadesus, G. (2008) From Aging to Alzheimer's Disease: Unveiling "The Switch" with the Senescence-Accelerated Mouse Model (SAMP8). *Journal of Alzheimer's Disease* 15: 615-624.
56. Woodruff-Pak, D. (2008) Animal models of Alzheimer's disease: Therapeutic Implications. *Jour. of Alzheimer Disease* 15: 507-521.
57. Wang E. (2007) MicroRNA, the putative molecular control for mid-life decline. *Aging Research Review* 6(1): 1-11.
58. Finch, C. E. (2009) The neurobiology of middle-age has arrived. *Neurobiology of Aging* 30: 515-520.
59. Hoon, D. S., Ferris, R., Tanaka, R., Chong, K. K., Alix-Panabières, C., and Pantel, K. (2011) Molecular mechanisms of metastasis. *J Surg Oncol.* 103(6): 508-17. doi: 10.1002/jso.21690.
60. Suarez-Gomez, M., Alejandre-Duran, E., and Ruiz-Rubio, M. (2011) [MicroRNAs in bipolar disorder: diagnostic and therapeutic applications.] *Rev Neurol.* 53(2): 91-98.
61. Turchinovich, A., Weiz, L., Langheinz, A., and Burwinkel, B. (2011) Characterization of extracellular circulating microRNA. *Nucleic Acids Res. [Epub ahead of print] PMID:* 21609964.
62. Weng, H., Shen, C., Hirokawa, G., Ji, X., Takahashi, R., Shimada, K., Kishimoto, C., and Iwai, N. (2011) Plasma miR-124 as a biomarker for cerebral infarction. *Biomed Res.* 32(2): 135-41.
63. Kotlabova, K., Doucha, J., and Hromadnikova, I. (2011) Placental-specific microRNA in maternal circulation—identification of appropriate pregnancy-associated microRNAs with diagnostic potential. *J Reprod Immunol.* 89(2): 185-91
64. Gaughwin, P. M., Ciesla, M., Lahiri, N., Tabrizi, S. J., Brundin, P., and Björkqvist, M. (2011) Hsa-miR-34b is a plasma-stable microRNA that is elevated in pre-manifest Huntington's disease. *Hum Mol. Genet.* 20(11): 2225-37
65. Smalheiser, N. R. (2007) Exosomal transfer of proteins and RNAs at synapses in the nervous system. *Biol Direct.* 2: 35.

66. Li, N., Bates, D. J., An, J., and Wang, E. (2011) Up-regulation of key microRNAs and the inverse down-regulation of their potential target genes of oxidative phosphorylation during aging in mouse brains. *Neurobiology of Aging.* 32: 944-955.
67. De Sandre-Giovannoli, A., Bernard, R., Cau, P., Navarro, C., Amiel, J., Boccaccio, I., Lyonnet, S., Stewart, C. L., Munnich, A., Le Merrer, M., and Levy, N. (2003) Lamin a truncation in Hutchinson-Gilford progeria. *Science.* 300: 2055.
68. Eriksson, M., Brown, W. T., Gordon, L. B., Glynn, M. W., Singer, J., Scott, L., Erdos, M. R., Robbins, C. M., Moses, T. Y., Berglund, P., Dutra, A., Pak, E., Durkin, S., Csoka, A. B., Boehnke, M., Glover, T. W., and Collins, F. S. (2003) Recurrent de novo point mutations in lamin A cause Hutchinson-Gilford progeria syndrome. *Nature.* 423:293-298.
69. Tsurimoto T, Shinozaki A, Yano M, Seki M, Enomoto, T. (2005) Human Werner helicase interacting protein 1 (WRNIPl) functions as a novel modulator for DNA polymerase delta. *Genes Cells.* 10(1):13-22.
70. Camougrand, N. & Rigoulet, M. (2001). Aging and oxidative stress: studies of some genes involved both in aging and in response to oxidative stress. *Resp. Physiol.* 128: 393-401.
71. Sohal, R. S. Aging, cytochrome oxidase activity and hydrogen peroxide release by mitochondria. (1993). *Free Radic. Biol. Med.* 14: 583-588.
72. Agarwal, S. & Sohal, R. S. (1995). Differential oxidative damage to mitochondrial proteins during aging. *Mech. Ageing Dev.* 85: 55-63
73. Finkel, T. & Holbrook, N. J. (2000) Oxidants, oxidative stress and the biology of aging. *Nature* 408:239-247.
74. Hayflick, L. and Moorhead, P. S. (1961) The serial cultivation of human diploid cell strains. *Exp. Cell Res.* 25:585-621.
75 Hayflick, L. (1965) The limited in vitro lifetime of human diploid cell strains. *Exp. Cell Res.* 37:614-636.
76. Martin, G. M., Sprague, C. A., and Epstein, C. J. (1970) Replicative lifespan of cultivated human cells—Effects of donor age, tissue and genotype. *Lab. Invest.* 23:86-92.
77. Goldstein, S. (1990) Replicative senescence: the human fibroblast comes of age. Science 249:1129-1133.
78. Goldstein, S, and Singal, D. P. (1974) Senescence of cultured human fibroblasts: mitotic versus metabolic time. *Exp. Cell Res.* 88:359-364.
79. Hensler, P. J., Annab, L. A., Barrett, J. C., and Pereira-Smith, O. M. (1994) A gene involved in control of human cellular senescence on human chromosome 1q. *Mol. Cell. Biol.* 14:2291-2297.
80. Ning, Y., Weber, J. L., Killary, A. M., Ledbetter, D. H., et al. (1991) Genetic analysis of indefinite division in human cells: evidence for a cell senescence-related gene(s) on human chromosome 4. *Proc. Nat'l Acad. Sci. USA* 88:5635-5639.
81. Annab, L. A., Dong, J. T., Futreal, P. A., Satoh, H., et al. (1992) Growth and transformation suppressor genes for BHK Syrian hamster cells on human chromosomes 1 and 11. *Mol. Carcinog.* 6: 280-288.
82. Seshadri, T. and Campisi, J. (1990) Repression of c-fos transcription and altered genetic program in senescent human fibroblasts. *Science* 247:205-209.
83. Stein, G. H., Beeson, M., and Gordon, L. (1990) Failure to phosphorylate the retinoblastoma gene product in senescent human fibroblasts. *Science* 249:666-669.
84. Harley, C. B., Futcher, A. B. and Greider, C. W. (1990) Telomeres shorten during ageing of human fibroblasts. *Nature* (London) 345:458-460.
85. Guarente, L. (1996) Do changes in chromosomes cause aging? *Cell* 86:9-12.
86. Harper, J. W., Adami, G. R., Wei, N., Keyomarsi, K., and Elledge, S. J. (1993) The p21 Cdk-lnteracting protein Cip1 is a potent inhibitor of $G_1$ cyclin-dependent kinases. *Cell* 75:805-816.
87. El-Deiry, W. S., Tokino, T., Velculescu, V. E., Levy, D. B., Parsons, R., Trent, J. M., Lin, D., Mercer, W. E., Kinzler, K. W., and Vogelstein, B. (1993) WAF1, a potential mediator of p53 tumor suppression. Cell 75:817-825.
88. Xiong, Y., Hannon, G. J., Zhang, H., Casso, D., Kobayashi, R., and Beach, D. (1993) p21 is a universal inhibitor of cyclin kinases. *Nature* 366:701-704.
89. Alcorta, D. A., Xiong, Y., Phelps, D., Hannon, G., Beach, D., and Barrett, J. C. (1996) Involvement of the cyclin-dependent kinase inhibitor p16 (INK4a) in replicative senescence of normal human fibroblasts. *Proc. Natl. Acad. Sci. USA* 93:13742-13747.
90. Reznikoff, C. A., Yeager, T. R., Belair, C. D., Savelieva, E., Puthenveettil, J. A., and Stadler, W. M. (1996) Elevated p16 at senescence and loss of p16 at immortalization in human papillomavirus 16 E6, but not E7, transformed human uroepithelial cells. *Cancer Res.* 56:2886-2890.
91. Serrano, M., Lin, A. W., McCurrach, M. E., Beach, D., and Lowe, S. W. (1997) Oncogenic ras provokes premature cell senescence associated with accumulation of p53 and p16$^{INK}$4a. *Cell* 88:593-602.
92. Zhu, J., Woods, D. McMahon, M., and Bishop, J. M. (1998) Senescence of human fibroblasts induced by oncogenic Raf. Genes & Development 12:2997-3007.
93. McConnell, B. B., Starborg, M., Brookes, S., and Peters, G. (1998) Inhibitors of cyclin-dependent kinase induce features of replicative senescence in early passage human diploid fibroblasts. *Curr. Biol.* 8:351-354.
94. Venable, M. E., Lee, J. Y., Smyth, M. J., Bielawska, A., and Obeid, L. M. (1995) Role of ceramide in cellular senescence. *J. Biol. Chem.* 51:30701-30708.
95. Rudolph, C., Halle, J. P., and Adam, G. (1998) Accelerated proliferative senescence of rat embryo fibroblasts after stable transfection of multiple copies of the c-Myc DNA binding sequence. *Exp. Cell Res.* 239:361-369.
96. Wang, E. (1995) Failure to undergo programmed cell death in senescent human fibroblasts is related to inability to down-regulate bcl2 presence. *Cancer Res.* 55:2284-2292.
97. Shay, J. W. and Wright, W. R. (1991) Defining the molecular mechanisms of human cell immortalization. *Biochim. et Biophys. Acta* 1071:1-7.
98. Ito T, Yagi S, Yamakuchi M. (2010) MicroRNA-34a regulation of endothelial senescence. *Biochem Biophys Res Commun.* 398(4):735-740.
99. Rodier, F. and Campisi, J. (2011) Four faces of cellular senescence. *J. Cell Biol.* 192: 547-556.
100. Corney, D. C., Flesken-Nikitin, A., Godwin, A. K., Wang, W., and Nikitin, A. Y. (2007) MicroRNA-34b and MicroRNA-34c are targets of p53 and cooperate in control of cell proliferation and adhesion independent growth. *Cancer Res.* 67: 8433-8438.
101. Li, N., Muthusamy, S., Liang, R., Sarojini, H., and Wang, E. (2011) Increased expression of miR-34a and miR-93 in rat liver during aging and their impact on the expression of Mgst1 and Sirt1. *Mechanisms of Ageing and Development* 132: 75-85.
102. Khana, A., Muthusamy, S., Liang, R., Sarojini, H., and Wang, E. (2011) Gain of survival signaling by down-regulation of three key miRNAs in brain of calorie-restricted mice. *Aging* 3(3): 1-14.

103. Wang, X., Liu, P., Zhu, H., Xu, Y., Ma, C., Dai, X., Huang, L., Liu, Y., Zhang, L., and Qin, C. (2009) miR-34a, a microRNA up-regulated in a double transgenic mouse model of Alzheimer's disease, inhibits bcl2 translation. *Brain Research Bulletin* 80: 268-273.

104. Zovoilis, A., Agbemenyah, H. Y., Agis-Balboa, R. C., Stilling, R. M., Edbauer, D., Rao, P., Farinelli, L., Delalle, I., Schmitt, A., Falkai, P., Bahari-Javan, S., Burkhardt, S., Sananbenesi, F., and Fischer, A. (2011) microRNA-34c is a novel target to treat dementias. EMBO J. 30(20): 4299-308.

105. Liu, N., Landreh, M., Cao, K., Abe, M., Hendriks, G. J., Kennerdell, J. R., Zhu, Y., Wang, L. S., and Bonini, N. M. (2012) The microRNA miR-34 modulates ageing and neurodegeneration in *Drosophila*. Nature 482(7386): 519-23.

106. Yang, J., Chen, D., He, Y., Meléndez, A., Feng, Z., Hong, Q., Bai, X., Li, Q., Cai, G., Wang, J., and Chen, X. (2011) MiR-34 modulates *Caenorhabditis elegans* lifespan via repressing the autophagy gene atg9. *Age* (Dordr). 2011 Nov. 12. [Epub ahead of print] PMID: 22081425.

107. Kosik, K. S. (2009) MicroRNAs tell an evo-devo story. *Nat. Rev. Neurosci.* 10(10): 754-759.

108. de Lencastre, A., Pincus, Z., Zhou, K., Kato, M., Lee, S. S., and Slack, F. J. (2010) MicroRNAs both promote and antagonize longevity in *C. elegans*. Curr Biol. 20(24): 2159-2168.

109. Cho, W. C. (2007) OncomiRs: the discovery and progress of microRNA in cancers. Mol. Cancer. 6: 60.

110. Zhu, W., Shan, X., Wang, T., Shu, Y., and Liu, P. (2010) miR-181b modulates multidrug resistance by targeting BCL2 in human cancer cell lines. *Int. J. Cancer* 127: 2520-2529.

111. Clotman, F., Jacquemin, P., et al. (2005) Control of liver cell fate decision by a gradient of TGFβ signaling modulated by Onecut transcriptional factors. *Genes Dev.* 19: 1849-1845.

112. Shi, G. P., Chapman, H. A., Bhairi, S. M., DeLeeuw, C., Reddy, V. Y., and Weiss, S. J. (1995) Molecular cloning of human cathepsin O, a novel endoproteinase and homologue of rabbit OC2. *FEBS Lett.* 357(2): 129-34.

113. Hodge, L. K., Klassen, M. P., Han, B. X., Yiu, G., Hurrell, J., Howell, A., Rousseau, G., Lemaigre, F., Tessier-Laavingne, M., and Wang, F. (2007) Retrograde BMP signaling regulates trigeminal sensory neuron identities and the formation of precise face maps. *Neuron* 55: 572-586.

114. Francius, C. and Clotman, F. (2010) Dynamic expression of the Onecut transcription factors HNF-6, OC-2, and OC-3 during spinal motor neuron development. *Neuroscience* 165: 116-129.

115. Plaisance, V., Abderrahmani, A., Perret-Menoud, V., Jacquemin, P., Lemaigre, F., and Regazzi, R. (2006) MicroRNA-9 controls the expression of Granuphilin/Slp4 and the secretory response of insulin-producing cells. *J. Biol. Chem.* 281(37): 26932-42.

116. Ho, A. and Shen, J. (2011) Presenilins in synaptic function and disease. Trends Mol. Med. 17: 617-624.

117. Auffret, A., Mariani, J., and Rovira, C. (2010) Age-related progression synaptic dysfunction: the critical role of presenilin 1. *Rev. Neurosci.* 21(4): 239-250.

118. Biswas, S. C., Shi, Y., Vonsattel, J. P., Leung, C. L., Troy, C. M., and Greene, L. A. (2007) Bim is elevated in Alzheimer's disease neurons and is required for beta-amyloid-induced neuronal apoptosis. *J. Neurosci.* 27(4): 893-900.

119. He, X. Y., He, L., and Hannon, G. J. (2007) The Guardian's little helper: microRNAs in the p53 tumor suppressor network. Cancer Res. 67: 11099-101.

120. Herman, B. & Zhang, Y. Apoptosis and successful aging. *Mech. Ageing Dev.* 123, 563-565 (2002).

121. Martindale, J. L. & Holbrook, N. J. Cellular response to oxidative stress: signaling for suicide and survival. *J. Cellular Physiol.* 192, 1-15 (2002).

122. Camougrand, N. & Rigoulet, M. Aging and oxidative stress: studies of some genes involved both in aging and in response to oxidative stress. *Resp. Physiol.* 128, 393-401 (2001).

123. Sohal, R. S. Aging, cytochrome oxidase activity and hydrogen peroxide release by mitochondria. *Free Radic. Biol. Med.* 14, 583-588 (1993).

124. Agarwal, S. & Sohal, R. S. Differential oxidative damage to mitochondrial proteins during aging. *Mech. Ageing Dev.* 85, 55-63 (1995).

125. Finkel, T. & Holbrook, N. J. Oxidants, oxidative stress and the biology of aging. Nature 408, 239-247 (2000).

126. Bonni, A. et al. Cell survival promoted by the Ras-MAPK signaling pathway by transcription-dependent and -independent mechanism. Science 286, 1358-1362 (1999).

127. Datta, S. R., et al. 1999 Cellular survival: a play in three Akts. *Genes Deve.* 13, 2905-2927 (1999).

128. Guarente, L. & Kenyon, C. Genetic pathways that regulate ageing in model organisms. Nature 408, 255-262 (2000).

129. Kenyon, C. A conserved regulatory system for aging. Cell 105, 165-168 (2001).

130. Gems, D. & Partridge, L. Insulin/IGF signaling and ageing: seeing the bigger picture. *Curr. Opin. Genet. Dev.* 11, 287-292 (2001).

131. Kimura, K. D., Tissenbaum, H. A., Liu, Y., & Ruvkun, G. (1997) Daf-2, an insulin receptor-like gene that regulates longevity and diapause in *Caenorhabditis elegans*. Science 277, 942-946.

132. Tissenbaum, H. A. & Ruvkun, G. (1998) An insulin-like signaling pathway affects both longevity and reproduction in *Caenorhabditis elegans*. Genetics 148, 703-717.

133. Tatar, M. et al. (2001). A mutant *Drosophila* insulin receptor homolog that extends life-span and impairs neuroendocrine function. Science 292, 107-110

134. Lithgow, G. I., White, T. M., Melov, S., & Johnson, T. E. (1995). Thermotolerance and extended life-span conferred by single-gene mutations and induced by thermal stress. *Proc. Nat'l Acad. Sci. USA* 92, 7540-7544

135. Larsen, P. L. & Clarke, C. F. (2002). Extension of life-span in *Caenorhabditis elegans* by a diet lacking coenzyme Q. Science 295,120.

136. Jonassen, T., Larsen, P. L., & Clarke, C. F. (2001). A dietary source of coenzyme Q is essential for growth of long-lived *Caenorhabditis elegans* clk-1 mutants. *Proc. Nat'l Acad. Sci. USA* 98, 421-426

137. Johnson, T. E., Henderson, S., Murakami, S., de Castro, E., de Castro, S. H., Cypser, J., Rikke, B., Tedes-co, P., & Link, C. (2002). Longevity genes in the nematode *Caenorhabditis elegans* also mediate increased resistance to stress and prevent disease. *J. Inherit. Metab. Dis.* 25, 197-206

138. Sohal, R. S., Ku, H.-H., Agarwal, S., Forster, M. J., & Lal, H. (1994). Oxidative damage, mitochondrial oxidant generation and antioxidant defenses during aging and in response to food restriction in the mouse. *Mech. Ageing Dev.* 74, 121-133

139. Sohal, R. S., Agarwal, A., Agarwal, S., & Orr, W. C. (1995). Simultaneous overexpression of copper- and zinc-containing superoxide dismutase and catalase retards age-related oxidative damage and increases metabolic potential in *Drosophila melanogaster. J. Biol. Chem.* 270, 15671-15674

140. Lass, A., Agarwal, S., & Sohal, R. S. (1997). Mitochondrial ubiquinone homologues, superoxide radical generation, and longevity in different mammalian species. *J. Biol. Chem.* 272, 19199-19204

141. Yu, H. & Larsen, P. L. (2001). DAF-16-dependent and independent expression targets of DAF-2 insulin receptor-like pathway in *Caenorhabditis elegans* include FKBPs. *J. Mol. Biol.* 314, 1017-1028

142. Trinei, M., Giorgio, M., Cicalese, A., Barozzi, S., Ventura, A., Migliaccio, E., Milia, E., Padura, I. M., Raker, V. A., Mac¬carana, M., Petronilli, V., Minucci, S., Bernardi, P., Lanfrancone, L., & Pelicci, P. G. (2002). A p53-p66Shc signalling pathway controls intracellular redox status, levels of oxidation-damaged DNA and oxidative stress-induced apoptosis. *Oncogene* 21, 3872-3878

142. Anderson, R. M., Bitterman, K. J., Wood, J. G., Medvedik, O., and Sinclair, D. A. (2003) Nicotinamide and PNC1 govern lifespan extension by calorie restriction in *Saccharomyces cerevisiae. Nature* 423: 181-185.

143. Michan, S, and Sinclair, D. (2007) Sirtuins in mammalians: insights into their biological function. *Biochem. J.* 404: 1-13.

144. Kwon, H. S., and Ott, M. (2008) The ups and downs of SIRT1. *Trends Biochem. Sci.* 33: 517-525.

145. Kim, E. J. and Um, S. J. (2008) SIRT1: roles in aging and cancer. BMB Rep. 41: 751-756.

146. Wang, F., Nguyen, M., Qin, F. X., and Tong, Q. (2007) SIRT2 deacetylates FOXO3a in response to oxidative stress and caloric restriction. *Aging Cell* 6: 505-514.

147. Saunders, L. R. and Verdin, E. (2009) Cell biology, stress response, and aging. Science 323: 1021-2.

148. Tang, B. L. and Chua, C. E. (2008) SIRT1 and neuronal diseases. Mol. Aspects. Med. 29: 187-200.

149. Anekonda, R. S. (2006) Resveratrol—a boon for treating Alzheimer's disease? *Brain Res. Rev.* 52: 316-326.

150. Howitz, K. T., Bitterman, K. J., Cohen, H. Y., Lamming, D. W., Lavu, S., Wood, J. G., Zipkin, R. E., Chung, P., Kisielewski, A., Zhang, L. L., Scherer, B., and Sinclair, D. A. (2003) Small molecule activators of sirtuins extend *Saccharomyces cerevisiae* lifespan. *Nature* 425: 191-196.

151. Billette-Guyonnet, S, and Vellas, B. (2008) Caloric restriction and brain function. *Curr. Opin. Clin. Nutr. Metab. Care* 11: 686-692.

152. Qin, W. P., Zhao, W., Ho, L., Wang, J., Walsh, K., Gandy, S., and Pasinetti, G. M. (2008) Regulation of forkhead transcription factor FoxO3a contributes to calorie restriction-induced prevention of Alzheimer's disease-type amyloid neuropathology and spatial memory deterioration. *Ann. N.Y. Acad. Sci.* 1147: 335-347.

153. Chen, J., Zhou, Y. G., Mueller-Steiner, S., Chen, L. F., Kwon, H., Yi, S., Mucke, L., and Gan, L. (2005) SIRT1 protects against microglia-dependent amyloid-β toxicity through inhibiting NF-κB signaling. *J. Biol. Chem.* 280: 40364-40374.

154. Green, K. N., Steffan, J. S., Martinez-Coria, H., Sun, X., Schreiber, S. S., Thompson, L. M., and LaFerla, F. M. (2008) Nicotinamide restores cognition in Alzheimer's disease transgenic mice via a mechanism involving Sirtuin inhibition and selection reduction of Thr231-phosphotau. *J. Neuroscience* 28: 11500-11510.

155. Qin, W. P., Yang, T., Ho, L., Zhao, Z., Wang, J., Chen, L. H., Zhao, W., Thiyagarajan, M., MacGrogan, D., Rodgers, J. T., Puigserver, P., Sadoshima, J., Deng, H. T., Pedrini, S., Gandy, S., Sauve, A. A., and Pasinetti, G. M. (2006) Neuronal SIRT1 activation as a novel mechanism underlying the prevention of Alzheimer disease amyloid neuropathology by calorie restriction. Jour. Biol. Chem. 281: 21745-21754.

155. Lagouge, M., Wuwerx, J., and Rasouri, S. (2007) SIRT1/PGC-1: a neuroprotective axis? *Medecine et Science* 23: 840-844.

156. Kim, D., Nguyen, M. D., Dobbin, M. M., Fischer, A., Sananbenesi, F., Rodgers, J. T., Delalle, I., Baur, J. A., Sui, G. C., Armour, S. M., Puigserver, P., Sinclair, D. A., and Tsai, L. H. (2007) SIRT1 deacetylase protects against neurodegeneration in models for Alzheimer's disease and amyotrophic lateral sclerosis. *The EMBO Journal* 26: 3169-3178.

157. Helisalmi, S., Vepsalainen, S., Hiltunen, M., Koivisto, A. M., Salminen, A., Laakso, M., and Solninen, H. (2008) Genetic study between SIRT1, PPARD, PGC-1α genes and Alzheimer's disease. *J. Neurology* 255: 668-673.

158. Cruz, J. C., Kim, D., Moy, L. Y., Dobbin, M. M., Sun, X., Bronson, R. T., and Tsai, L. H. (2006) p25/cyclin-dependent kinase 5 induces production and intraneuronal accumulation of amyloid beta in vivo. *J. Neurosci.* 26: 10536-10541.

159. Cruz, J. C., Tseng, H. C., Goldman, J. A., Shih, H., and Tsai, L. H. (2003) Aberrant Cdk5 activation by p25 triggers pathological events leading to neurodegeneration and neurofibrillary tangles. *Neuron* 40: 471-483.

160. Tan, L., Yu, J. T., and Guan, H. S. (2008) Resveratrol exerts pharmacological preconditioning by activating PGC-1 alpha. *Med. Hypotheses* 71: 664-667.

161. Lagouge, M., Argmann, C., Gerhart-Hines, Z., Meziane, H., Lerin, C., Daussin, F., Messadeq, N., Milne, J., Lambert, P., Elliott, P., Geny, B., Laakso, M., Puigserver, P., and Auwerx, J. (2006) Resveratrol improves mitochondrial function and protects against metabolic disease by activating SIRT1 and PGC-1alpha. *Cell* 127: 1109-1122.

162. Julien, C., Tremblay, C., Emond, V., Lebbadi, M., Salem, N. Jr., Bennett, D., and Calon, F. (2009) Sirtuin 1 reduction parallels the accumulation of Tau in Alzheimer disease. *J. Neuropathol. Exp. Neurol.* 68: 48-58.

163. Verma, S., Fedak, P. W., Weisel, R. D., Butany, J., Rao, V., Maitland, A., Li, R. K., Dhillon, B., and Yau, T. M. (2002) Fundamentals of reperfusion injury for the clinical cardiologist. *Circulation* 105(20): 2332-2336.

164. Ong, S. G., and Hausenloy, D. J. (2012) Hypoxia-inducible factor as a therapeutic target for cardioprotection *Pharmacol Ther.* 136(1):69-81.

165. Becatti, M., Taddei, N., Cecchi, C., Nassi, N., Nassi, P. A., and Fiorillo C. (2012) SIRT1 modulates MAPK pathways in ischemic-reperfused cardiomyocytes. *Cell Mol Life Sci.;* 69(13):2245-2260.

166. Bernardo, B. C., Gao, X. M., Winbanks, C. E., Boey, E. J., Tham, Y. K., Kiriazis, H., Gregorevic, P., Obad, S., Kauppinen, S., Du, X. J., Lin, R. C., and McMullen, J. R. (2012) Therapeutic inhibition of the miR-34 family attenuates pathological cardiac remodeling and improves heart function. *Proc Natl Acad Sci USA.* 109(43):17615-17620.

167. Iekushi, K., Seeger, F., Assmus, B., Zeiher, A. M., and Dimmeler, S. (2012) Regulation of cardiac microRNAs by bone marrow mononuclear cell therapy in myocardial infarction. *Circulation.* 25(14):1765-1773.

168. Xu, Q., Seeger, F. H., Castillo, J., Iekushi, K., Boon, R. A., Farcas, R., Manayski, Y., Li, Y. G., Assmus, B., Zeiher, A. M., and Dimmeler, S. (2012) Micro-RNA-34a contributes to the impaired function of bone marrow-derived mononuclear cells from patients with cardiovascular disease. *J Am Coll Cardiol.* 59(23):2107-2117.

169. Horie T, Ono K, Horiguchi M, Nishi H, Nakamura T, Nagao K, Kinoshita M, Kuwabara Y, Marusawa H, Iwanaga Y, Hasegawa K, Yokode M, Kimura T, Kita T. (2010) MicroRNA-33 encoded by an intron of sterol regulatory element-binding protein 2 (Srebp2) regulates HDL in vivo. *Proc Natl Acad Sci USA*. 07(40):17321-17326.

170. Anton, M., Gomaa, I. E., von Lukowicz, T., Molls, M., Gansbacher, B., and Würschmidt, F. (2005) Optimization of radiation controlled gene expression by adenoviral vectors in vitro. *Cancer Gene Ther.* 12(7):640-646.

171. Parrinello, S., Samper, E., Krtolica, A., Goldstein, J., Melov, S., and Campisi J. (2003). Oxygen sensitivity severely limits the replicative lifespan of murine fibroblasts. *Nat Cell Biol.* 5(8):741-747

172. Hsiao, K., Chapman, P., Nilsen, S., et al. (1996) Correlative memory deficits, elevation and amyloid plaques in transgenic mice. *Science* 274: 99-102.

173. Hutton, M., Lewis, J., Dickson, D., Yen, S. H., McGowan E. (2001) Analysis of tauopathies with transgenic mice, *Trends Mol Med,* 7(10):467-470.

174. Lewis, J., Dickson, D. W., Lin, W-L, Chisholm, L., Corral, A., Jones, G., Yen, S-H, Sahara, N., Skipper, L., Yager, D., Eckman, C., Hardy, J., Hutton, M., and McGowan E. (2001) Enhanced Neurofibrillary Degeneration in Transgenic Mice Expressing Mutant Tau and App. *Science,* 293(5534):1487-1491.

175. ImaGene Green™ C12 FDG lacZ Gene Expression Kit (1-2904) from Molecular Probe.

176. Takeda, T., Hosokawa, M., and Higuchi, K. (1991) Senescence-accelerated mouse (SAM): A novel murine model of accelerated senescence. J. Amer. Geriatr. Soc. 39: 911-919.

177. Li, Q., Zhao, H. F., Zhang, Z. F., et al. (2009) Long-term green tea catechin administration prevents spatial learning and memory impairment in senescence-accelerated mouse prone-8 mice by decreasing Aβ1-42 oligomers and upregulating synaptic plasticity-related proteins in the hippocampus. Neuroscience 163(3): 741-749.

178. Tajes, M., Gutierrez-Cuesta, J., Folch, J., et al. (2008) Lithium treatment decreases activities of tau kinases in a murine model of senescence. J Neuropathol Exp Neurol. 67(6): 612-623.

179. Takeda, T., Hosokawa, M., Takeshita, S., et al. (1981) A new murine model of accelerated senescence. Mech. Ageing Dev. 17: 183-194.

180. Banks, W. A., Farr, S. A., Morley, J. E., Wolf, K. M., Geylis, V., and Steinitz, M. (2007). Anti-amyloid beta protein antibody passage across the blood-brain barrier in the SAMP8 mouse model of Alzheimer's disease: an age-related selective uptake with reversal of learning impairment. Exp. Neurol. 206: 248-256.

181. Golde, W. T., Gollobin, P., and Rodriguez, L. L. 2005. A rapid, simple, and humane method for submandibular bleeding of mice using a lancet. Lab Animal, Technique 34(2): 39-43

182. Description of the protocol is located at the Agricultural Research Service website 183. Livak, K. and Schmittgen, T. (2001) Analysis of relative expression data using real time quantitative PCR and the ΔΔCt method. Biotechniques Method 26: 402-408.

184. Fleige, S, and Pfaffl, M. W. (2006) RNA integrity and the effect on the real-time qRT-PCR performance. Molecular Aspects of Medicine 27: 126-139.

185. Tsujioka, Y., Takahashi, M., Tsuboi, Y., Yamamoto, T., and Yamada, T. (1999) Localization and expression of cdc2 and cdk4 in Alzheimer brain tissue. Dement Geriatr Cogn Disord. 10(3):192-8.

186. Biswas, S. C., Shi, Y., Vonsattel, J. P., Leung, C. L., Troy, C. M., and Greene L A (2007) Bim is elevated in Alzheimer's disease neurons and is required for beta-amyloid-induced neuronal apoptosis. J. Neurosci. 27(4):893-900.

The invention claimed is:

1. A transgenic mouse or progeny thereof, wherein the genome of the mouse or progeny thereof comprises a construct comprising a heterologous nucleic acid molecule encoding microRNA miR-34a or miR-34c operably linked to a promoter, said mouse or progeny thereof having cells that display increased senescence or apoptosis rate as compared to a wild-type mouse.

2. The transgenic mouse or progeny thereof according to claim 1, wherein said promoter is a brain-specific promoter.

3. The transgenic mouse or progeny thereof according to claim 1, wherein the promoter is the synapsin promoter.

4. The transgenic mouse or progeny thereof according to claim 1, wherein the promoter is a systemic promoter.

5. The transgenic mouse or progeny thereof according to claim 1, wherein the promoter is the Ubiquitin C promoter.

6. The transgenic mouse or progeny thereof according to claim 1, wherein the heterologous nucleic acid molecule encodes microRNA miR-34c.

7. The transgenic mouse or progeny thereof according to claim 1, wherein the heterologous nucleic acid molecule encodes microRNA miR-34a.

8. The transgenic mouse or progeny thereof according to claim 1, wherein said cells are fibroblast cells.

9. An induced pluripotent stem (iPS) cell made using a cell obtained from the transgenic mouse or progeny thereof of claim 1.

* * * * *

SEQUENCE LISTING

```
<160> NUMBER OF SEQ ID NOS: 33

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      MfeI hUbi forward primer

<400> SEQUENCE: 1
caattgagtg gctgggaaat tgaggg                                          26

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      BglII hUbi reverse primer

<400> SEQUENCE: 2
agatctgcat tgtctaacaa aaaagccaaa                                      30

<210> SEQ ID NO 3
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      MfeI mSyn forward primer

<400> SEQUENCE: 3
caattgcggc cactgtgtga agcgct                                          26

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      mSyn reverse primer BamHI

<400> SEQUENCE: 4
ggtggcggcg tggggcaggg gatcc                                           25

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      NheI Lacz forward primer

<400> SEQUENCE: 5
gctagctcgt ttactttgac caacaag                                         27

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Lacz reverse primer

<400> SEQUENCE: 6 ttattttga caccagacca a                                                21

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      LacZ-GT-F Overlap extension primer

<400> SEQUENCE: 7
gttgcagtgc acggcagata cacttgctga                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      LacZ-GT-R Overlap extension primer

<400> SEQUENCE: 8
gccactggtg tgggccataa ttcaattcgc                                      30

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
``` hmiR33a scaffold forward primer

<400> SEQUENCE: 9
cagcctgacc atctgtgaga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      hmiR33a scaffold reverse primer

<400> SEQUENCE: 10
aagcaggtca cacaggaaca                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      hGH poly A signal forward primer

<400> SEQUENCE: 11
tgcatccctg tgaccccctcc c                                           21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      NotI HGH poly A signal reverse primer

<400> SEQUENCE: 12
gcggccgcca tgagaggaca gtgccaagca                                   30

<210> SEQ ID NO 13
<211> LENGTH: 110
<212> TYPE: DNA
<213> ORGANISM: Homo sapiens
<220> FEATURE:
<223> OTHER INFORMATION: hsa-34a Precursor

<400> SEQUENCE: 13
ggccagctgt gagtgtttct ttggcagtgt cttagctggt tgttgtgagc aatagtaagg    60
aagcaatcag caagtatact gccctagaag tgctgcacgt tgtggggccc              110

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      hsa34aSyn forward primer

<400> SEQUENCE: 14
ctcgagggcc agctgtgagt gtttct                                       26

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic

```
              hsa34aSyn and 34aUbi reverse primer

<400> SEQUENCE: 15
gaattcgggc cccacaacgt gcagcac                                          27

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      hsa34aUbi forward primer

<400> SEQUENCE: 16
aagcttggcc agctgtgagt gtttct                                           26

<210> SEQ ID NO 17
<211> LENGTH: 77
<212> TYPE: DNA
<213> ORGANISM: Homo sapiens

<400> SEQUENCE: 17
agtctagtta ctaggcagtg tagttagctg attgctaata gtaccaatca ctaaccacac      60
ggccaggtaa aaagatt                                                     77

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Hsa-mir 34c Syn forward primer

<400> SEQUENCE: 18
ctcgagagtc tagttactag gc                                               22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      Hsa-mir 34c Syn/Ubi reverse primer

<400> SEQUENCE: 19
gaattcaatc tttttacctg gc                                               22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Hsa-miR 34c Ubi forward primer

<400> SEQUENCE: 20
aagcttagtc tagttactag gc                                               22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      forward genotyping primer
```

<400> SEQUENCE: 21
ggattcagct ttccattccc t                                         21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse genotyping primer

<400> SEQUENCE: 22
ctgttcctgt gtgacctgct t                                         21

<210> SEQ ID NO 23
<211> LENGTH: 22
<212> TYPE: RNA
<213> ORGANISM: Homo sapiens
<220> FEATURE:
<223> OTHER INFORMATION: Hsa miR34a mature sequence

<400> SEQUENCE: 23
uggcaguguc uuagcugguu gu                                        22

<210> SEQ ID NO 24
<211> LENGTH: 22
<212> TYPE: RNA
<213> ORGANISM: Homo sapiens
<220> FEATURE:
<223> OTHER INFORMATION: Hsa miR34c mature sequence

<400> SEQUENCE: 24
aaucacuaac cacacggcca gg                                        22

<210> SEQ ID NO 25
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gcgggtgtgg gggccgagag agagatctcg agagtctagt tactaggcag tgtagttagc    60
tgattgctaa tagtaccaat cactaaccac acggccaggt aaaaagattg aattcgtcga   120
caagcttctc gagagtctag ttactaggca gtgtagttag ctgattgcta atagtaccaa   180
tcactaacca cacggccagg taaaaagatt gaattctgca gtcgacgggc ccccatcctg   240
cccctcccag agctggag                                                258

<210> SEQ ID NO 26
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 26
ggccagcugu gaguguuucu uuggcagugu cuuagcugguu guugugagc aauaguaagg    60 aagcaaucag caaguauacu gcccuagaag ugcugcacgu uguggggccc               110

<210> SEQ ID NO 27

<211> LENGTH: 77
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
agucuaguua cuaggcagug uaguuagcug auugcuaaua guaccaauca cuaaccacac    60
ggccagguaa aaagauu                                                  77

<210> SEQ ID NO 28
<211> LENGTH: 154
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 28
agucuaguua cuaggcagug uaguuagcug auugcuaaua guaccaauca cuaaccacac    60
ggccagguaa aaagauuagu cuaguuacua ggcaguguag uuagcugauu gcuaauagua   120
ccaaucacua accacacggc cagguaaaaa gauu                               154

<210> SEQ ID NO 29
<211> LENGTH: 44
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 29
aaucacuaac cacacggcca ggaaucacua accacacggc cagg                     44

<210> SEQ ID NO 30
<211> LENGTH: 625
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30
gtgaggggtg gggtcagggg cctggcaggg ctgggggatt cagcttttcca ttccctggtt    60 cctctcccca gccccaggg gctgcagaag accatgggt tagcccaagc agcacaggat    120
agggggtcca gcagaccctg cttttttggct aaggcttctg tccagaggag aggggttgcc   180
cctatctggc ctcagtttcc ccatccctgg gaggaggggg gtggatggtg tggtaggatc   240
cctttggagg ccctgcatca ggagggctgg acagctgctc ccgggccggt ggcgggtgtg   300
ggggccgaga gagagatctc gagctcaagc ttggccagct gtgagtgttt ctttggcagt   360
gtcttagctg gttgttgtga gcaatagtaa ggaagcaatc agcaagtata ctgccctaga   420
agtgctgcac gttgtggggc ccgaattctg cagtcgacgg gcccccatcc tgcccctccc   480
agagctggag ccctggtgac ccctgccctg cctgccaccc caggccgtg cagctgttcc   540 tgtgtgacct gcttgcatcc ctgtgacccc tccccagtgc ctctcctggc cctggaagtt   600
gccactccag tgcccaccag ccttg                                         625

<210> SEQ ID NO 31
<211> LENGTH: 122

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
aagcttggcc agctgtgagt gtttctttgg cagtgtctta gctggttgtt gtgagcaata      60
gtaaggaagc aatcagcaag tatactgccc tagaagtgct gcacgttgtg gggcccgaat    120
tc                                                                    122

<210> SEQ ID NO 32
<211> LENGTH: 583
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gtgaggggtg gggtcagggg cctggcaggg ctgggggatt cagcttttca ttccctggtt     60
cctctcccca gcccccaggg gctgcagaag accatggggt tagcccaagc agcacaggat   120 aggggg tcca gcagaccctg cttttt ggct aaggcttctg tccagaggag agggg ttgcc   180 cctatctggc ctcagtttcc ccatccctgg gaggaggggg gtggatggtg tggtaggatc   240
cctttggagg ccctgcatca ggagggctgg acagctgctc ccgggccggt ggcgggtgtg   300
ggggccgaga gagagatctc gagagtctag ttactaggca gtgtagttag ctgattgcta   360
atagtaccaa tcactaacca cacggccagg taaaaagatt gaattctgca gtcgacgggc   420
ccccatcctg ccccctcccag agctggagcc ctggtgaccc ctgccctgcc tgccaccccc   480
aggccgtgca gctgttcctg tgtgacctgc ttgcatccct gtgaccctc cccagtgcct    540 ctcctggccc tggaagttgc cactccagtg cccaccagcc ttg                     583

<210> SEQ ID NO 33
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctcgagagtc tagttactag gcagtgtagt tagctgattg ctaatagtac caatcactaa    60
ccacacggcc aggtaaaaag attgaattc                                      89
```